United States Patent [19]
Hayes et al.

[11] Patent Number: 6,096,716
[45] Date of Patent: Aug. 1, 2000

[54] LIPOSOME-MEDIATED TRANSFECTION OF CENTRAL NERVOUS SYSTEM CELLS

[75] Inventors: Ronald L. Hayes; Keyi Yang; Fabrizia Faustinella, all of Houston, Tex.

[73] Assignee: The Board of Regents, The University of Texas System, Austin, Tex.

[21] Appl. No.: 08/353,901

[22] Filed: Dec. 12, 1994

[51] Int. Cl.$^7$ .......................... A01N 43/04; A61K 31/70; C12N 15/63
[52] U.S. Cl. ..................... 514/44; 435/320.1; 435/172.3; 435/69.1; 424/520; 424/570
[58] Field of Search .............................. 435/172.3, 320.1, 435/69.1; 424/520, 570; 514/44

[56] References Cited

FOREIGN PATENT DOCUMENTS

93/353901  5/1993  WIPO ................................... 424/520

OTHER PUBLICATIONS

Yang et al., Molecular Neuroscience, vol. 8, pp. 2355–2358, Jul. 7, 1997.
Afione et al., Clin. Pharmacokinet., vol. 28, pp. 181–189, Mar. 15, 1995.
Weatherall et al., British Medical Bulletin, vol. 51, pp. 1–11, 1995.
Ledley, Fred D., Current Opinion in Biotechnology, vol. 5, pp. 626–636, 1994.
Schofield and Caskey, British Medical Bulletin, vol. 51, pp. 56–71, 1995.
Marshall, Eliot, Science, vol. 269, pp. 1050–1055, Aug. 25, 1995.
Coghlan, Andy, Focus, vol. 145, pp. 14–15, Nov. 25, 1995.
Brown, "News Media, Researchers 'Oversold' Gene Therapy, Advisory Panel Says", Wash. Post, Dec. 8, 1995.
Hayes et al., Neuroscience Letters, vol. 191, pp. 121–125, May 19, 1995.
Friedmann, Theodore, Trends In Genetics, vol. 10, pp. 210–214, Jun. 1994.
Anderson, W. French, Human Gene Therapy, vol. 5, pp. 281–282, 1994.
Felgner et al., Proc. Natl. Acad. Sci. USA, vol. 84, pp. 7413–7417, 1987.
Huang, Leaf, Journal of Liposome Research, vol. 3, pp. 71–84, Mar. 24, 1993.
Arai et al., "Calpain Inhibitors Improve the Recovery of Synaptic Transmission from Hypoxia in Hippocampal Slices," *Brain Research,* 532:63–68, 1990.
Banik et al., "Degradation of Cytoskeletal Proteins in Experimental Spinal Cord Injury," *Neurochemical Research,* 7(12):1465–1475, 1982.
Barker and Murphy, "The Nerve Growth Factor Receptor: a Multicomponent System that Mediates the Actions of the Neurotrophin Family of Proteins," *Molecular and Cellular Biochemistry,* 110:1–15, 1992.
Barinega, M., "Solving the Delivery Puzzle," *Science,* 264, 773, May 1994.
Battleman et al., "HSV–1 Vector–Mediated Gene Transfer of the Human Nerve Growth Factor Receptor p75$^{hNGFR}$ Defines High–Affinity NGF Binding," *The Journal of Neuroscience,* 13(3):941–951, Mar. 1993.
Beattie et al., "Experimental Spinal Cord Injury," *Pharmacological Approaches to the Treatment of Brain and Spinal Cord Injury,* 43–74, Plenum Press, New York and London.
Breakefield and DeLuca, "Herpes Simplex Virus for Gene Delivery to Neurons," *The New Biologist,* 3(3):203–218, Mar. 1991.
Clapp, "Somatic Gene Therapy into Hematopoietic Cells," *Clinics in Perinatology,* 20(1):155–168, Mar. 1993.
Coune, "Liposome as Drug Delivery System in the Treatment of Infectious Diseases, Potential Applications and Clinical Experience," *Infection,* 16:141–147, 1988.
Culver et al., "In Vivo Gene Transfer with Retroviral Vector–Producer Cells for Treatment of Experimental Brain Tumors," *Science,* 256(1550–1552, Jun. 1992.
Dixon et al., "A Controlled Cortical Impact Model of Traumatic Brain Injury in the Rat," *Journal of Neuroscience Methods,* 39:253–262, 1991.
Fineman et al., "Concussive Brain Injury is Associated with a Prolonged Accumulation of Calcium: a $^{45}$Ca Autoradiographic Study," *Brain Research,* 624:94–102, 1993.
Friedmann, "Gene Therapy—a New Kind of Medicine," *Tibtech,* 11:156–159, May 1993.
Ghosh et al., "Requirement for BDNF in Activity–Dependent Survival of Cortical Neurons," *Science,* 263:1618–1623, Mar. 1994.
Hall et al., "Biochemistry and Pharmacology of Lipis Antioxidants in Acute Brain and Spinal Cord Injury," *Journal of Neurotrauma,* 9(2):S425–442, 1992.
Hayes et al., "Neurotransmitter–Mediated Mechanisms of Traumatic Brain Injury: Acetylcholine and Exictatory Amino Acids," *Journal of Neurotrauma,* 9(1):S173–187, 1992.
Imaizumi et al., "Liposome–Entrapped Superoxide Dismutase Reduces Cerebral Infarction in Cerebral Infarction in Cerebral Ischemia in Rats," *Stroke,* 21(9):1312–1317, Sep. 1990.
Imaizumi et al., "Liposome–Entrapped Superoxide Dismutase Ameliorates Infarct Volume in Focal Cerebral Ischaemia," *Acta Neurochirurgica,* 51:236–238, 1990.

(List continued on next page.)

*Primary Examiner*—Jasemine C. Chambers
*Assistant Examiner*—Jill D. Schmuck
*Attorney, Agent, or Firm*—Robert W. Strozier; J. M. (Mark) Gilbreth; Gilbreth & Strozier, P.C.

[57] ABSTRACT

Disclosed are methods for use in transferring nucleic acids into central nervous system cells in vivo and in vitro and/or for stimulating central nervous system cells. Neurotrophic genes are shown to stimulate neurofilament cells and to promote nerve cell growth, repair and regeneration in vivo. Gene transfer protocols are disclosed for use in transferring various nucleic acid materials into central nervous system cells, as may be used in treating various pathologies of the brain and spinal cord.

27 Claims, 15 Drawing Sheets

OTHER PUBLICATIONS

Johnson et al., "Degradation of Microtubule–Associated Protein 2 and Brain Spectrin by Calpain: A Comparative Study," *Journal of Neurochemistry,* 56(5):1630–1638, 1991.

Kaku et al., "Alterations of a 200 kDa Neurofilament in the Rat Hippocampus after Forebrain Ischemia," *Journal of Cerebral Blood Flow and Metabolism,* 13:402–408, 1993.

Kawaja et al., Somatic Gene Transfer of Nerve Growth Factor Promotes the Survival of Axotomized Septal Neurons and the Regeneration of Their Axons in Adult Rats, *The Journal of Neuroscience,* 12(7):2849–2864, Jul. 1992.

Li et al., "Gene Transfer in Primary Cultures of Human Hepatocytes," *In Vitro Cell. Dev. Biol.,* 28A:373–375, May 1992.

Mori and Fukatsu, "Anticonvulsant Effect of DN–1417, a Derivative of Thyrotropin–Releasing Hormone, and Liposome–Entrapped DN–1417, on Amygdaloid–Kindled Rats," *Epilepsia,* 33(6):994–1000, 1992.

Nable et al., "Gene Transfer In Vivo with DNA–Liposome Complexes: Lack of Autoimmunity and Gonadal Localization," *Human Gene Therapy,* 3:649–656, 1992.

Nistico et al., "NGF Restores Decrease in Catalase Activity and Increases Superoxide Dismutase and Glutathione Peroxidase Activity in the Brain of Aged Rats," *Free Radical Biology & Medicine,* 12:177–181, 1992.

Ono et al., "Plasmid DNAs Directly Injected Into Mouse Brain with Lipofectin can be Incorporated and Expressed by Brain Cells," *Neuroscience Letters,* 117:259–263, 1990.

Phillips et al., "BDNF mRNA is Decreased in the Hippocampus of Individuals with Alzheimer's Disease,"0 *Neuron,* 7:695–702, Nov. 1991.

Roessler and Davidson, "Direct Plasmid Mediated Transfection of Adult Murine Brain Cells In Vivo Using Cationic Liposomes," *Neuroscience Letters,* 167:5–10, 1994.

Sampath et al., "Effects of Nerve Growth Factor on Glutathione Peroxidase and Catalase in PC12 Cell," *Journal of Neurochemistry,* 62(6):2476–1479, 1994.

Taft et al., "Microtubule–Associated Protein 2 Levels of Decrease in Hippocampus Following Traumatic Brain Injury," *Journal of Neurotrauma,* 9(3):281–290, 1992.

Taft et al., "Hypothermia Attenuates the Loss of Hippocampal Microtubule–Associated Protein 2 (MAP2) Following Traumatic Brain Injury," *Journal of Cerebral Blood Flow and Metabolism,* 13:796–802, 1993.

Tomita et al., "Direct in vivo Gene Introduction into Rat Kidney," Nippon–Rinsho 50(12):2874–2878, 1992.

Wagner et al., "Influenza Virus Hemagglutinin HA–2 N–terminal Fusogenic Peptides Augment Gene Transfer by Transferrin–Polylysine–DNA Complexes: Toward a Synthetic Virus–Like Gene–Transfer Vehicle," *Proc. natl. Acad. Sci. USA,* 89:7934–7938, Sep. 1992.

Whitson et al., "Controlled Cortical Impact Injury Alters Amyloid Protein Precursor Levels in Rat Hippocampus and Cortex," *J. Neurotrama Abst.,* 1994.

Williamson, "From genome mapping to gene therapy," *Tibtech,* 11:159–161, May 1993.

Yang et al., "In vivo and In Vitro Gene Transfer to Mammalian Somatic Cells by Particle Bombardment," *Proc. Natl. Acad. Sci. USA,* 87:9568–9572, Dec. 1990.

Yang et al., "Alterations of Protein Kinase C in Rat Hippocampus Following Traumatic Brain Injury," *Journal of Neurotrauma,* 10(3):287–295, 1993.

Yang et al., "Sustained Expression of Functional Nerve Growth Factor in Primary Septo–Hippocampal Cell Cultures by Liposome–Mediated Gene Transfer," *Neuroscience Letters,* 00:1–4, 1994.

Yang et al., "Temporal and Regional Profile of C–Fos mRNA Expression after Critical Impact Injury in Rat Brain," *Trauma: Miscellaneous* 1, 1880.

Yang et al., "Optimizing Liposome–Mediated Gene Transfer in Primary Rat Septo–Hippocampal Cell Cultures," *Neuroscience Letters,* 00:1–4, 1994.

1:1 TRANSFECTION RATIO

1:5 TRANSFECTION RATIO

DARK FIELD

BRIGHT FIELD

LIPOSOMES

1:3 TRANSFECTION RATIO

HIGH MAGNIFICATION

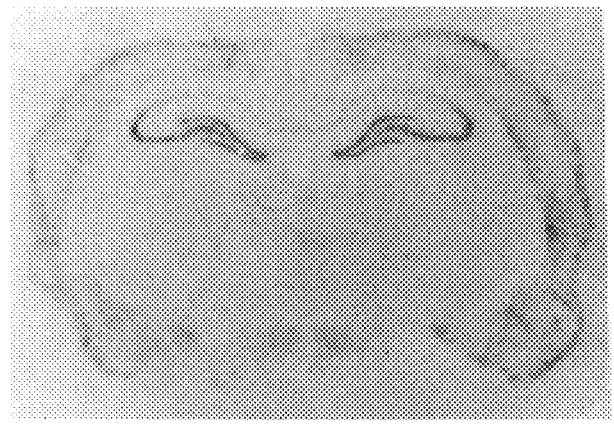
Fig. 7A  SHAM INJURY
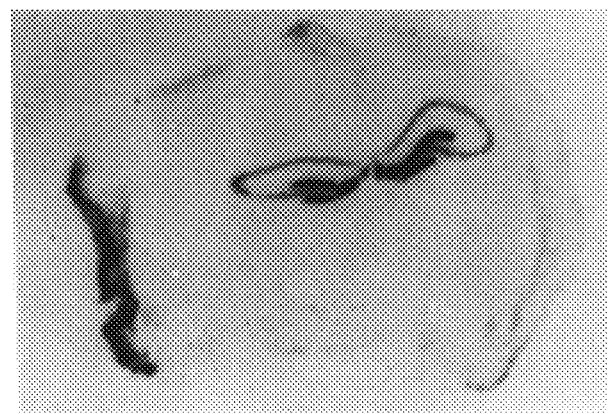
Fig. 7B  3 HOURS
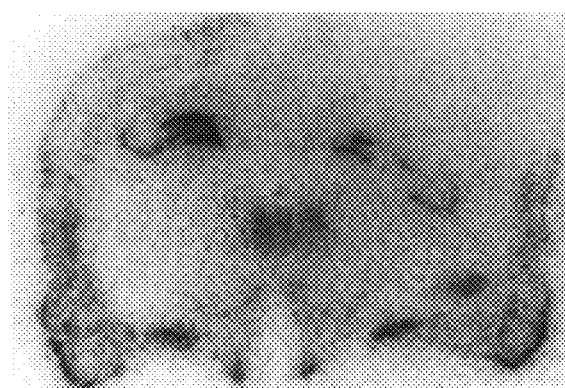
Fig. 7C  1 DAY

DARK FIELD

BRIGHT FIELD

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:1:

GCAAACATGT CTATGAGGGT                                                   20

(2) INFORMATION FOR SEQ ID NO:2:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:2:

GGTCAGTGTA CATACACAGG                                                   20

(2) INFORMATION FOR SEQ ID NO:3:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

GGCATGCTGG ACCCAAGCTC                                                   20

(2) INFORMATION FOR SEQ ID NO:4:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

GCGCTTGCTC CGGTGAGTCC                                                   20

(2) INFORMATION FOR SEQ ID NO:5:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

```
CCTTCCTGGG CATGGAGTCC TG                                              22
```

(2) INFORMATION FOR SEQ ID NO:6:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

```
GGAGCAATGA TCTTGATCTT C                                               21
```

LIPOSOME-MEDIATED TRANSFECTION OF CENTRAL NERVOUS SYSTEM CELLS

BACKGROUND OF THE INVENTION

The United States government has certain rights in the present invention pursuant to Grants P01 NS3199801 and NS21458 from the National Institutes of Health.

BACKGROUND OF THE INVENTION

A. Field of the Invention

The present invention relates generally to the field of molecular biology. More particularly, certain embodiments concern the transfer of genetic material into central nervous system cells. In certain examples, the invention concerns the use of liposome-mediated delivery of nucleic acids encoding neurotrophic factors to stimulate nervous system cell repair and regeneration. Rescue of neurofilament protein following traumatic brain injury (TBI) in vivo has been demonstrated.

B. Description of the Related Art

1. Neurotrophins Play Important Role in Cortical Injury Recovery

Brief depolarization of primary septo-hippocampal cell cultures can produce significant losses of neurofilament proteins. Studies have indicated that brain-derived neurotrophic factor (BDNF) increases neurofilaments in hippocampal cell cultures (Yip et al., 1993) and increases survival of cortical neurons (Ghosh et al., 1994).

Several articles have reported attempted treatments for treating traumatic brain injury. Exogenous supplementation of NGF has been reported to spare neurons from death and degeneration following injury (Hafti, 1986; Kromer, 1987; Montero and Hafti, 1988; Williams et al., 1986) and to increase choline acetyl transferase (CHAT) activity (Rylett et al., 1993; Williams and Rylett, 1990).

NGF prevents degeneration of septal cholinergic neurons following fimbria lesions or transfection (see e.g., Morse et al., 1993). NGF and BDNF increase survival of septal cholinergic neurons in vitro (see e.g., Alderson et al., 1990) and increase choline acetyl transferase (ChAT) activity both in vitro (see e.g., Alderson et al., 1990) and in intact animals (see e.g., Rylett et al., 1993).

Observations indicate that TBI can result in disturbances of cholinergic neurotransmission associated with impaired release of acetylcholine in the hippocampus (Dixon et al., 1993). In some cases, this disruption may cause nerve death, which may ultimately lead to brain dysfunction. However, the mechanism of cholinergic disturbance is not well-understood, and therapies addressing this abnormality in vivo have not been reported.

2. NGF and BDNF Expression in the Hippocampus

NGF and BDNF are members of the neurotrophin gene family, as are neurotrophin-3, and neurotrophins-4/5 (NT-3, NT-4/5). All are expressed in brain (for review, see Lindsay, 1993). During development in the adult rat brain BDNF and NGF mRNA are particularly abundant in the hippocampus (Maisonpierre et al., 1990b; Ernfors et al., 1990), a region which is preferentially vulnerable to TBI (Hayes et al., 1992; Olenik et al., 1988).

3. BDNF and NGF Blunt Free Radical Damage

Formation of free radicals and subsequent lipid peroxidation may contribute to TBI (Chan, 1992; Hall et al., 1992). Giving NGF to adult rats protects their sympathetic ganglia from 6-hydroxydopamine toxicity, a free radical generator (Johnnson, 1980). Furthermore, in adult rats, long-term NGF administration increases the activity of antioxidant enzymes in cortex (Nistico et al., 1992). Protection by NGF in cultures of PC-12 cells is associated with specific increases in catalase activity and glutathione levels due to stimulation of glutathione redox reactions and synthesis (see e.g., Sampath et al., 1993).

4. BDNF and NGF Initiate Cytoskeleton Repair

NGF has been shown to initiate and maintain neurite outgrowth in rat pheochromocytoma (PC12) cells (Greene and Tischler, 1982), and is associated with increased levels of $\beta$-tubulin (see e.g., Teng and Greene, 1993). BDNF has been shown to increase in vitro levels of neurofilament in hippocampal cell cultures (Yip et al., 1993). However, the role of these two growth factors in cytoskeletal stabilization in vivo had not been determined.

5. BDNF and NGF Are Involved in Neurodegenerative Disease

TBI is a risk factor for Alzheimer's disease (Mortimer et al., 1991), and in some cases, is also associated with diffuse deposition of $\beta/A_4$ protein (Roberts et al., 1991; Clinton et al., 1991), the amyloidogenic protein of Alzheimer's disease. Furthermore, in Alzheimer's disease in situ hybridization reveals significant decreases in BDNF mRNA (Phillips et al., 1991). In aged rats, NGF increases high affinity choline transport (Williams et al., 1990), stimulates Ach release (Rylett et al., 1993) and also improves the performance of age-impaired rats in spatial memory tasks (Fischer et al., 1987).

6. BDNF and NGF Expression After CNS Injury is Only Transient

Although various injuries to the CNS up-regulate the production of neurotrophins and increase BDNF and NGF mRNA in the hippocampus (Yang et al., 1993), in most injuries, production of neurotrophins is not sustained long enough to promote recovery. In TBI, prominent up-regulation of BDNF mRNA occurs in the hippocampus, but only transiently, from 1 h to 6 h after injury (Yang et al., 1993), and therefore levels of neurotrophins are not present in substantial levels to effect cytoskeletal (e.g., neurofilament) rescue.

7. Providing Neurotrophins to CNS Cells is Desirable Following TBI

Many different approaches have been contemplated to deliver exogenous neurotrophins to the nervous system of mammals (Hafti, 1986; Kromer, 1987; Montero and Hafti, 1988; Williams et al., 1986), although significant limitations imposed by protein degradation and by the blood-brain barrier have restricted the clinical utility of these approaches (Barinega, 1994).

Unfortunately, even though exogenous growth factors can be delivered within the brain by means of mini-osmotic pumps that release small amounts of neurotrophin into the ventricular cavity or directly into the parenchyma (Hafti, 1986; Williams et al., 1986; Kromer, 1987; Montero and Hafti, 1988), pumps must be mechanically regulated, and often can fail. This method is particularly expensive and inconvenient, since the stored growth factors in the pump reservoir diminish in activity over time, and fresh amounts of the neurotrophin must be constantly added.

Many drawbacks are also associated with these types of treatment protocols, not the least of which is the expensive and time-consuming purification of the recombinant proteins from their host cells (Rylett et al., 1993; Morse et al., 1993). Also, polypeptides, once administered to an animal are more unstable than is generally desired for a therapeutic agent, and they are susceptible to proteolytic attack. Furthermore, the administration of recombinant proteins can initiate various inhibitive or otherwise harmful immune responses.

8. Focal Delivery of Neurotrophins

Investigators studying central nervous system injury have long recognized that changes in specific proteins may be important determinants of pathological responses to injury and recovery of function of the injured brain. Gene transfer has emerged as a potential way to introduce neurotrophins into CNS cells and tissues (Friedmann and Ginnah, 1993). Methods currently used to introduce genes into localized regions of the nervous system through stereotactic injection include retroviral vectors, herpes virus vectors, adenoviral vectors and grafted cells. Grafted cells have been most extensively examined for growth factor production.

Studies grafting cells in brain capable of producing growth factors have employed mouse sarcoma cells, male mouse submaxillary gland cells (Levi-Montalcini and Cohen, 1960; Caramia et al., 1962) and sciatic nerve cells (Richardson and Ebendal, 1982) or alternatively, in cell culture followed by implantation within the brain (Gage et al., 1987). Despite limited success with several different cell types, including primary fibroblasts (Kawaja et al., 1992), astrocytes and immortalized cell lines (Rosenberg et al., 1988; Wolf et al., 1988) grafts remain only a temporary solution, since most will eventually be rejected.

Although retroviral vectors are considered the most efficient vectors for stable gene transfer into mitotic mammalian cells and have been widely used in CNS cancer gene therapy (Yamada et al., 1992; Ram et al., 1993; Culver et al., 1992), they are unsuitable for post-mitotic CNS cells, since with the exception of some lentiviruses, retroviruses can integrate only into chromosomes of dividing cells. Another significant limitation of retroviral vectors is their maximum insert capacity of 5–7 kb (Gelinas and Teman, 1986).

Two methods using viral vectors have been described: 1) Herpes Simplex virus, and 2) adenovirus-mediated delivery systems. Unfortunately, however, neither are suitable for treatment of TBI. Although Herpes virus is able to infect post-mitotic cells and can be taken up anywhere along the cell surface (Breakefield and DeLuca, 1991; Lycke et al., 1988), its toxicity to nervous cells (Johnson et al., 1992) and its disruption of normal neuronal architecture (Huang et al., 1992) make it unsuitable for treatment of TBI and CNS cells.

Replication-deficient adenoviral vectors have also been used to infect rat CNS cells in vitro and in vivo, since these DNA viruses are able to infect post-mitotic cells (le Gal La Salle et al., 1993), but unfortunately, they do not integrate efficiently into the nuclear DNA of the recipient cells, gene expression occurs only transiently, often in an unpredictable manner (Graham and Prevec, 1991; Horwitz, 1990). Further limiting these methods in the treatment of TBI is their limited transfection into neural cells, and the pathogenicity and limited duration of gene expression of these vectors.

Several groups have investigated the possibility of using liposomes as a means of mediating delivery of genetic information into nervous system cells in vitro, but unfortunately these methods were disappointing. For example, using the E. coli β-Gal reporter gene in liposome-mediated transfection of low density cultures of rat hippocampal neurons, the transfection efficiency was less than 1% of the whole cell population, and the small fraction of transfected cells was mostly neuronal (Drazba and Ralston, 1993).

Likewise, an ex vivo method employing cationic liposomes to transfect primary rodent neuronal cell cultures with a gene encoding β-Gal (Ono et al., 1990) showed only limited success, when the cell types which incorporated and expressed the injected cDNA were not delineated.

9. Deficiencies in the Prior Art

A method of treating a variety of central nervous system pathologies through manipulations of specific trophic and/or toxic proteins would have important therapeutic potential. Increasing expression of trophic factors which have been shown to enhance recovery of function following trauma to the brain and spinal cord would be particularly desirable. More than 500,000 patients annually are hospitalized for traumatic brain injury. More than 10,000 patients are treated for spinal cord injury and 750,000 patients for stroke. Neurodegenerative diseases, organically-based psychological disorders and chronic pain are all widely recognized major health problems in the United States. The presence of the blood-brain barrier significantly confounds the choice of routes for administration of neurotrophins.

It is clear, therefore, that a new method capable of promoting nervous system cell repair and regeneration in vivo would represent a significant scientific and medical advance with immediate benefits to a large number of patients. A method readily adaptable for use with a variety of growth factors and other genes would be particularly advantageous. Rescue of neurofilament loss due to TBI by increasing the availability of neurotrophins both ex vivo and in vivo would represent a significant improvement in the treatment of central nervous system injury.

SUMMARY OF THE INVENTION

The present invention overcomes one or more of these and other drawbacks inherent in the prior art by providing novel methods for use in transferring nucleic acids into post-mitotic nervous system cells and tissues, and for promoting nervous system cell repair and regeneration. Certain embodiments of the invention rest, generally, with the inventors' surprising finding that nucleic acids can be effectively transferred to post-mitotic cells by liposome-mediated transfection protocols both in vivo and ex vivo. Moreover, in certain embodiments, the transfer of a neurotrophic gene stimulates nervous system cell repair in an animal.

The invention, in general terms, thus concerns methods for transferring a nucleic acid segment into neural cells or tissues. The methods of the invention generally comprise contacting neural cells or tissues with a composition comprising a nucleic acid segment in a manner effective to transfer the nucleic acid segment into the cells.

Alternatively, the neural cells may be located within a central nervous system (CNS) tissue site of an animal, when the nucleic acid composition would be applied to the site in order to effect, or promote, nucleic acid transfer into CNS cells in vivo. In transferring nucleic acids into CNS cells within an animal, a preferred method involves first adding the genetic material to a liposome complex and then using the liposome-DNA complex to transfect an appropriate tissue site within the animal.

An extremely wide variety of genetic material can be transferred to CNS cells or tissues using the compositions and methods of the invention. For example, the nucleic acid segment may be DNA (double or single-stranded) or RNA (e.g., mRNA, tRNA, rRNA); it may also be a "coding segment", i.e., one that encodes a protein or polypeptide, or it may be an antisense nucleic acid molecule, such as antisense RNA that may function to disrupt gene expression. The nucleic acid segments may thus be genomic sequences, including exons or introns alone or exons and introns, or coding cDNA regions, or in fact any construct that one desires to transfer to a CNS cell or tissue.

Suitable nucleic acid segments may also be in virtually any form, such as naked DNA or RNA, including linear nucleic acid molecules and plasmids; functional inserts within the genomes of various recombinant viruses, including viruses with DNA genomes and retroviruses; and any form of nucleic acid segment, plasmid or virus associated with a gold particle which may be employed in connection with the gene gun technology.

The invention may be employed to promote expression of a desired gene in CNS cells or tissues and to impart a particular desired phenotype to the cells. This expression could be increased expression of a gene that is normally expressed (i.e., "over-expression"), or it could be used to express a gene that is not normally associated with CNS cells in their natural environment. Alternatively, the invention may be used to suppress the expression of a gene that is naturally expressed in such cells and tissues, and again, to change or alter the phenotype. Gene suppression may be a way of expressing a gene that encodes a protein that exerts a down-regulatory function, or it may utilize antisense technology.

1. Central Nervous System Cells and Tissues

In certain embodiments, this invention provides advantageous methods for using genes to stimulate CNS cells. As used herein, the term "CNS cells" refers to any or all of those cells that have the capacity to ultimately form, or contribute to the formation of, central nervous system tissue. This includes various cells in different stages of differentiation, such as, for example, developmentally different fetal and adult neural cells, as well as neurons, astroglia, microglia, and oligodendrocytes, and the like. CNS cells also include cells that have been isolated and manipulated in vitro, e.g., subjected to stimulation with agents such as cytokines or growth factors or even genetically engineered cells. The particular type or types of CNS cells that are stimulated using the methods and compositions of the invention are not important, so long as the cells are stimulated in such a way that they are activated and, in the context of in vivo embodiments, ultimately give rise to CNS cells and tissue. CNS cells may also be isolated from animal or human tissues and maintained in an in vitro environment. Isolated cells may be stimulated using the methods and compositions disclosed herein and, if desired, be returned to an appropriate site in an animal where CNS cell repair is to be stimulated. In such cases, the nucleic-acid containing cells would themselves be a form of therapeutic agent. Such ex vivo protocols are well known to those of skill in the art.

In important embodiments of the invention, the CNS cells and tissues will be those cells and tissues that may be damaged and that one desires to treat. Accordingly, in treatment embodiments, there is no difficulty associated with the identification of suitable target cells to which the present therapeutic compositions should be applied. All that is required in such cases is to obtain an appropriate stimulatory composition, as disclosed herein, and contact the site of the injury or defect with the composition. The nature of this biological environment is such that the appropriate cells will become activated in the absence of any further targeting or cellular identification by the practitioner.

Certain methods of the invention involve, generally, contacting CNS cells with a composition comprising one or more neurotrophic genes (with or without additional genes, proteins or other biomolecules) so as to promote expression of said gene in said cells. As outlined above, the cells may be contacted in vitro or in vivo. This is achieved, in the most direct manner, by simply obtaining a functional neurotrophic gene construct and applying the construct to the cells. The inventors surprisingly found that there are no particular molecular biological modifications that need to be performed in order to promote effective expression of the gene in CNS cells. Contacting the cells with a liposome complex containing a suitable DNA molecule, e.g., a linear DNA molecule, or DNA in the form of a plasmid or other recombinant vector, that contains the gene of interest under the control of a promoter, along with the appropriate termination signals, is sufficient to result in uptake and expression of the DNA, with no further steps being necessary.

2. Neurotrophic Genes

As used herein, the term "neurotrophic gene" is used to refer to a gene or DNA coding region that encodes a protein, polypeptide or peptide that is capable of promoting, or assisting in the promotion of, nerve cell formation, or one that increases the rate of primary nerve cell growth or healing (or even a gene that increases the rate of neurofilament tissue growth or healing). The terms promoting, inducing and stimulating are used interchangeably throughout this text to refer to direct or indirect processes that ultimately result in the formation of new CNS tissue or in an increased rate of CNS cell repair. Thus, a neurotrophic gene is a gene that, when expressed, causes the phenotype of a cell to change so that the cell either differentiates, stimulates other cells to differentiate, attracts CNS-forming cells, or otherwise functions in a manner that ultimately gives rise to new CNS tissue.

A variety of neurotrophic genes are now known, all of which are suitable for use in connection with the present invention. Neurotrophic genes and the proteins that they encode include, for example, BDNF, NGF, fibroblast growth factor (FGF), insulin-like growth factor, glial cell line-derived neurotrophic factor, ciliary neurotrophic factor, endothelial growth factor (EGF); chemotactic or adhesive peptides or polypeptides; morphogenetic proteins; and even growth factor receptor genes. Any of the above or other related genes, or DNA segments encoding the active portions of such proteins, may be used in the novel methods of the present invention.

As known to those of skill in the art, the original source of a recombinant gene or DNA segment to be used in a therapeutic regimen need not be of the same species as the animal to be treated. In this regard, it is contemplated that any recombinant growth factor (GF) or neurotrophic gene may be employed to promote CNS cell repair or regeneration in a human subject or an animal, such as, e.g., a horse. Particularly preferred genes are those from human. However, since the sequence homology for genes encoding nerve growth factors is highly-conserved across species lines, rodent and bovine species may also be contemplated as sources, in that such genes and DNA segments are readily available, with the human or rodent forms of the gene being most preferred for use in human treatment regimens. Recombinant proteins and polypeptides encoded by isolated DNA segments and genes are often referred to with the prefix "r" for recombinant and "rh" for recombinant human. As such, DNA segments encoding rGFs, such as rhNGF or rhBDNF, etc. are contemplated to be particularly useful in connection with this invention. Any recombinant neurotrophic gene would likewise be very useful with the methods of the invention.

The definition of a "GF gene", as used herein, is a gene that hybridizes, under relatively stringent hybridization conditions (see, e.g., Maniatis et al., 1982), to DNA sequences presently known to include GF gene sequences.

The definition of a "neurotrophic gene", as used herein, is a gene that hybridizes, under relatively stringent hybridization conditions (see, e.g., Maniatis et al., 1982, Molecular Cloning: A Laboratory Manual, Cold Spring Harbor Laboratory), to DNA sequences presently known to include neurotrophic gene sequences.

To prepare a neurotrophic gene segment or cDNA one may follow the teachings disclosed herein and also the teachings of any of patents or scientific documents specifically referenced herein. One may obtain a hGF or neurotrophic gene DNA segment using molecular biological techniques, such as polymerase chain reaction (PCR™) or screening a cDNA or genomic library, using primers or probes with sequences based on the above nucleotide sequence. The practice of such techniques is a routine matter for those of skill in the art, as taught in various scientific articles, such as Sambrook et al. (1989), incorporated herein by reference. Certain documents further particularly describe suitable mammalian expression vectors, e.g., U.S. Pat. No. 5,168,050, incorporated herein by reference. Neurotrophic genes and DNA segments that are particularly preferred for use in certain aspects of the present methods are the NGF and BDNF genes.

It is also contemplated that one may clone further genes or cDNAs that encode a growth factor or neurotrophic protein or polypeptide. The techniques for cloning DNA molecules, i.e., obtaining a specific coding sequence from a DNA library that is distinct from other portions of DNA, are well known in the art. This can be achieved by, for example, screening an appropriate DNA library which relates to the cloning of a CNS healing gene. The screening procedure may be based on the hybridization of oligonucleotide probes, designed from a consideration of portions of the amino acid sequence of known DNA sequences encoding related neurotrophic proteins. The operation of such screening protocols are well known to those of skill in the art and are described in detail in the scientific literature, for example, in Sambrook et al. (1989), incorporated herein by reference.

Techniques for introducing changes in nucleotide sequences that are designed to alter the functional properties of the encoded proteins or polypeptides are well known in the art, e.g., U.S. Pat. No. 4,518,584, incorporated herein by reference, which techniques are also described in further detail herein. Such modifications include the deletion, insertion or substitution of bases, and thus, changes in the amino acid sequence. Changes may be made to increase the neurotrophic activity of a protein, to increase its biological stability or half-life, to change its glycosylation pattern, and the like. All such modifications to the nucleotide sequences are encompassed by this invention.

It will, of course, be understood that one or more than one neurotrophic gene may be used in the methods and compositions of the invention. The nucleic acid delivery methods may thus entail the administration of one, two, three, or more, neurotrophic genes. The maximum number of genes that may be applied is limited only by practical considerations, such as the effort involved in simultaneously preparing a large number of gene constructs or even the possibility of eliciting an adverse cytotoxic effect. The particular combination of genes may be two or more distinct GF genes; or it may be such that a GF gene is combined with another neurotrophic gene and/or another protein such as a cytoskeletal protein, cofactor or other biomolecule; a hormone or growth factor gene may even be combined with a gene encoding a cell surface receptor capable of interacting with the polypeptide product of the first gene.

In using multiple genes, they may be combined on a single genetic construct under control of one or more promoters, or they may be prepared as separate constructs of the same or different types. Thus, an almost endless combination of different genes and genetic constructs may be employed. Certain gene combinations may be designed to, or their use may otherwise result in, achieving synergistic effects on cell stimulation and CNS cell growth, any and all such combinations are intended to fall within the scope of the present invention. Indeed, many synergistic effects have been described in the scientific literature, so that one of ordinary skill in the art would readily be able to identify likely synergistic gene combinations, or even gene-protein combinations.

It will also be understood that, if desired, the nucleic segment or gene could be administered in combination with further agents, such as, e.g., proteins or polypeptides or various pharmaceutically active agents. So long as a liposomal-genetic material complex forms part of the composition, there is virtually no limit to other components which may also be included, given that the additional agents do not cause a significant adverse effect upon contact with the target cells or tissues. The nucleic acids may thus be delivered along with various other agents as required in the particular instance.

3. Gene Constructs and DNA Segments

As used herein, the terms "gene" and "DNA segment" are both used to refer to a DNA molecule that has been isolated free of total genomic DNA of a particular species. Therefore, a gene or DNA segment encoding a neurotrophic gene refers to a DNA segment that contains sequences encoding a neurotrophic protein, but is isolated away from, or purified free from, total genomic DNA of the species from which the DNA is obtained. Included within the term "DNA segment", are DNA segments and smaller fragments of such segments, and also recombinant vectors, including, for example, plasmids, cosmids, phage, retroviruses, adenoviruses, and the like.

The term "gene" is used for simplicity to refer to a functional protein or peptide encoding unit. As will be understood by those in the art, this functional term includes both genomic sequences and cDNA sequences. "Isolated substantially away from other coding sequences" means that the gene of interest, in this case, a neurotrophic gene, forms the significant part of the coding region of the DNA segment, and that the DNA segment does not contain large portions of naturally-occurring coding DNA, such as large chromosomal fragments or other functional genes or cDNA coding regions. Of course, this refers to the DNA segment as originally isolated, and does not exclude genes or coding regions, such as sequences encoding leader peptides or targeting sequences, later added to the segment by the hand of man.

This invention provides novel ways in which to utilize various known neurotrophic DNA segments and recombinant vectors. As described above, many such vectors are readily available, one particular detailed example of a suitable vector for expression in mammalian cells is that described in U.S. Pat. No. 5,168,050, incorporated herein by reference. However, there is no requirement that a highly purified vector be used, so long as the coding segment employed encodes a neurotrophic protein and does not include any coding or regulatory sequences that would have an adverse effect on CNS cells. Therefore, it will also be understood that useful nucleic acid sequences may include additional residues, such as additional non-coding sequences flanking either of the 5' or 3' portions of the coding region or may include various internal sequences, i.e., introns, which are known to occur within genes.

After identifying an appropriate neurotrophic gene or DNA molecule, it may be inserted into any one of the many vectors currently known in the art, so that it will direct the expression and production of the neurotrophic protein when incorporated into a CNS cell. In a recombinant expression vector, the coding portion of the DNA segment is positioned under the control of a promoter. The promoter may be in the form of the promoter which is naturally associated with a neurotrophic gene, as may be obtained by isolating the 5' non-coding sequences located upstream of the coding segment or exon, for example, using recombinant cloning and/or PCR™ technology, in connection with the compositions disclosed herein.

In other embodiments, it is contemplated that certain advantages will be gained by positioning the coding DNA segment under the control of a recombinant, or heterologous, promoter. As used herein, a recombinant or heterologous promoter is intended to refer to a promoter that is not normally associated with a neurotrophic gene in its natural environment. Such promoters may include those normally associated with other neurotrophic genes, and/or promoters isolated from any other bacterial, viral, eukaryotic, or mammalian cell. Naturally, it will be important to employ a promoter that effectively directs the expression of the DNA segment in CNS cells.

The use of recombinant promoters to achieve protein expression is generally known to those of skill in the art of molecular biology, for example, see Sambrook et al. (1989). The promoters employed may be constitutive, or inducible, and can be used under the appropriate conditions to direct high level or regulated expression of the introduced DNA segment. The currently preferred promoters are those such as CMV, RSV LTR, the SV40 promoter alone, and the SV40 promoter in combination with the SV40 enhancer.

4. Liposome-Mediated Transfection

The therapeutic potential for liposome-mediated gene transfer in the injured CNS has been successfully demonstrated using the rodent model. Based on existing evidence which shows that the systemic injection of cDNA:cationic liposome complexes into animals is non-toxic (Stewart et al., 1992), the inventors have developed liposome-mediated gene transfer methods which demonstrate the surprising rescue of NF loss following TBI. These methods have proven to be superior to those methods of the prior art in the transfection of post-mitotic cells. Moreover, the present invention has demonstrated that liposome-mediated gene transfer can be used to effectively incorporate large gene inserts. Specific tissues and cell types may be targeted in vivo by the use of selected promoter-enhancer elements that are tissue and cell type specific, administration of the plasmid regionally into selected tissue compartments (Holt et al., 1990) and coupling a targeting ligand to the liposomal surface (Debs et al., 1987).

The present invention provides for a liposomal-mediated system for transfecting cDNA of neurotrophins into central nervous system cells, and represents the first successful use of cationic liposomes as efficient and clinically relevant vectors for the transfer of genes into cells of the central nervous system. Efficient transfection of genes may result in therapeutic levels of expression of neurotrophins and other proteins which could be useful in the treatment of a variety of central nervous system pathologies including mechanical injury to the brain and spinal cord, stroke, neurodegenerative diseases (e.g., Alzheimer's disease, Parkinson's disease), organically-mediated psychological disorders (e.g., depression, panic disorders) and chronic pain syndromes.

5. Methods of DNA Transfection

Technology for introduction of DNA into cells is well-known to those of skill in the art. Four general methods for delivering a gene into cells have been described: (1) chemical methods (Graham and VanDerEb, 1973); (2) physical methods such as microinjection (Capecchi, 1980), electroporation (Wong and Neumann, 1982; Fromm et al., 1985) and the gene gun (Yang et al., 1990); (3) viral vectors (Clapp, 1993; Danos and Heard, 1992; Eglitis and Anderson, 1988); and (4) receptor-mediated mechanisms (Wu et al., 1991; Curiel et al., 1991; Wagner et al., 1992).

Chemical and physical methods of DNA transfer are relatively inefficient processes and are not applicable to studies in which gene transfer needs to occur in a relatively high percentage of cells. Therefore, much effort has focused on developing viral vectors for gene transfer and on developing new compounds, such as liposomes, that would allow DNA transfer at relatively high efficiency. Important clinical disadvantages of viral vectors include the possibility of replication-competent virus production, immunological reactions and toxicity.

Liposomes have also been used successfully with a number of cell types that are normally resistant to transfection by other procedures including T cell suspensions, primary hepatocyte cultures and PC 12 cells (Chang and Brenner, 1988; Muller et al., 1990). In addition, liposomes are free of the DNA length constraints that are typical of viral-based delivery systems. Liposomes have been used effectively to introduce genes, drugs (Heath et al., 1986; Storm et al., 1988; Balazsovits et al., 1989), radiotherapeutic agents (Pikul et al., 1987), enzymes (Imaizumi et al., 1990; Imaizumi et al., 1990), viruses (Faller and Baltimore, 1984; Wilson et al., 1977; Wilson et al., 1979), transcription factors (Debs et al., 1990) and allosteric effectors (Nicolau et al., 1979) into a variety of cultured cell lines and animals. In addition, several successful clinical trails examining the effectiveness of liposome-mediated drug delivery have been completed (Lopez-Berestein et al., 1985; Coune, 1988). Furthermore, several studies suggest that the use of liposomes is not associated with autoimmune responses, toxicity or gonadal localization after systemic delivery (Nabel et al., 1992; Mori and Fukatsu, 1992).

Introduction of the liposome-cDNA transfection complex may be by injection, and may be systemic injections into peripheral arteries or veins, including the carotid or jugular vessels. Injection may also be directly into the central nervous system, either by intraventricular administration, or directly into the brain tissue itself. Such injection may be facilitated by the use of mini-osmotic pumps for long-duration infusion, or an intraparenchymal injection apparatus with ventricular cannuli or other intraparenchymal devices. In other embodiments, it may be desirable to introduce the liposome-cDNA complex directly into the spinal cord or surrounding epidural space. This is particularly important in the instance of spinal cord injury. In such cases, either direct injections into the spinal cord (intramedullary) or into the subarachnoid space would be desirable. In other cases, direct or indirect puncture of the epidural space may be desired. In the case of brain injury, or in circumstances where introduction of GFs into the brain is desirable, such injection may be made into the ventricle, the hippocampus, the cortex, or directly into the spinal cord.

6. Neurofilaments

Previous histopathologic examination of severe human TBI (Adams et al., 1983; Gennarelli et al., 1989) and animal cortical impact models (Dixon et al., 1991) have pointed to the prevalence of axonal damage as a feature of injury pathology. Diffuse axonal injury (DAI) is found in injured cortex and is characterized by the histopathologic observation of retraction bulbs caused by mechanical forces radiating from the cortical impact site. Retraction bulbs are characteristic of post-injury cortex but are rarely observed in injured hippocampi (Adams et al., 1983; Dautingy et al., 1988; Fineman et al., 1993; Troost et al., 1992). A similar distribution of NF protein changes has been observed in the present invention. Loss of NF68 and NF200 was found in cortical tissue (no hippocampal loss) and was predominant in the ipsilateral hemisphere. Thus, the regional distribution of TBI-induced NF protein loss was similar to that previously reported for axonal damage following TBI in human and animal cortical impact models (Adams et al., 1983; Dixon et al., 1991; Gennarelli et al., 1989; Yaghmai and Povlishock, 1992). In contrast to earlier qualitative work, these studies indicate that the overall effect of TBI on NF68 protein levels throughout the cortex is reduction, although site-specific increases of NF68 in retraction bulbs have been documented (Yaghmai and Povlishock, 1992).

The present invention departs from previous qualitative studies and demonstrates the effects of severe TBI on the levels of cytoskeletal proteins, which are primary components of axons and dendrites. The axonal damage observed following severe TBI is likely to be associated with an extensive and persistent loss of key neurofilament proteins. Further, the presence of low-MW NF68 breakdown products implicates TBI-induced proteolysis in the loss of NF protein.

A surprising aspect of the present invention is the presence of low MW immunopositive bands in injured samples associated with loss of the parent NF68 protein. These bands do not occur substantially in naive or sham-injured samples but appear prominently in 3 h, 1 day, and 7 days post-injury samples. These bands may represent NF68 breakdown products (BDPs) produced by the action of proteases on the parent NF68 protein, since prominent BDPs at MWs of 56 kDa and 52 kDa were observed in Western analyses. Interestingly, the action of the calcium-activated protease, calpain, on neurofilament protein produces immunopositive cleavage products of 57 kDa and 53 kDa. These NF68 BDPs have been observed in both in vivo and in vitro studies (Kamakura et al., 1985; Schlaepfer et al., 1984; Schlaepfer and Zimmerman, 1985a, 1985b). The fragments correspond to the amino terminal, alpha-helical domain common to all neurofilament proteins (NF68, NF150, NF200). Therefore, NF68 BDPs identified here may be fragments produced by cleavage of NF68, NF150, and/or NF200 (Schlaepfer et al., 1984; Schlaepfer and Zimmerman, 1985a, 1985b). Since the existing anti-NF200 monoclonal antibodies target the carboxyl terminal domain present in NF200 (and consequently do not recognize the low molecular weight BDPs containing the alpha-helical domain), other antibodies are required to determine the relative contribution of NF68, NF150, or NF200 to the low MW BDPs.

Although other proteases also produce immunopositive fragments, such as cathepsins B and D, trypsin, and alphachymotrypsin, the MWs of the proteolytic fragments were substantially lower and did not resemble the pattern observed in post-TBI (Chin et al., 1983; Kamakura et al., 1985; Nixon and Marotta, 1984). The BDPs observed in this study match very closely those produced by calpain-dependent proteolysis and suggest that calpain activation contributes to the loss of neurofilament protein observed post-injury. These breakdown products are of particular interest because they are believed to be involved in the maintenance of neurofilament metabolism (Schlaepfer et al., 1984; Schlaepfer and Zimmerman, 1985a, 1985b). Thus, the action of TBI may produce alterations of neurofilament function by two mechanisms: (1) by reduction of NF68 and NF200 protein levels and (2) by production of metabolically significant breakdown products.

Like other neuropathologic conditions, such as ischemia and protracted seizures, TBI pathology is produced, at least in part, by prolonged excitotoxicity and subsequent calcium influx, leading to a loss of intracellular calcium homeostasis. Under more severe TBI magnitudes, such as those experienced in cortical impact models, excitotoxic injury is accompanied by the presence of mechanical damage. Mechanical forces caused by injury can disrupt membrane integrity and, thereby, further contribute to intracellular calcium levels. The cascade of biochemical pathologic conditions that may occur under conditions of high intracellular calcium would include activation of calciumdependent proteases (Siman and Noszek, 1988). Significantly, lateral fluid percussion injury (a model of TBI that produces severe injury) causes higher levels of intracellular calcium in injured cortex than in the corresponding hippocampi (Fineman et al., 1993). These findings may explain the distribution of calpain-like BDPs in the cortex, where injury and calcium accumulation may be most severe, and its notable absence in the hippocampus.

An important aspect of the present invention is the use of two models of TBI which reproduce features of moderate diffuse TBI or more severe injury with focal tissue damage. This approach permits the study of liposome-mediated gene transfection across a clinically-relevant range of injury levels. Fluid percussion injury, a model of diffuse TBI, produces deficits in motor function and spatial memory performance in part by producing sublethal excitotoxic damage of neurons (Hayes et al., 1992). The hippocampus is preferentially vulnerable in this model (Lyeth et al., 1990). Several studies have documented that fluid percussion TBI does not produce cerebral ischemia (DeWitt et al., 1989), but sustained blood-brain barrier opening is observed (Jiang et al., 1992). Cortical impact, a model of severe TBI, produces focal contusions and more DAI than fluid percussion injury (Dixon et al., 1991). Excitotoxic injury processes also contribute to enduring behavioral deficits following cortical impact (Palmer et al., 1993).

A particular aspect of the present invention is the evidence provided which suggests NF proteolysis plays an important role in pre-necrotic axonal changes after TBI. The loss of NF68 and NF200 proteins, as well as the appearance of NF68 BDPs, strongly suggests the occurrence of pathologic proteolysis post-injury. Data describing NF protein loss secondary to calpain activation in models of spinal cord injury further support the protease hypothesis (Banik et al., 1992; Schlaepfer and Zimmerman, 1985a). Importantly, the observation of immunopositive NF68 BDPs in the cortical impact model complicates the interpretation of immunohistochemical data and could provide an alternate explanation for localized increases in NF68 immunoreactivity post-injury (Povlishock, 1993; Yaghmai and Povlishock, 1992). Increased NF68 antigenicity in immunohistochemical studies may represent BDPs of NF68, as well as NF150 and NF200.

In laboratory models of ischemia, NF protein loss has been demonstrated after focal ischemic damage (Inuzuka et al., 1990b), as well as after global ischemia in both rats (Kaku et al., 1993) and gerbils (Kamakura et al., 1985; Nakamura et al., 1992). Similarly, cytoskeletal damage caused by ischemia has been prevented by administration of antiproteolytic compounds (Arai et al., 1990, 1991; Inuzuka et al., 1990a; Lee et al., 1991).

Two related hypotheses have been proposed that address the mechanism of axonal damage and diffuse axonal injury following TBI (Balentine, 1985; Povlishock, 1993). The first postulate implicates primary disruption of NF, possibly associated with altered NF phosphorylation, as contributing to NF disassembly and localized increases in NF antigenicity found in retraction balls (Povlishock, 1993; Yaghmai and Povlishock, 1992). To date, no direct evidence exists for altered phosphorylation of NF after TBI. The second premise suggests that TBI activates calciumdependent proteases that cause subsequent NF disruption and proteolysis.

7. Traumatic Brain Injury

Axonal injury has long been thought to be a primary pathologic feature of traumatic brain injury (TBI). Animal models of severe TBI and human post-injury pathology demonstrate axonal damage (Gennarelli et al., Yaghmai and Povlishock, 1992). A central polemic in TBI investigation is the relative roles of structural determinants vs. concurrent biochemical derangements as the crucial pathologic events post-injury. In human studies, investigators have identified diffuse axonal injury (DAI) as the key pathologic feature responsible for the neurobehavioral deficits that accompany human TBI (Adams et al., 1983; Gennarelli et al., 1989).

Current studies investigating DAI after TBI have been predominantly pathomorphologic and qualitative in nature. Recent investigations of the role of NF68 in DAI pathology are a noteworthy exception (Yaghmai and Povlishock, 1992). Although axonal dysfunction may play an important role in TBI pathology, no causal relationship has been established between DAI and post-injury neurobehavioral deficits. In fact, numerous studies have revealed that functionally normal neurotransmission can be preserved in pathways that have suffered significant loss of fibers (Beattie et al., 1988; Sautter et al., 1991). Thus, a comprehensive quantitative assessment of cytoskeletal alterations would contribute to the understanding of DAI and its role in TBI pathology.

Rodent models of TBI cause neurobehavioral deficits, including motor and memory disturbances, that resemble those seen in human patients (Hamm et al., 1992; Lyeth et al., 1990). Little is known of the molecular events leading to post-injury pathology in these animal models. Recent laboratory studies have determined that TBI induces a significant decrease in the protein levels of key dendritic cytoskeletal elements (Taft et al., 1992, 1993), including microtubule-associated protein 2 (MAP2). Post-TBI excitotoxicity (Gorman et al., 1989; Hayes et al., 1992), loss of calcium homeostasis (Fineman et al., 1993) and pathologic activation of calcium-dependent proteases (Taft et al., 1992, 1993) (e.g., calpain) may be principal causes of cytoskeletal degradation. Although calpains are found in both axonal and dendritic environments (Perlmutter et al., 1988), previous examination of cytoskeletal pathology after TBI has focused on dendritic cytoskeletal elements (MAP2) (Taft et al., 1992, 1993). Neurofilament proteins (Kamakura et al., 1985; Schlaepfer et al., 1984; Schlaepfer and Zimmerman, 1985b), MAP2 (Johnson et al., 1991), spectrin (Siman et al., 1984), and other cytoskeletal proteins are substrates for calpain-dependent proteolysis.

Therapeutically relevant strategies for manipulating production of these proteins may ultimately have important implications for the treatment of TBI. TBI is associated with disturbances of the blood-brain barrier which may enhance delivery of transgenes by vectors that would otherwise have restricted access to the CNS. In contrast to neurodegenerative diseases, experimental TBI can produce relatively rapid changes in specific proteins, facilitating assessments of the effects of gene therapy on post-traumatic gene expression.

8. Neuronal Architecture

Neurofilament (NF) proteins are primary components of the neuronal cytoarchitecture, including axons and dendrites (Shaw, 1986). NFs consist of three separate protein elements collectively called the neurofilament triplet proteins (Hoffman and Lasek, 1975). These subunits have apparent molecular weights of 200 kDa (NF-H), 150 kDa (NF-M), and 68 kDa (NF-L) as estimated by gel electrophoresis (Dautingy et al., 1988). The 68-kDa subunit is an assembly protein found predominantly in the neurofilament core, and the 150-kDa and 200-kDa subunits are cross-linking proteins found in the connecting branches.

All NF triplet proteins exhibit significant sequence homology in the amino terminal, alpha helical domain. The 150-kDa and 200-kDa subunits possess highly repeating lysine-serine-proline (KSP) sequences, which are heavily phosphorylated and contribute to anomalous electrophoretic mobilities (Julien and Mushynski, 1982; Nixon and Sihang, 1991).

Neurofilament rescue refers to the prevention of neurofilament deterioration, and/or to the maintenance and/or promotion of neurofilament restoration and recovery. Such rescue may be accomplished by reducing the rate of neurofilament decrease following TBI or by enhancing and/or stimulating the rate of neurofilament protein production and nerve cell restoration.

The assembly of NF proteins results in the formation of neurofilaments of approximately 10 nm in diameter in the axon hillock that are transported down the axon. Although their function is primarily structural, NF proteins have been implicated in many disease processes, such as Alzheimer's disease (Sternberger et al., 1985; Ulrich et al., 1987), amyotrophic lateral sclerosis (Troost et al., 1982), and Pick's disease (Pietrini et al., 1993), and in neurologic insults, such as stroke (Arai et al., 1990, 19910; Inuzuka et al., 1990a, b; Kaku et al., 1993; Kudo et al., 1993; Lee et al., 1991; Nakamura et al., 1992).

BRIEF DESCRIPTION OF THE DRAWINGS

The drawings form part of the present specification and are included to further demonstrate certain aspects of the present invention. The invention may be better understood by reference to one or more of these drawings in combination with the detailed description of specific embodiments presented herein.

FIG. 7A. Autoradiograph of in situ hybridization analyses of expression of endogenous BDNF following sham injury. Analyses employed $^{33}$P-labeled RNA probe for BDNF.

FIG. 7B. Autoradiograph of in situ hybridization analyses of expression of endogenous BDNF three hours after cortical impact injury. Analyses employed $^{33}$P-labeled RNA probe for BDNF. Note prominent increase in expression of endogenous BDNF, especially in the region of the dorsal hippocampus, as compared to sham injury animal (FIG. 7A).

FIG. 7C. Autoradiograph of in situ hybridization analyses of expression of endogenous BDNF one day following cortical impact injury. Analyses employed $^{33}$P-labeled RNA probe for BDNF. Note prominent increase in expression of endogenous BDNF, especially in the region of the dorsal hippocampus. By one day following injury, expression of endogenous BDNF had returned approximately to control levels.

DETAILED DESCRIPTION OF THE PREFERRED EMBODIMENTS

Figure 1A:
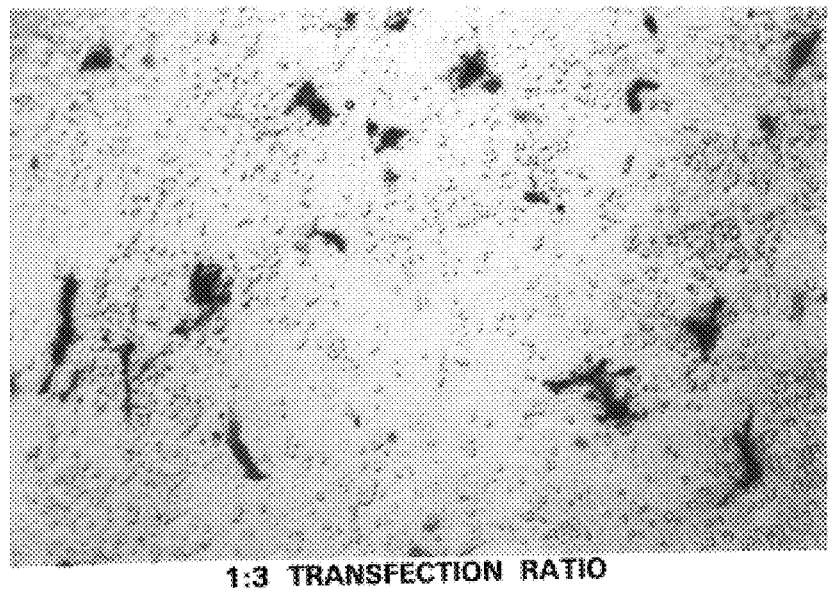
FIG. 1A. Photomicrograph showing X-Gal staining in septo-hippocampal cultures 48 hours after transfection with cDNA for the reporter gene, β-galactosidase. Varying ratios of cDNA to liposomes were overlaid onto rat hippocampal cells. Employing a 1:3 (DNA/liposome) transfection ratio, X-Gal staining was detected in cells having neuronal morphology. (Magnification: 110×).

The inventors have employed primary septo-hippocampal cell cultures to examine liposomal-mediated gene transfection in vitro, and have determined optimal ratios for transfection employing the β-galactosidase reporter gene. Transfection efficiency was significantly improved over the prior art results using liposomal-mediated systems in vitro (Kaech et al., 1993). RT-PCR analyses have confirmed increased expression of BDNF and NGF. Initial in situ hybridization analyses further confirmed successful transfection of BDNF cDNA in vitro. ELISA analyses have detected large increases in NGF protein after in vitro liposomal transfection. β-Gal has been used to study transfection following local injections of cDNA-liposome complexes in the region of the hippocampus. These studies also indicate successful liposomal mediated transfection in uninjured rats. In order to accurately assess the effects of gene transfection following trauma, in situ hybridization studies have been performed to characterize changes in endogenous NGF and BDNF after injury.

Liposome-mediated gene transfection of nerve growth factor (NGF) has been exploited in primary central nervous system cultures. RT-PCR analyses detected increased expression of NGF mRNA one day after liposome-mediated NGF gene transfection; ELISA studies detected large increases in NGF protein in cells and in culture medium after NGF gene transfection. Cells continued to secrete NGF into the medium for at least 2 weeks. NGF bioassays confirmed that the NGF secreted after gene transfection was biologically active.

In situ hybridization and immunohistochemistry have demonstrated in the present invention the successful expression of NGF and BDNF mRNA at various times after administration of cDNA-liposome complexes. Protein expression analyses as well as immunohistochemical analyses of neurotrophin receptors (p75$^{NGFR}$, p140$^{trkB}$) and bioactivity assay of NGF and BDNF have also demonstrated the presence of these growth factors in vitro and in vivo. Gene therapy has been employed to achieve therapeutically useful levels of expression of neurotrophins and other proteins in the traumatically injured brain. Experimental models of TBI have been used to facilitate the study of transfection of central nervous system cells.

1. Forty-fold Improvement in Transfection Efficiency

Studies employing the β-Gal reporter gene in CNS cell cultures further confirmed observations of other researchers that the concentrations of liposomes can influence the efficiency of transfection (Felgner et al., 1987). The differential transfection efficiencies in CNS cell cultures associated with varying concentrations of liposomes is consistent with the view that the higher the net positive charge of DNA-liposome complexes is, the better the interaction with the negatively charged cell membrane will be. However, overly high levels of liposomes can cause cell lysis. Without increasing liposome concentrations, increased amounts of DNA did not improve transfection efficiency.

The efficiency of the DOTMA and DOPE mediated pCMV/β-Gal transfection observed by the inventors in septo-hippocampal cell cultures (>1000 transfected cells per 16 mm well) exceeds by nearly forty-fold the previously reported transfection efficiency for β-Gal in hippocampal cultures employing the transfection reagents Transfectam and DOTAP (40–200 per 35mm well) (Kaech et al., 1993). The sustained expression of β-Gal for at least two weeks further suggests the potential therapeutic utility of liposomal mediated gene transfection in CNS injury and degeneration.

2. 1:3 is Optimum Ratio of cDNA:Liposomes for Transfection

β-Gal has been used as a reporter gene for examining factors influencing the efficiency of liposome-mediated gene transfection in central nervous system cell cultures. Results indicate that without increasing the amounts of DNA, increased liposome concentrations within certain limits enhanced transfection efficiency. However, higher liposome levels could produce cell lysis. Without increasing liposome concentrations, increased amounts of DNA did not improve transfection efficiency. Employing the optimal concentration (1 μg DNA/3 μl liposomes/well), β-Gal gene expression was sustained for at least two weeks after transfection in primary septo-hippocampal cultures.

Studies of liposome mediated gene transfection in septo-hippocampal cultures determined that a concentration of 1

μg DNA/3 μl liposomes/well (16-mm well) (or a ratio of 1:3) produced superior results, and this ratio was used to transfer the NGF gene to primary septo-hippocampal cell cultures. The purpose of these studies was to systematically examine if liposome-mediated NGF gene transfection could produce increased expression of NGF mRNA and protein. The biological activity of the NGF protein produced following transfection was also analyzed. Ratios of cDNA to liposomes were tested in the range of about 1:1 to about 1:9. Ratios of about 1:1 to about 1:5 were particularly preferred, with a ratio of about 1:3 being most preferred.

3. Successful Neurotrophin Transfection in Vitro and in Vivo

Gene transfection could result in increased expression of trophic proteins or decreased expression of toxic proteins. Routes of administration of liposomal-cDNA complexes could include direct delivery into the central nervous system (local, ventricular, and/or epidural injections) or systemic injections. Specific tissues and cell types could be targeted by several approaches. These include using promoter enhancer elements that are tissue and cell type specific, administration of the plasma regionally into selected tissue compartments as indicated above and coupling a targeting ligand to the liposomal surface.

4. BDNF and NGF Transfection Rescues Neurofilament Loss After TBI

A post-injury analysis of neurofilament proteins in the cortex and hippocampal tissue was performed. Lateral cortical impact injury resulting in severe TBI causes pronounced reduction in NF68 and NF200 levels that lasts for at least 2 weeks post-injury. Further, the presence of low molecular weight (MW) NF68 immunopositive bands of 52 kDa and 56 kDa may indicate the involvement of calpain-mediated proteolysis. The temporal and regional profiles of these changes could have profound implications for axonal and dendritic pathology after severe TBI.

Primary septo-hippocampal cell cultures have been employed to demonstrate the therapeutic potential of BDNF gene transfection in facilitating the recovery of neurofilament loss caused by depolarization injury. Employing a pUC19-based plasmid, rat BDNF cDNA was subcloned into a unique NotI site under the control of the CMV promoter to generate pBDNF. DNA for BDNF was complexed with liposomes and transfected into primary septo-hippocampal cell cultures one day after depolarization injury (6.0 min depolarization with 60 mM KCl and the presence of 2.8 mM $Ca^{++}$). Three days after depolarization injury, Western blot and immunohistochemical analyses detected significant loss (42%) of NF-M and NF-H proteins (Sternberger SMI 31 antibody) in untreated cultures. However, densitometric scanning of Western blot data indicated that BDNF transfection produced a two-fold increase in NF-M/NF-H three days following injury as compared to untreated cultures. Immunohistochemical studies also detected enhanced NF-M/NF-H immunolabeling in injured neurons following BDNF transfection as compared to untransfected, injured controls. Thus, BDNF gene transfection could be a useful therapeutic tool for blunting neurofilament loss associated with injury to central nervous system neurons.

5. Use of the Cytomegalovirus Promoter

When the gene remains extrachromosomal, as in liposomal mediated gene transfections, optimal levels of expression are likely to be achieved using viral promoters. Furthermore, viral promoters generally function in a broad range of cell types. The relative strengths of several commonly used viral promoters have been studied in different cell lines including primary cultures of rat mammary epithelial cells, NIH 3T3 (Thompson et al., 1993), primary rat and human hepatocytes (Fang et al., 1989; Li et al., 1992), human embryo fibroblasts (Giordano et al., 1991) and brain tumor cell lines (Dellig and Seliger, 1990). Studies indicate that the cytomegalovirus is a prudent initial choice of viral promoter. In primary cultures of human hepatocytes, the CMV promoter yields a higher transfection efficiency than RSV and SV40 (Li et al., 1992). RSV and CMV promoters were tested for activity are substantial in non-replicating cells: the efficiency of RSV promoter is not greater than background whereas the CMV promoter is very active. Furthermore, the CMV promoter exhibits two-fold greater activity in growing cells (Giordano et al., 1991). The CMV promoter also shows high activity in glioblastoma cell lines (Dellig and Seliger, 1990).

6. Immunocytochemistry of NGF and BDNF

RT-PCR and in situ hybridization techniques may be employed to determine the transfection efficiencies for NGF and BDNF. Autoradiographic and emulsion in situ hybridization techniques employ $^{33}P$-labeled mRNA probes for NGF and BDNF to provide information on the regional extent, cellular localization and persistence of increased mRNA. RT-PCR methods provide semiquantitative information on changes in mRNA. RT-PCR techniques are considerably more sensitive than Northern blots and are more robust to the effects of injury. RT-PCR has been reliably used to evaluate levels of NGF and BDNF mRNA in rodent brains (Giordano et al., 1992). In situ hybridization studies are important for development of appropriate dissection protocols for TR-PCR analyses in vivo, since, in vivo transfection will be restricted to specific areas of the brain.

A monoclonal antibody (clone 27/21) specific for rat and mouse β (2.5S) NGF that is also suitable for ELISA determinations of NGF proteins in brain tissue was used for protein assessment. An antibody for BDNF having considerable specificity has been reported (Denton et al., 1993), and Dr. Franz Hafti of Genentech, Inc. provided this antibody. Immunohistochemistry may be employed to describe regional changes in expression of NGF and BDNF protein. ELISA may be used to provide quantitative data on changes in neurotrophin protein levels.

Immunohistochemical analyses of neurotrophin receptors $p75^{NGFR}$, $p140^{trkA}$, $p145^{trkB}$ may be performed. Antibodies are made to synthetic peptide segments on the different receptors and allow determination of different tyrosine kinase receptors (TRKs) as well as differential staining of full and truncated versions of the different TRKs. Neurotrophins bind with equal affinity to a common low affinity neurotrophin receptor, $p75^{NGFR}$ whose function is likely to be stimulation of high affinity binding to trk receptors (Chao et al., 1993, Battleman et al., 1993).

The different neurotrophins also bind to different members of the trk family of membrane-spanning tyrosine kinase receptors, the signal transducing elements of the neurotrophins (Barker and Murphy, 1992). NGF binds specifically to $p140^{trkA}$. BDNF binds specifically to $p145^{trkB}$. NT-3 binds to both $p145^{trkB}$ and $p145^{trkC}$. Although there are claims that $p140^{trkA}$ by itself has high affinity NGF-binding properties, others report that both genes are required for high affinity NGF-binding activity (Chao et al., 1993, Battleman et al., 1993).

7. Biological Functional Equivalents

As mentioned above, modification and changes may be made in the structure of a neurotrophic gene and still obtain a functional molecule that encodes a protein or polypeptide with desirable characteristics. The following is a discussion based upon changing the amino acids of a protein to create an equivalent, or even an improved, second-generation molecule. The amino acid changes may be achieved by changing the codons of the DNA sequence, according to the following data (Table 1)

TABLE 1

| Amino Acids | | | Codons | | | | |
|---|---|---|---|---|---|---|---|
| Alanine | Ala | A | GCA | GCC | GCG | GCU | |
| Cysteine | Cys | C | UGC | UGU | | | |
| Aspartic acid | Asp | D | GAC | GAU | | | |
| Glutamic acid | Glu | E | GAA | GAG | | | |
| Phenylalanine | Phe | F | UUC | UUU | | | |
| Glycine | Gly | G | GGA | GGC | GGG | GGU | |
| Histidine | His | H | CAC | CAU | | | |
| Isoleucine | Ile | I | AUA | AUC | AUU | | |
| Lysine | Lys | K | AAA | AAG | | | |
| Leucine | Leu | L | UUA | UUG | CUA | CUC | CUG CUU |
| Methionine | Met | M | AUG | | | | |
| Asparagine | Asn | N | AAC | AAU | | | |
| Proline | Pro | P | CCA | CCC | CCG | CCU | |
| Glutamine | Gln | Q | CAA | CAG | | | |
| Arginine | Arg | R | AGA | AGG | CGA | CGC | CGG CGU |
| Serine | Ser | S | AGC | AGU | UCA | UCC | UCG UCU |
| Threonine | Thr | T | ACA | ACC | ACG | ACU | |
| Valine | Val | V | GUA | GUC | GUG | GUU | |
| Tryptophan | Trp | W | UGG | | | | |
| Tyrosine | Tyr | Y | UAC | UAU | | | |

For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated by the inventors that various changes may be made in the DNA sequences of neurotrophic genes without appreciable loss of their biological utility or activity.

In making such changes, the hydropathic index of amino acids may be considered. The importance of the hydropathic amino acid index in conferring interactive biologic function on a protein is generally understood in the art (Kyte & Doolittle, 1982, incorporate herein by reference). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of their hydrophobicity and charge characteristics (Kyte & Doolittle, 1982), these are: Isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine *−0.5); cysteine (−1.0); methionine (−1.3); valine (−1.5); leucine (−1.8); isoleucine (−1.8); tyrosine (−2.3); phenylalanine (−2.5); tryptophan (−3.4).

It is understood that an amino acid can be substituted for another having a similar hydrophilicity value and still obtain a biologically equivalent, and in particular, an immunologically equivalent protein. In such changes, the substitution of amino acids whose hydrophilicity values are within +2 is preferred, those which are within +1 are particularly preferred, and those within ±0.5 are even more particularly preferred.

As outline above, amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine and isoleucine.

8. Site-Specific Mutagenesis

Site-specific mutagenesis is a technique useful in the preparation of individual peptides, or biologically functional equivalent proteins or peptides, through specific mutagenesis of the underlying DNA. The technique further provides a ready ability to prepare and test sequence variants, for example, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred, with about 5 to 10 residues on both sides of the junction of the sequence being altered.

In general, the technique of site-specific mutagenesis is well known in the art, as exemplified by various publications. As will be appreciated, the technique typically employs a phage vector which exists in both a single stranded and double stranded form. Typical vectors useful in site-directed mutagenesis include vectors such as the M13 phage. These phage are readily commercially available and their use is generally well known to those skilled in the art. Double stranded plasmids are also routinely employed in site directed mutagenesis which eliminates the step of transferring the gene of interest from a plasmid to a phage.

In general, site-directed mutagenesis in accordance herewith is performed by first obtaining a single-stranded vector or melting apart of two strands of a double stranded vector which includes within its sequence a DNA sequence which encodes the desired neurotrophic protein. An oligonucleotide primer bearing the desired mutated sequence is prepared, generally synthetically. This primer is then annealed with the single-stranded vector, and subjected to DNA polymerizing enzymes such as E. coli polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as E. coli cells, and clones are selected which include recombinant vectors bearing the mutated sequence arrangement.

The preparation of sequence variants of the selected neurotrophic gene using site-directed mutagenesis is provided as a means of producing potentially useful species and is not meant to be limiting as there are other ways in which sequence variants of neurotrophic genes may be obtained. For example, recombinant vectors encoding the desired neurotrophic gene may be treated with mutagenic agents, such as hydroxylamine, to obtain sequence variants.

In certain embodiments, it will be advantageous to employ nucleic acid sequences of the present invention in combination with an appropriate means, such as a label, for determining hybridization. A wide variety of appropriate indicator means are known in the art, including fluorescent, radioactive, enzymatic or other ligands, such as avidin/biotin, which are capable of giving a detectable signal. In preferred embodiments, one will likely desire to employ a fluorescent label or an enzyme tag, such as urease, alkaline phosphatase or peroxidase, instead of radioactive or other environmental undesirable reagents. In the case of enzyme tags, calorimetric indicator substrates are known that can be employed to provide a means visible to the human eye or spectrophotometrically, to identify specific hybridization with complementary nucleic acid-containing samples.

In general, it is envisioned that the hybridization probes described herein will be useful both as reagents in solution hybridization as well as in embodiments employing a solid phase. In embodiments involving a solid phase, the test DNA (or RNA) is adsorbed or otherwise affixed to a selected matrix or surface. This fixed, single-stranded nucleic acid is then subjected to specific hybridization with selected probes under desired conditions. The selected conditions will depend on the particular circumstances based on the particular criteria required (depending, for example, on the G+C content, type of target nucleic acid, source of nucleic acid, size of hybridization probe, etc.). Following washing of the hybridized surface so as to remove nonspecifically bound probe molecules, specific hybridization is detected, or even quantitated, by means of the label.

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

OPTIMIZING IN VITRO TRANSFECTION EFFICIENCY USING β-GAL

Previous work has shown that the ratio of nucleic acid to liposomes during transfection is critical for optimizing transfection efficiency in cultured cells. 1 µg of plasmid DNA in 100 µl Dulbecco's Modified Eagle medium (D-MEM) was mixed with 1 µl or 3 µl of cationic liposomes diluted in 100 µl D-MEM, and overlaid overnight onto rat hippocampal cells, 80 to 90% confluent ($2.8\times10^5$ cells per 15 mm plate). X-Gal staining was performed 48 hours after transfection to calculate transfection efficiency. Employing a 1:3 (DNA/liposome) transfection ratio, X-Gal staining was detected both in cells having neuronal and astrocytic morphology (FIG. 1A).

Figure 1B:
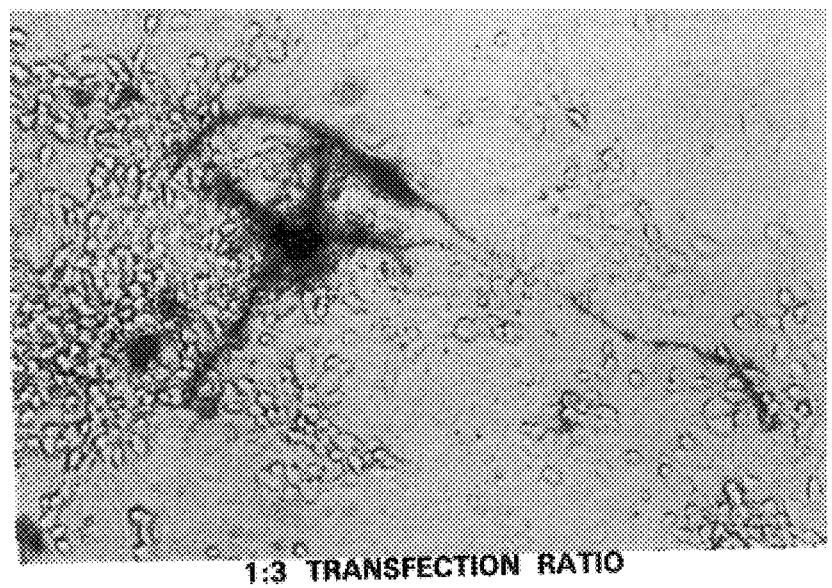
FIG. 1B. Photomicrograph showing X-Gal staining in septo-hippocampal cultures 48 hours after transfection with cDNA for the reporter gene, β-galactosidase. Employing a 1:3 (DNA/liposome) transfection ratio, X-Gal staining was detected both in cells having astrocytic morphology. (Magnification: 360×).
Figure 1C:
FIG. 1C. Photomicrograph showing X-Gal staining in septo-hippocampal cultures 48 hours after transfection with cDNA for the reporter gene, β-Gal. Studies confirm that ratio of nucleic acid to liposomes during transfection is critical for optimizing transfection efficiency. Varying ratios of cDNA to liposomes were overlaid onto rat hippocampal cells. Less efficient transfection was observed with a 1:1 transfection ratio than that observed when a 1:3 ratio was employed (FIG. 1A). (Magnification: 110×).
Figure 1D:
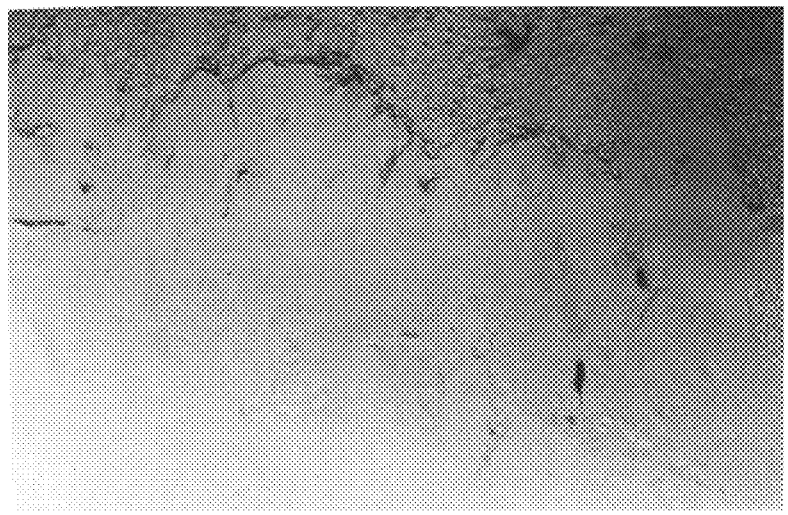
FIG. 1D. Photomicrograph showing X-Gal staining in septo-hippocampal cultures 48 hours after transfection with cDNA for β-Gal. Significant toxicity was observed when more than 5.0 µl of liposomes were employed. (Magnification: 110×).
Figure 2:
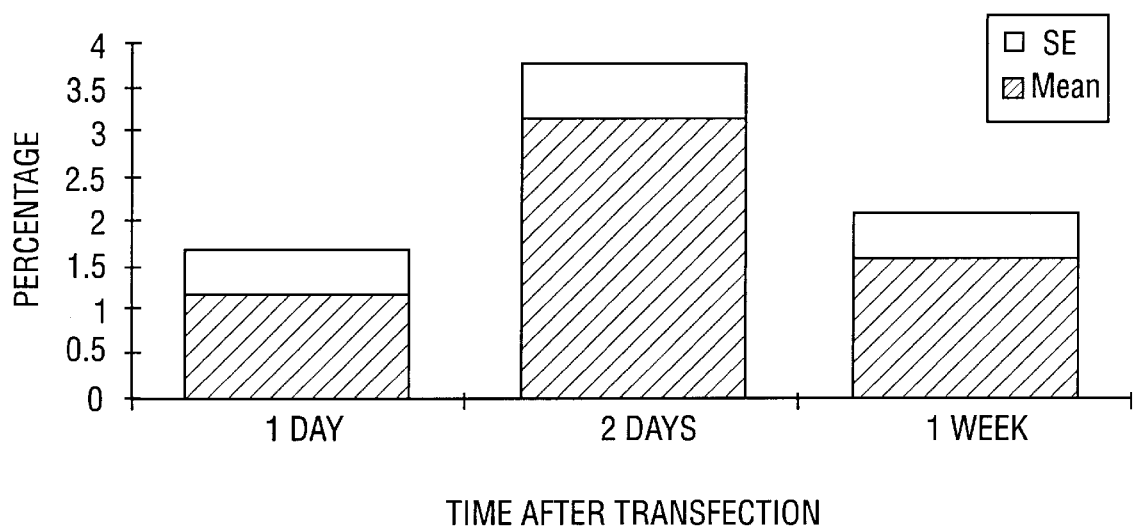
FIG. 2. β-Gal transfection efficiency calculated from X-Gal staining in septo-hippocampal cultures at three time points after transfection with cDNA for β-Gal. A 1:3 ratio of cDNA to liposomes was employed. Data are expressed as a percentage of stained cells to the total number of cells in ten randomly-chosen non-overlapping fields in each of four wells. Counts were conducted independently by two investigators. Maximal transfection was detected two days after transfection and persisted for at least one week.

Less efficient transfection was observed with a 1:1 transfection ratio (FIG. 1B vs. FIG. 1C). Employing a 1:3 ratio of cDNA to liposomes, β-Gal transfection efficiency was calculated from X-Gal staining and septo-hippocampal cultures at three time points after transfection with cDNA for the reporter gene, β-Gal (FIG. 2). Maximal transfection (>3%) was detected two days after injury and persisted for at least one week.

The efficiency of transfection of β-Gal observed in cultured hippocampal neurons (>3%) far exceeds previously reported transfection efficiency for β-Gal in hippocampal cultures employing transfection reagents Transfectam and DOTAP (<0.02%) (Kaech et al., 1993). The differential efficiencies associated with varying ratios of cDNA to liposomes is consistent with the view that the higher the net positive charge of DNA-liposomes complexes, the better the interaction with a negatively charged cell membrane.

EXAMPLE 2

IN VITRO NGF AND BDNF TRANSFECTION

Figure 3A:
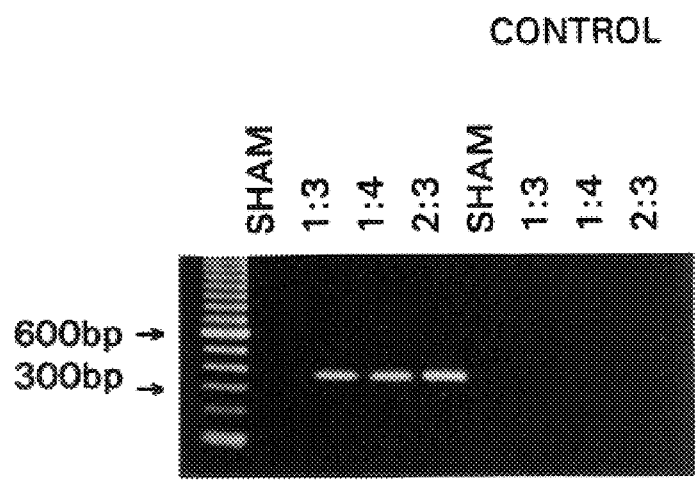
FIG. 3A. RT-PCR analyses of mRNA for BDNF 1 day after transfection of septo-hippocampal cultures employing varying cDNA to liposome ratios. Sham transfections employing only liposomes are also included. Total RNA isolated from four wells was used for reverse transcription of cDNA. To check for possible DNA contamination during RNA preparation, the same RNA samples were included without performing the reverse transcription procedure (denoted by "CONTROL"). Control studies confirmed the absence of DNA contamination. After amplification, samples were resolved on a 1.5% agarose gels. Gels were stained with ethidium bromide and photographed under UV light.
Figure 3B:
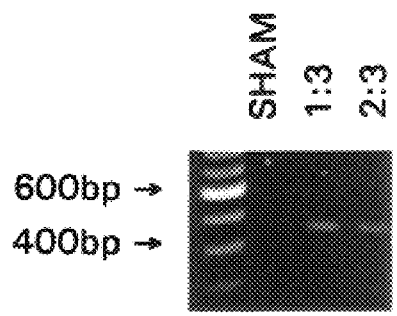
FIG. 3B. RT-PCR analyses of mRNA for BDNF 1 week after transfection of septo-hippocampal cultures employing varying cDNA to liposome ratios. Procedures were as described in the legend to FIG. 3A. Note that 1:4 and 2:3 ratios produced higher levels of mRNA for BDNF one week following transfection than produced by the 1:3 ratio. Note also the increased level in endogenous BDNF in vitro seen at one week in sham preparations (B) as compared to one day post transfection (FIG. 3A).
Figure 3C:
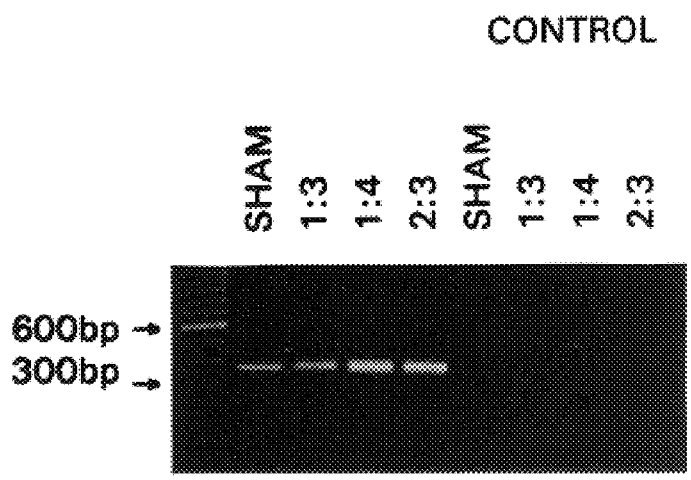
FIG. 3C. RT-PCR analyses of mRNA for NGF one day after transfection. After amplification, samples were resolved on a 1.5% agarose gels. Gels were stained with ethidium bromide and photographed under UV light.

Employing transfection procedures described herein (see Example 1), RT-PCR™ analyses were performed using mRNA for BDNF one day and one week after transfection of septo-hippocampal cultures employing varying cDNA to liposome ratios (FIG. 3A, FIG. 3B, and FIG. 3C). Sham transfections employing only liposomes were also included. Total RNA isolated from each well was used for reverse transcription for cDNA. To check for possible DNA contamination during RNA preparation, the same RNA samples were included without performing the reverse transcription procedure. RT-PCR confirmed increased message for BDNF for all ratios tested, as compared to sham transfections. Control studies confirmed the absence of DNA contamination.

Figure 4A:
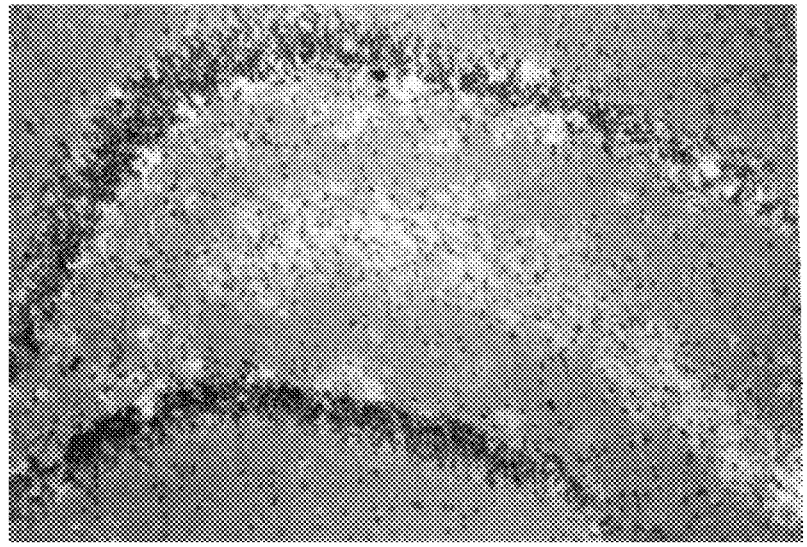
FIG. 4A. Dark field photomicrograph of emulsion in situ hybridization analyses of BDNF transfection in septo-hippocampal cultures 24 hours after transfection (1:3 cDNA to liposomes ratio). Analyses employed $^{33}$P-labeled RNA probe for BDNF. Note prominent radiolabeling superimposed over cell bodies. (Cell bodies are stained with hematoxylin in FIG. 4B).
Figure 4B:
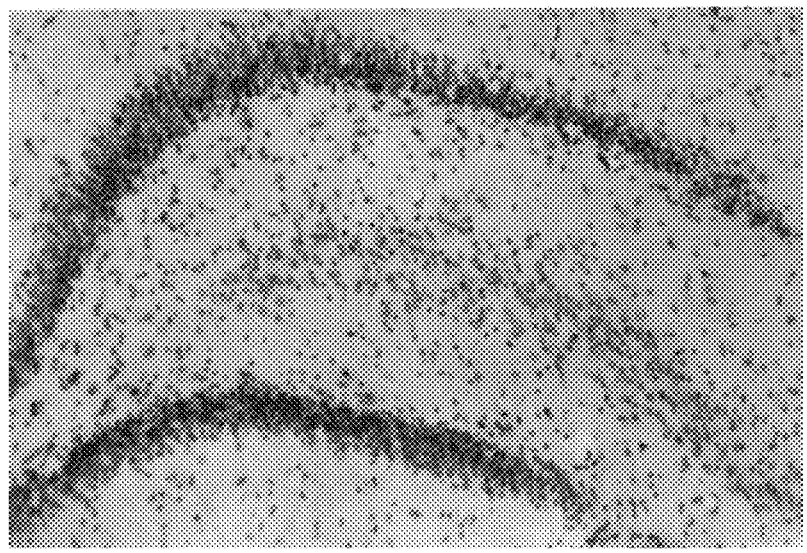
FIG. 4B. Brightfield photomicrograph of emulsion in situ hybridization analyses of BDNF transfection in septo-hippocampal cultures 24 hours after transfection (1:3 cDNA to liposomes ratio). Cell bodies have been stained with hematoxylin, and correspond to the radiodense areas in FIG. 4A.

FIG. 3B shows that 1:4 and 2:3 ratios produced higher levels of mRNA for BDNF one week following transfection than produced by the 1:3 ratio. The inventors also observed increased levels in endogenous BDNF in vitro seen at 1 week in sham transfected preparations (FIG. 3B) and compared to 1 day after sham transfection (FIG. 3A). RT-PCR analyses also confirmed increased mRNA for NGF one day after transfection (FIG. 3C). Preliminary in situ analyses employing $^{33}$P-labeled RNA probe for BDNF also detected prominent radiolabeling (FIG. 4A) superimposed over cell bodies stained with hematoxylin (FIG. 4B).

Figure 5:
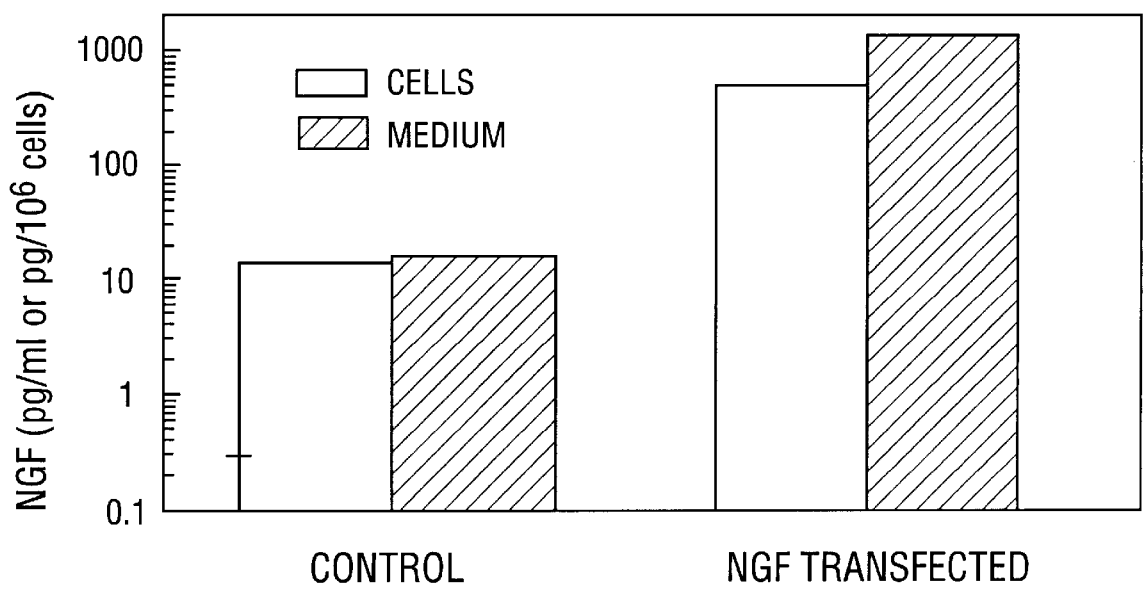
FIG. 5. NGF content in cells (open bars) or culture media (hatched bars) from control (liposomes only) and NGF-transfected (1:3 ratio-cDNA to liposomes) septo-hippocampal cell cultures. Data were collected 3 days after transfection. NGF content was assayed by 2-site ELISA employing a monoclonal antibody (clone 27/21) specific for rat and mouse β (2.5S) NGF. Data for media are expressed as picograms per ml. Data for cells are expressed as picograms per $10^6$ cells. Data are from pooled samples collected from four wells.

ELISA studies have detected dramatic increases in NGF protein both in cells and media 3 days after transfection of septo-hippocampal cultures (FIG. 5). These large increases in NGF indicate that transfected cells are not only producing NGF but also releasing the protein into the culture medium. The observation of similar profiles of neurotrophin production in vivo would strongly suggest that transfection of neurotrophin genes would have therapeutic potential in the intact animal.

EXAMPLE 3

β-GAL TRANSFECTION EFFICIENCY IN VIVO USING UNINJURED RATS

Figure 6A:
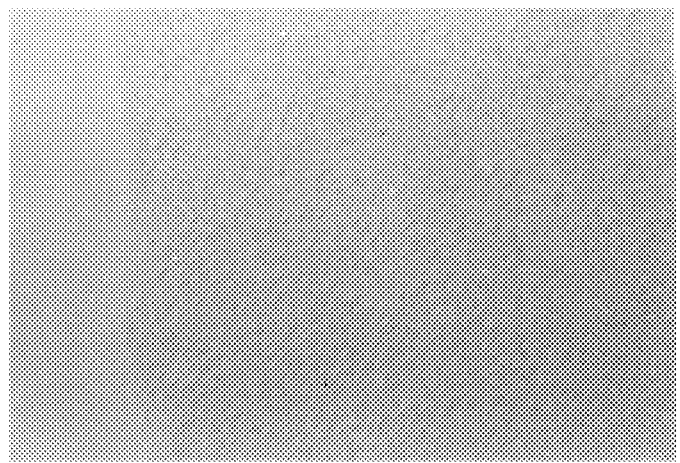
FIG. 6A. Photomicrograph showing no X-Gal staining of the dorsal hippocampus four days after direct intracerebral injections of control liposomes only. (magnification: 55×).
Figure 6B:
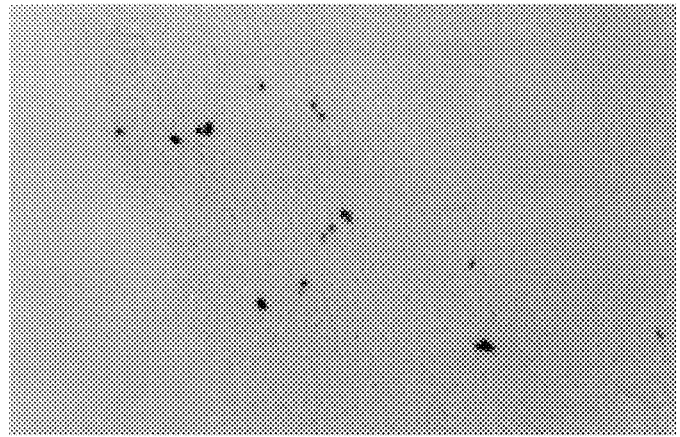
FIG. 6B. Photomicrograph of dorsal hippocampus region four days after direct intracerebral injections of cDNA liposomal complexes (1:3 ratio). X-Gal positive cells have an apparent neuronal and glial morphology in the region of the injection site. Injection site at the left side of the photomicrograph. (Magnification: 55×).
Figure 6C:
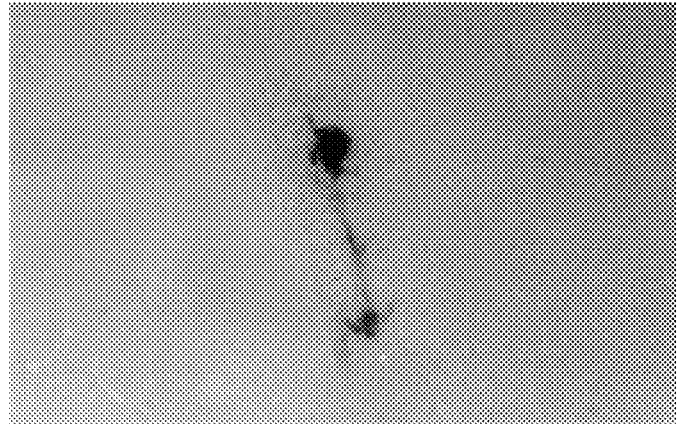
FIG. 6C. Photomicrograph of the dorsal hippocampus four days after direct intracerebral injections of cDNA liposomal complexes (1:3 ratio). X-Gal positive cells have an apparent neuronal and glial morphology in the region of the injection site. Injection site at the left side of the photomicrograph. High-magnification showing staining of cell having apparent neuronal morphology. (Magnification: 220×).

As shown in FIG. 6, the present invention provides evidence that direct intracerebral injections of cDNA:liposomal complexes (1:3 ratio) into the dorsal hippocampus of uninjured rats can produce transfection of the β-Gal reporter gene four days after injection. Initial microscopic analyses indicate X-Gal staining in cells having apparent neuronal and glial morphology.

EXAMPLE 4

NGF AND BDNF EXPRESSION IN SHAM INJURED AND INJURED RATS

Figure 8A:
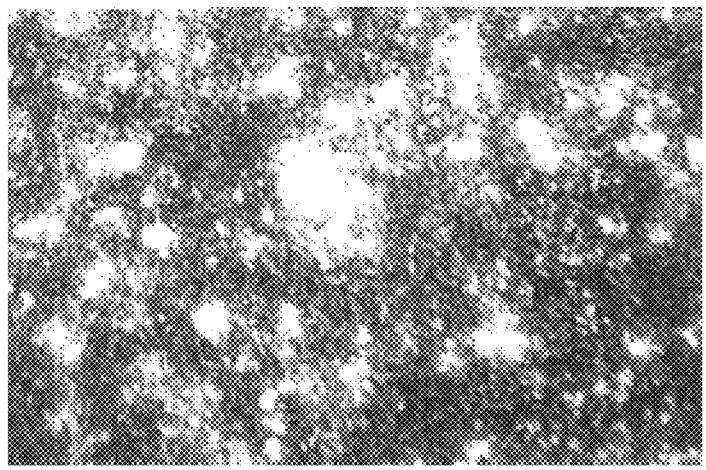
FIG. 8A. Expression of endogenous BDNF following cortical impact injury. Dark field photomicrographs of emulsion in situ hybridization analyses of mRNA expression employing $^{33}$P-labeled cDNA probe for BDNF. Note the increased radiolabeling overlaying cell bodies in dentate gyrus and CA4 of the hippocampus 3 hours after injury.
Figure 8B:
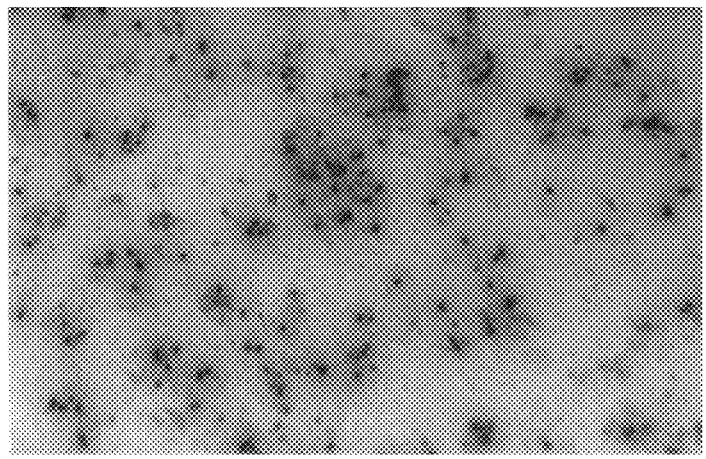
FIG. 8B. Expression of endogenous BDNF following cortical impact injury. Bright field photomicrographs of emulsion in situ hybridization analyses of mRNA expression employing $^{33}$P-labeled cDNA probe for BDNF. The increased radiolabeling overlaying cell bodies in dentate gyrus and CA4 of the hippocampus observed in FIG. 8A is visualized by hematoxylin staining.

In studies of transfection of BDNF and NGF following TBI, it is important to describe the effects of injury on expression of endogenous BDNF and NGF. In situ hybridization analyses of expression of endogenous BDNF have been performed following sham injury (FIG. 7A), 3 hours after cortical impact injury (FIG. 7B), or 1 day following cortical impact injury (FIG. 7C). Cortical impact injury produced prominent increases in expression of endogenous BDNF, especially in the region of the dorsal hippocampus, as compared to sham injury controls. By 1 day following injury, expression of endogenous BDNF had returned approximately to control levels. Emulsion in situ hybridization analyses have been utilized to provide detail on the cellular localization of changes in expression of endogenous BDNF three hours following cortical impact injury (FIG. 8A and FIG. 8B). These studies detected increased radiolabeling primarily localized over cell bodies in regions such as the dentate gyrus and CA4 of the hippocampus.

EXAMPLE 5

CONSTRUCTION OF VECTORS AND LIPOSOME FORMULATION

The cytomegalovirus (CMV) promoter (Fang et al., 1989; Giordano et al., 1991; Li et al., 1992; Thompson et al., 1993) was incorporated into a pUC19-derived expression vector for construction of the NGF and BDNF transfection vectors (pNGF and PBDNF, respectively) (MacGregor and Caskey, 1989; Yang et al., 1994a). The rat NGF and BDNF cDNAs were subcloned individually into a unique NotI site under the control of the CMV promoter. The BDNF and NGF genes were obtained from C. Y. Hsu, Department of Neurology, Washington University School of Medicine, St. Louis, Mo.

A commercially available, 1:1 (w:w) mixture of the cationic lipid n-[1-(2,3-dioleyloxy)propyl]-N,N,N-trimethylammonium chloride (DOTMA) and dioleoyl phosphotidylethanolamine (DOPE) was used for the liposome formulation and was prepared in membrane-filtered water (GIBCO-BRL, Bethesda, Md.).

EXAMPLE 6

EXPRESSION OF mRNA FOLLOWING TRANSFECTION

1. RT-PCR analyses of NGF and BDNF mRNA 1 day after liposome-mediated NGF or BDNF gene transfection (1 µg DNA/3 µl liposomes/well), cells in culture were lysed by adding 0.2 ml of RNAzol B (Cinns/Biotec Laboratories, Inc.) per $10^6$ cells. The RNA preparations were performed as previously described (Yang et al., 1993). Total RNA from individual wells was used for DNA synthesis at 42° C. for 2 h using 200 units of M-MLV reverse transcriptase (Perkin-Elmer, Norwalk, Conn.), 40 nmol of dNTT, 200 mmol DTT and using oligo-dT as primers. Increased NGF (FIG. 5) or BDNF (FIG. 11A and FIG. 11B) mRNA was observed in pNGF- and pBDNF-transfected cells, respectively as compared to sham transfections. To check for possible DNA contamination during RNA preparation, RNA samples were included without performing reverse transcription; no DNA was detected in these control samples.

For PCR™, one pair of forward and reverse primers of NGF were used. The sequence of NGF/5 primer was 5'-GGCATGCTGGACCCAAGCTC-5' (SEQ ID NO:3), and of NGF/3, was 5'-GCGCTTGCTCCGGTGAGTCC-3' (SEQ ID NO:4) (Giordano et al., 1991). Total DNA and 40 pmol of primer were used for PCR™. PCR™ was carried out in a programmable bearing block (Perkin-Elmer, Norwalk, Conn.) using cycles consisting of denaturation at 95° C. for 1 min, followed by annealing at 35° C. for 1 min, and DNA extension at 72° C. for 2 min (Yang et al., 1993).

After 25 cycles of PCR™, samples were electrophoresed on 1.5% agarose gels. Gels were stained with ethidium bromide and photographed under UV light. NGF mRNA expression was increased in NGF DNA-transfected cultures compared to liposome-only treated cultures, and medium-only control cultures. The 100-bp DNA ladder from Gibco BRL (Grand Island, N.Y.) was used as molecular weight markers.

Because of interest in injury mechanisms in the hippocampus and the preferential vulnerability of the hippocampus to traumatic or ischemic brain injury (Jenkins et al., 1989; Lyeth et al., 1990), mixed primary septo-hippocampal cell cultures were used for in vitro studies of liposome-mediated gene transfection. Cultures were incubated for one week prior to transfection. By is that time, astrocytes reached confluence and were no longer actively multiplying, while neurons were well differentiated and stable.

2. ELISA Analysis of NGF Protein

NGF protein levels were examined two days after liposome-mediated NGF transfection using an antibody-sandwich ELISA assay. NGF concentrations were quantified against a standard concentration curve of pure isolated murine NGF. Cells were treated with lysis buffer and extracted on ice for 10 min. Extractions were centrifuged at 20,000×g for 15 min at 4° C. Wells were coated with 0.25 µg/ml anti-NGF antibodies (Boehringer Mannheim Corp., Ind.). A standard NGF dilution series was prepared. Diluted homogenate or medium (100 µl) and standard NGF dilutions (100 µl) were added to the antibody-coated wells and incubated overnight at 4° C. After washing the plate with water and blocking buffer, antibody-β-Gal-conjugate solution (100 µl) was added to each well and incubated (4 h at 37° C.). After another wash with blocking buffer, substrate solution (200 µl) was added to each well and incubated (37° C. for 2 h). Plates were read at 570 nm. A graph of these results showed significant (P<0.01) increases in NGF protein in septo-hippocampal cultures 2 days after transfection (values represent means=S.E.M.; n=4). These studies detected dramatic increases in NGF protein in cell pallets from transfected septo-hippocampal cultures.

Three days after NGF gene transfection, robust increases of NGF protein were detected by ELISA in the cell culture medium. The secreted form of NGF in the medium could still be detected two weeks after pNGF transfection. Since we routinely exchange the medium 3 time a week after gene transfection, the consistent detection of the secreted form of NGF in the medium suggests that septo-hippocampal cells express and secrete NGF for at least two weeks after liposome-mediated gene transfection.

ELISA analysis of NGF protein in culture medium: Three days after NGF gene transfection, NGF protein was increased ten fold in the medium from NGF DNA transfected cultures. Increased secreted NGF could be detected in the medium two weeks after NGF DNA transfection (values represent means=S.E.M.; n=4). The medium was exchanged 3 times a week after gene transfection.

3. PC12 Confirmed NGF Activity Following Transfection

Rat pheochromocytoma (PC12) cells were used to confirm the specific biological activity of NGF in medium conditioned by cell cultures transfected with NGF DNA. PC12 cell medium was removed three hours after plating, a sufficient amount of time for cells to attach to wells, and replaced with 0.5 ml of conditioned medium collected from cultures three days following liposome-mediated NGF DNA transfection. NGF (20 ng/ml) was added to sister wells to assay the cells' response to exogenous NGF. Thirty-three hours later, cells were observed for the presence of neurite outgrowth. The secreted form of NGF in the NGF DNA transfected cell medium produced biological effects similar to those of NGF isolated from mouse submaxillary gland. However, medium from control cells incubated only with liposomes did not produce neurotrophic effects.

Assay of bioactivity of NGF: representative photomicrographs of changes in PC12 cell morphology after 33 h in conditioned media from primary septo-hippocampal cultures. Rat PC12 cells were plated on a 24-well plate (precoated with 50 μg/ml poly-D-lysine in RPM-1640 culture medium at a density of $2 \times 10^6$ cell/0.5 ml). Prominent neuritic outgrowth and associated growth cones were produced by the medium from NGF DNA transfected cultures. These results were similar to those obtained following administration of exogenous NGF.

These results represent the first reported use of liposome-mediated NGF transfection in post-mitotic central nervous system cell cultures. The levels of NGF protein expressed in our transfection system are particularly high, persist for at least 14 days and elicit prominent neurotrophic effects such as neurite growth and growth cone formation. The persistent secretion of large amounts of NGF in media after pNGF transfection suggests the potential utility of neurotrophin gene transfection for treatment of neuronal injury or degenerative disorders.

EXAMPLE 7

MIXED PRIMARY SEPTO-HIPPOCAMPAL CELL CULTURES

Hippocampal and septal neurons are prepared from the brain of 18-day old Sprague-Dawley rat fetuses using the method of Banker and Cowan (1977) (Banker and Cowan, 1977), but without trypsinization. After washing the cells are dissociated by repeated passage through a flame constricted Pasteur pipette, collected by centrifugation, resuspended in D-MEM supplemented with 10% fetal calf serum and then plated on poly-L-lysine coated 24-well plates ($1.09 \times 10^5$ cells/well). Cells for in situ hybridization are plated similarly but in 8-well Nunc Lab-tek chamber slides. Cultures are kept in a humidified $CO_2$ incubator at 37° C. After 5 days of culture the media is changed into DMEM-based B18 medium (Brewer and Cotman, 1989). Subsequent media replacement is carried out twice a week. Cultures are allowed at least one week of incubation prior to transfection. By that time, astrocytes have reached confluence and are no longer actively multiplying, while neurons are well differentiated and stable.

EXAMPLE 8

IN VIVO TRANSFECTION FOLLOWING TBI USING RODENT MODELS

Two models of traumatic brain injury have been developed: The fluid percussion model of traumatic brain injury injects a small volume of saline epidurally into the close cranial cavity of rats (Dixon et al., 1987). The inventors have employed this device to model moderate diffuse brain injury. The second model of brain injury employs pneumatically controlled impact to the exposed cortical surface of rats (Dixon et al., 1991). The inventors employ this device to model severe head injury associated with mass lesions and greater frequency of diffuse axonal injury than observed with the fluid percussion device.

Both of these devices have been used to examine the effects of varying severities of traumatic brain injury on gene transfection. Both of these models were developed in the inventors' laboratories and have been widely employed by investigators of central nervous system trauma.

1. Fluid Percussion Injury

Animals are surgically prepared for fluid percussion injury under sodium pentobarbital anesthesia (54 mg/kg, i.p.) 48 hours prior to trauma (for details, see Dixon et al., 1987). Surgical procedures are performed under sterile conditions in a laboratory site dedicated to rat surgery. A 4.8-mm diameter craniotomy is performed over the sagittal suture midway between lambda and bregma. Two stainless-steel skull screws (2–56×9.5 mm) are placed into burr holes 1 m rostral to bregma and 1 mm caudal to lambda.

A rigid plastic injury tube (modified Leur-loc syringe hub, 2.6 mm inside diameter) is placed over the exposed dura and bonded to the skull with cyanoacrylate adhesive. Dental acrylic is then poured around the injury tube and skull screws and the tube is then sealed with Gelfoam. The scalp is sutures closed and Bacitracin ointment is applied over the incision. Animals are returned to their home cage (one animal per cage) after they have recovered from anesthesia.

All rats are anesthetized with isoflurane (4%) and a 2:1 $N_2O/O_2$ mixture prior to injury. Animals will be observed for the presence of convulsions and apnea. Core body temperature is monitored using a rectal probe and maintained at 37°–38° C. The fluid percussion device consists of a Plexiglas cylindrical reservoir bounded at one end by a Plexiglas piston mounted on O-rings. The entire system is filled with isotonic saline. Injury is induced by the decent of a metal pendulum striking the piston. This injects a small volume of saline epidurally into the closed cranial cavity, producing a brief displacement and deformation of neural tissue. The resulting pressure pulse is monitored on a storage oscilloscope (Textronix 5111).

2. Cortical Impact Injury

The injury device was modified from similar devices developed at the Biomedical Science Department of the General Motors Research Laboratories in Warren, Mich. The pneumatic impactor consists of a small (1.975 cm) bore, double-acting, stroke-constrained, pneumatic cylinder with a 5.0 cm stroke (for details, see Dixon et al., 1991). The cylinder is rigidly mounted on a crossbar. The lower rod end has an impactor tip attached. The upper rod end is attached to the transducer core of a linear velocity differential transformer (LVDT) (Shaevitz Model 500 HR). The impact velocity can be adjusted by controlled gas pressure. Impact velocity is directly measured by the LVDT which produces an analog signal that is recorded for analysis of time/displacement parameters of the impact.

All animals are initially anesthetized with 4% isoflurane and a 2:1 $N_2O/O_2$ mixture. Following endotracheal intubation, rats are mechanically ventilated with a 2% isoflurane mixture. The rats are mounted in the injury device's stereotaxic frame. A midline incision is made, soft tissues reflected, and a craniectomy performed. Core body temperature is monitored continuously by a rectal thermistor probe and maintained at 37–38° C.

EXAMPLE 9

DETERMINATION OF TIME COURSE OF TRANSFECTION

To determine the time course of transfection, in situ hybridization and immunohistochemical studies of the dorsal hippocampus is performed following control injections of liposomes alone and at one day, three days, one week, one month, two months and three months following injections of optimal ratios of cDNA to liposomes for NGF and BDNF. Based on regional analyses, RT-PCR and ELISA studies are conducted at selected time points. At these same selected time points, immunohistochemical analyses of neurotrophin receptors ($p75^{NGFR}$, $p140^{trkA}$, $p145^{trkB}$) and assay bioactivity of NGF and BDNF are also performed. The inventors' choice of time points was based on the observation that liposome mediated gene transfection is transient and has been reported to last up to two months.

EXAMPLE 10

SHORT-TERM POTASSIUM DEPOLARIZATION TRANSIENTLY DECREASES NEUROFILAMENT PROTEINS IN MIXED SEPTO-HIPPOCAMPAL CULTURES

Chronic (3–6 hour) potassium depolarization of cultured neurons enhances maturation of the neuronal cytoskeleton. However, traumatic brain injury, which is accompanied by transient (~3 min.) potassium depolarization produces significant cytoskeletal degradation including loss of axonal NF protein. To investigate the effect of short-term depolarization on neurofilament proteins and determine calcium's role in that effect, mixed septo-hippocampal cultures were exposed for 6 min. to 60 mM KCl in the presence of $Ca^{++}$ concentrations from 1.8 to 5.8 mM. Cultures were depolarized at 10 days in vitro when neuronal arborization was extensive and astrocytes were confluent. At 9 to 10 days after depolarization, cultures were lysed and homogenates were analyzed via SDS-PAGE Western blotting for alterations in NF150 and NF68. 2-D densitometry was used for quantitation.

Neurofilament proteins were decreased in all treated cultures. Initial results indicate levels returned to normal by 10 days after insult following treatment with up to 2.8 mM $Ca^{++}$. This decrease was $Ca^{++}$-dependent and exhibited different time courses for the two proteins examined. Thus, short-term depolarization can temporarily decrease levels of neurofilament proteins. $Ca^{++}$-dependent disruption of the axonal cytoskeleton may play a role in the reversible functional deficits observed in rat models of traumatic brain injury.

EXAMPLE 11

NEUROFILAMENT 68 AND NEUROFILAMENT 200 PROTEIN LEVELS DECREASE AFTER TRAUMATIC BRAIN INJURY

A. MATERIALS AND METHODS

1. Cortical Impact and Tissue Dissection Nine groups (n=6–8 per group) of male Sprague-Dawley rats (250–350 g) were used in this study. Groups included naive animals and the following post-injury groups: sham 3 h, injured 3 h, sham 1 day, injured 1 day, sham 7 days, injured 7 days, sham 14 days, and injured 14 days. For induction of severe TBI, a controlled cortical impact device described previously (Dixon et al., 1991) was utilized. Briefly, rats were intubated and anesthetized with 2% halothane in a 2:1 mixture of $N_2O/O_2$. Two 7 mm diameter craniotomies were performed adjacent to the central suture, midway between lambda and bregma. The dura was kept intact. Injury was induced by impacting the right exposed cortex with a 6 mm diameter tip at a rate of 6 m/sec and a 2 mm compression (Dixon et al., 1991). Sham-injured animals underwent identical surgical procedures but did not receive impact injury. Following cortical impact, animals were extubated and immediately assessed for recovery of reflexes (Dixon et al., 1991). Animals whose righting response did not exceed 5 min were omitted from the study.

Following assessment and at the appropriate time interval, animals were killed under halothane anesthesia and immediately prepared for tissue microdissection. Sections of the hippocampus and cortex directly beneath and craniotomies were removed. Cortex was selected for study because, ipsilaterally, it is the locus of injury, and contralaterally, it may represent a contre coup damage site resulting from tissue extrusion at impact (Meaney et al., 1992). The underlying hippocampal tissue was examined because of its established preferential vulnerability after TBI (Hayes et al., 1992; Taft et al., 1992). The dorsal hippocampus was microdissected bilaterally. Excision of the parietal cortices beneath the craniotomies extended approximately 4 mm laterally, approximately 7 mm rostrocaudally, and to a depth extending to the white matter. All tissue was frozen immediately in liquid $N_2$.

2. Sample Processing and Gel Electrophoresis

The microdissected tissue homogenized at 4° C. in an ice-cold homogenization buffer containing 20 mM PIPES (pH 7.1), 2 mM EGTA, 1 mM EDTA, 1 mM dithiothreitol, 0.3 mM phenylmethylsulfonylfluoride (PMSF), and 0.1 mM leupeptin. The presence of chelators and protease inhibitors prevents endogenous in vitro activation of proteases and subsequent artifactual degradation of the NF proteins in vitro. Proteins were assessed for concentration by the Bradford procedure (Bradford, 1976) and balanced for protein content. Samples were then solubilized by 2;1 dilution in sodium dodecyl sulfate (SDS)-containing stop solution (600 mM Tris, 200 mM EDTA, 10% sucrose, 3% SDS) and heated for 5 min at 85° C. Proteins were reduced with β-mercaptoethanol and resolved by SDS polyacrylamide gel electrophoresis (PAGE). A vertical electrophoresis chamber using a 4.5% acrylamide stacking gel over 6% acrylamide resolving gel was routinely employed. Typically, 50–75 µg of sample protein were run in each lane at constant current (120 mA) for 2.5 h. All sample lanes on each gel contained identical amounts of protein. To insure consistency of gel loading, silver staining of identical sister gels was performed and Ponceau red staining of each blot was conducted prior to immunolabeling. To minimize gel-to-gel comparisons, time course gels were routinely performed to observe NF changes post-injury with all sampling times contained on a single gel.

3. Quantitative Immunoreactivity of NF68 and NF200

Immediately after separation of the proteins by SDS-PAGE, proteins were transferred to nitrocellulose membrane by Western blotting technique (Towbin et al., 1979). Lateral transfer was conducted between two plate electrodes and a transfer buffer containing 62.5 mM glycine, 50 mM Tris, and 10% methanol was utilized. Transfer occurred at a constant current of approximately 365 mA at 4° C. Incubation in primary antibody was performed with either anti-NF68 (Sigma N5139) or anti-NF200 (Sigma N0142) monoclonal antibodies.

NF68 and NF200 were chosen for analysis because they are, respectively, the most important structural and cross-linking elements of neurofilaments. Both monoclonals recognize phosphorylated and non-phosphorylated neurofilament epitopes. Visualization was performed with an avidin-alkaline phosphate kit using 5-bromo-4-chloro-3-indolyl phosphate/nitroblue tetrazolium (BCIP/NBT) as the active chromogen. Using this procedure, the anti-NF68 monoclonal labels a single band having an apparent $M_r$ of 68 kDa, and the NF200 monoclonal produces a somewhat smeared band having an apparent $M_r$ of $\geq 200$ kDa. The smearing of NF200 is caused by the physiochemical properties of this long, rigid protein and its extensive, variable level of phosphorylation (Julien and Mushynski, 1982; Nixon and Sihang, 1991).

4. Statistical Analysis

The studies described were performed with 6–8 rats. Each sample was performed in duplicate for a total of 12–16 data points per condition. Quantitative analysis of the proteins employed a computer-assisted, linear scanning densitometer (GS300, Hoefer Scientific). All quantitative readings were performed within a linear range of optical densities. All lanes on immunoblots were scanned in the dark under optimal conditions three times, and the results were averaged for inclusion in data analysis. Lanes that contained prominent gel artifacts were excluded from further data analysis.

Statistical significance of NF immunoreactivities was evaluated using an independent t-test analysis of the pooled data and a post-hoc Tukey-Honest significant difference (HSD) analysis of variance (ANOVA) to detect percentage differences by group analysis for all gels analyzed. All values were expressed as percent change relative to naive values on each immunoblot. Data were considered significant if $p < 0.05$.

B. RESULTS

1. Sham Injury Does Not Affect NF68 and NF200 Levels

NF68 and NF200 protein levels from sham-injured animals at all time points were compared with levels from naive rats to determine the effect of animal surgery (craniotomies) in the absence of TBI. Both hippocampal and cortical tissues were examined, ipsilaterally and contralaterally. NF68 and NF200 levels from naive cortex did not differ significantly from cortices of sham-injured animals at any post-injury time investigated ($p < 0.05$). Similarly, NF68 and NF200 also were unchanged in sham-injured hippocampal tissue when compared with naive hippocampi ($p < 0.05$) (Table 2). Hence, sham injury had no significant influence on NF68 or NF200 protein levels in either the cortex or the hippocampus at any time point investigated.

The effect of lateral cortical impact injury on the levels of axonal cytoskeletal proteins was examined in adult rats. TBl caused a significant decrease in the protein levels of two major neurofilament (NF) proteins, NF68 and NF200. By quantitating immunoreactivity measurements of Western, blots NF68 and NF200 levels were determined in homogenates of hippocampal and cortical tissue taken at several intervals post-injury. Sham injury had no effect on NF protein levels. However, injury was associated with a significant (up to 41.8%) loss of NF68, restricted to the cortex ipsilateral to the injury site. NF68 loss was detectable as early as three hours and as late as two weeks post-injury.

Similarly, TBl induced a decrease in NF200 protein, although losses were observed both ipsilateral (71.7%) and contralateral (66.9%) to the injury site. No loss of NF68 or NF200 protein was detected in hippocampal samples obtained from the same injured animals. An increase in the presence of lower molecular weight NF68 immunopositive bands was associated with the decrease of NF68 in the injured ipsilateral cortex. This NF68 antigenicity pattern suggests the production of NF68 breakdown products (BDPs) caused by the pathological activation of neuronal proteases such as calpain.

Putative NF68 BDPs increased significantly until one day post-injury, suggesting that NF degradation may be ongoing and indicating that a potential therapeutic window may exist within the first 24 hrs post-injury. In summary, these data identify specific biochemical alterations of the axonal cytoskeleton following TBl.

EXAMPLE 12

EXTRACELLULAR CHOLINE LEVELS AND [$^3$H]-CHOLINE UPTAKE IN HIPPOCAMPUS 2-WEEKS AFTER CORTICAL IMPACT INJURY IN RATS

Chronic spatial memory deficits following experimental traumatic brain injury may be, in part, attributable to deficits in central cholinergic neurotransmission. These studies examined the rate-limiting factor in acetylcholine synthesis; availability and neuronal uptake of its precursor, choline. In the first study microdialysis was used to measure extracellular choline levels within the dorsal hippocampus at 2-weeks post-injury, an interval associated with spatial memory deficits. Ten rats were injured by lateral cortical impact. Ten additional rats served as sham controls. Under anesthesia, a microdialysis probe (3 mm tip) was placed into their dorsal hippocampus and perfused with artificial cerebro spinal fluid CSF. Samples were collected for 20 minutes (min) and measured by HPLC. The data showed no difference in basal choline levels between injured ($3.86 \pm 0.53$ pmol/20 min) and sham ($3.35 \pm 0.50$) rats.

In a second study high-affinity [$^3$H]-choline uptake was measured in a synaptosomal preparation of hippocampal tissue removed from 11 injured and 12 sham rats 2-weeks following TBl. Significant differences were found in the maximum velocity of choline uptake (Vmax) between injured ($46.2 \pm 2.3$ pmol/mg/5 min) and sham ($58.8 \pm 2.1$) rats, while no differences in affinity constants ($K_m$) were found. The results suggest that post-traumatic cholinergic deficits are not attributable to decreased availability of choline, but may be associated with either a decreased ability of cholinergic neurons to take up choline, or a loss of cholinergic neurons.

EXAMPLE 13

VISUALIZATION OF ACUTE STRUCTURAL DERANGEMENTS OF CORTICAL NEURONS IN THE RAT FOLLOWING TBI USING NF IMMUNOFLUORESCENCE

Quantitative Western blot studies demonstrated significant losses of neurofilament 68 (NF68) and neurofilament 200 (NF200), as well as the presence of low molecular weight proteolytic fragments as early as 3 hours and for as long as two weeks following lateral cortical impact injury in rats. Three hours following injury, NF68 decreased 23% and NF200 decreased 50% in the ipsilateral cortex. In the contralateral cortex, TBI produced significant loss (65%) of only NF200 3 hours after injury. Consequently, NF immunofluorescence was used to study the morphological correlates of early NF protein decreases observed 3 hrs post TBI.

Using anti-NF200 (Sigma N52) and anti-NF68 (Sigma NR4) antibodies that recognize their appropriate subunits independent of phosphorylation state, total NF protein was detected regardless of post-translational modifications. Secondary anti-mouse IgG was conjugated with either FITC or Rhodamine. TBI induced differential alterations in NF68 and NF200 immunolabeling which were restricted to the ipsilateral contusion site (2–4 mm lateral from the middle longitudinal tissue [MLF]) as well as a focal contralateral contusion site (1–2 mm from MLF).

NF200 immunofluorescence revealed a prominent fragmented appearance of the apical dendrites within pyramidal neuronal layers 3 and 5, as well as a loss of fine dendritic arborization within layer 1. NF68 immunofluorescence detected subtle and less severe ultrastructural changes such as focal vacuolization along apical dendrites, although macrostructural changes (i.e., broken apical dendrites) also occurred to a lesser degree. Although axonal alternations were observed with anti-NF68 and anti-NF200 in the corpus callosum and other white matter areas, axonal alterations were markedly less than the acute NF immunofluorescence changes seen in dendritic regions.

Collectively, these observations suggest that early NF protein loss is observed in dendrites, and to a lesser extent, in axons following injury. Since neurofilaments are structural proteins found abundantly in dendritic as well as axonal processes, diffuse injury to neuronal processes may be an important morphological feature of TBI. Immunohistochemical studies were employed to exam the temporal and regional characteristics of this diffuse process injury (DPI).

EXAMPLE 14

AMYLOID PROTEIN PRECURSOR LEVELS ARE ALTERED IN RAT HIPPOCAMPUS AND CORTEX FOLLOWING TRAUMATIC BRAIN INJURY

Increases in the diffuse deposition of AS protein can occur following traumatic brain injury in humans. Furthermore, levels of the precursor to AS protein (amyloid protein precursor: APP) are increased in rodent brain following CNS lesion. In order to investigate the effect of traumatic brain injury on APP levels, homogenates of rat cortex and hippocampus were prepared 3 h, 1 day, 7 days, or 14 days after lateral cortical impact injury. SDS-PAGE Western blots were immunostained using an antibody which recognizes all three main forms of the amyloid protein precursor (22C11, Boehringer-Mannheim, Indianapolis, Ind.). 2-D densitometric scanning was used to quantify changes in protein levels.

Data indicated that APP levels were significantly decreased at 2 weeks in cortex ipsilateral to injury. In contrast, a significant increase was observed in ipsilateral hippocampus 1 day after injury. These results indicate that alterations in APP after traumatic brain injury are regionally specific. Thus, mechanisms mediating TBI-induced changes in APP levels may differ in various regions of the rodent brain.

EXAMPLE 15

EFFECTS OF LATERAL CORTICAL IMPACT INJURY ON AXONAL PROTEINS

The effect of lateral cortical impact injury on the levels of axonal cytoskeletal proteins has been examined in adult rats. Traumatic brain injury (TBI) causes a significant decrease in the protein levels of two prominent neurofilament (NF) proteins, NF68 and NF200. Quantiative immunoreactivity measurements were performed using Western blots to examine NF68 and NF200 levels in homogenates of hippocampal and cortical tissue taken at several intervals post-injury. Sham injury had no effect on NF protein levels. However, injury was associated with a significant loss of NF68, restricted to the cortex ipsilateral to the injury site.

1. Injury Results in Significant loss of NF68 and NF200

NF68 loss was detectable as early as 3 h and lasted at least 2 weeks post-injury. Similarly, TBI induced a decrease in NF200 protein, although losses were observed both ipsilateral and contralateral to the injury site. No loss of NF68 or NF200 protein was detected in hippocampal samples obtained from the same injured animals. An increase in the presence of lower molecular weight (MW) NF68 immunopositive bands was associated with the decrease of NF68 in the ipsilateral cortex. This NF68 antigenicity pattern suggests the production of NF68 breakdown products caused by the pathologic activation of neuronal proteases, such as calpain. Putative NF68 breakdown products increase significantly until 1 day post-injury, suggesting that NF degradation may be ongoing until that time and indicating that a potential therapeutic window may exist within the first 24 h post-injury.

2. TBI Decreases NF68 Levels Only in Ipsilateral Cortex

The effect of lateral cortical impact injury on NF68 immunoreactivity in cortical tissue was examined at several intervals post-injury. Naive, sham-injured, and cortical impact-injured samples were examined for NF68 protein content by SDS-PAGE and quantitative Western immunoreactivity at 3 h, 1 day, 7 days, and 14 days after injury. Proteins were visualized on nitrocellulose transfers using an anti-NF68 monoclonal antibody. A significant decrease in NF68 protein was noted at all postinjury time points examined. The decrease in NF68 antigenicity was accompanied by the appearance of two lower MW immunopositive bands at 56 and 52 kDa.

Figure 9A:
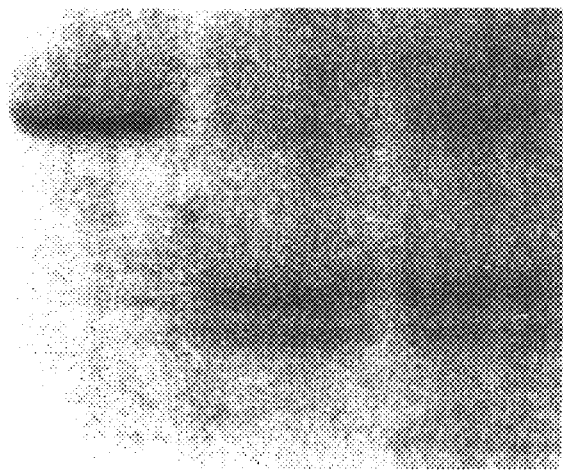
FIG. 9A. TBI causes the appearance of low MW NF68 immunopositive proteins. Severe cortical impact TBI produces a decrease in the protein levels of NF68 in ipsilateral cortical samples. Associated with the loss of NF68 immunostaining is the appearance of prominent lower MW bands, which are recognized by the NF68 monoclonal. Shown is an immunoblot of ipsilateral cortical samples from sham (S, lane 1) and injured (I, lanes 2, 3) animals at 1 day post-injury. Prominent 56-kDa and 52-kDa bands were observed in cortical injured animals, but were not prominent in sham samples. This pattern of low MW immunopositive bands resembles the pattern of NF68 breakdown products produced by calpain-dependent proteolysis of NF68 (Kamakura et al., 1985; Schlaepfer et al., 1984).
Figure 9B:
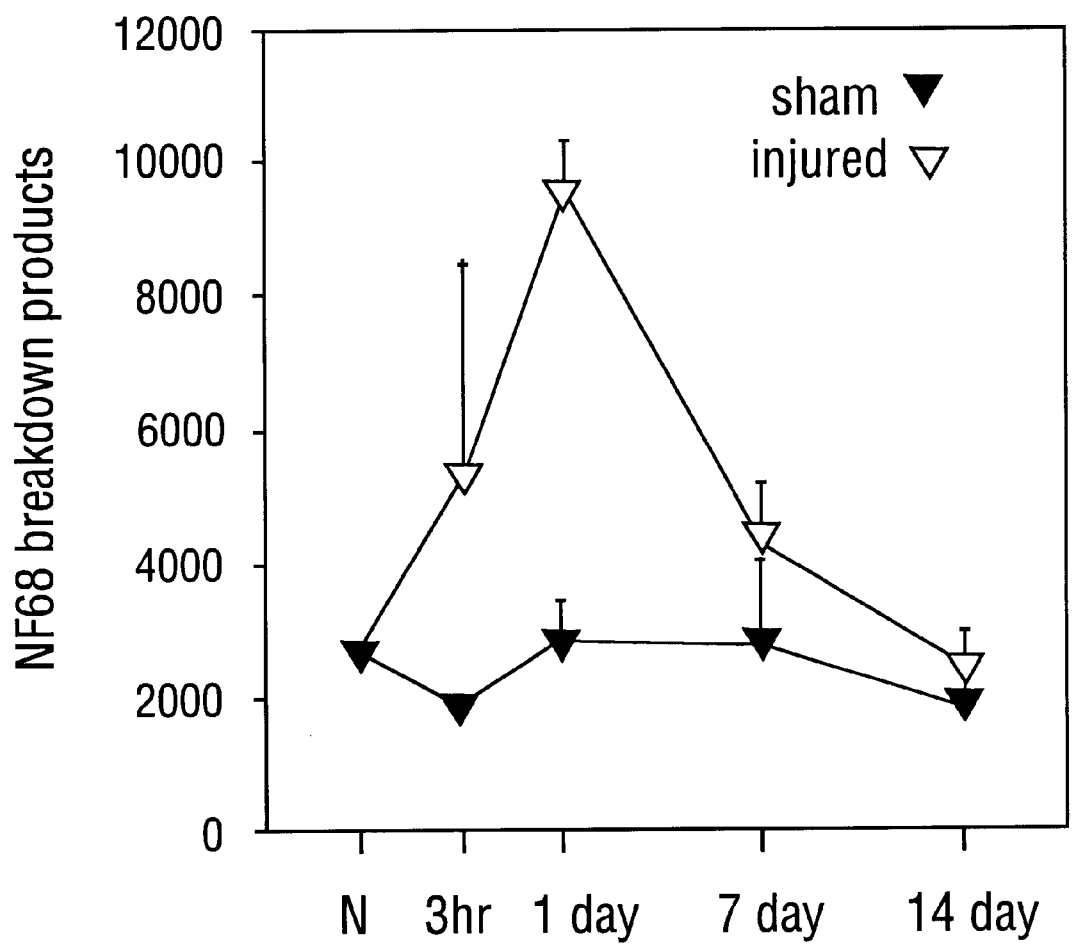
FIG. 9B. TBI causes the appearance of low MW NF68 immunopositive proteins. Severe cortical impact TBI produces a decrease in the protein levels of NF68 in ipsilateral cortical samples. Associated with the loss of NF68 immunostaining is the appearance of prominent lower MW bands, which are recognized by the NF68 monoclonal. Shown is the quantitation of the appearance of NF68 breakdown products. Immunoblots were analyzed quantitatively for total NF68 breakdown products by computer-assisted scanning densitometry. Ordinate values represent arbitrary densitometric units. The low MW immunoreactivity in sham (closed triangles) animals did not change with time, but a dramatic increase was seen in injured (open triangles) animals. The greatest amount of NF68 breakdown products appears at 1 day post-injury.
Figure 10:
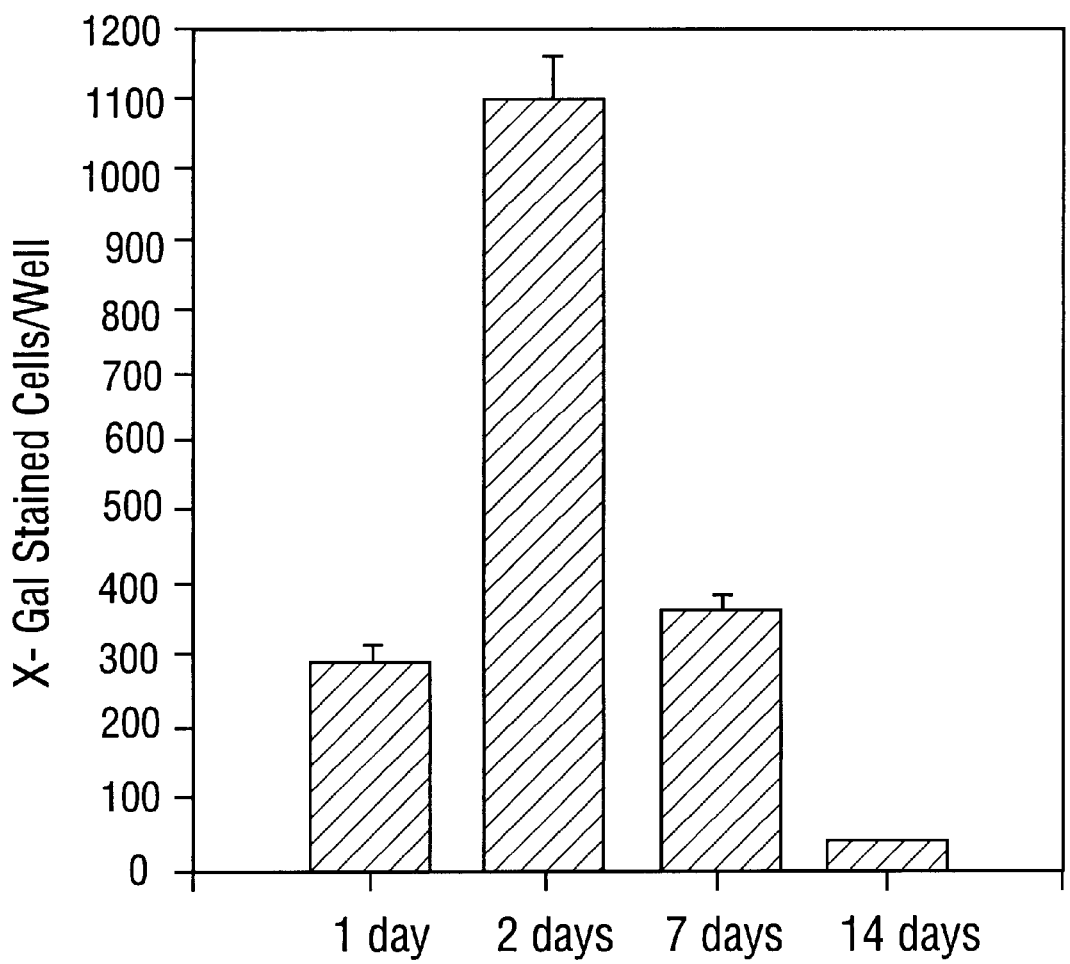
FIG. 10. β-Galactosidase transfection efficiency was calculated from X-Gal staining in septo-hippocampal cultures at 4 time points after transfection with pCMV/β-gal using 1 μg DNA/3 μl liposomes/well. Cell counts were conducted independently by two investigators. The values represent the mean ± S.E.M. of the average number of X-Gal stained cells in each well at 1, 2, 7, and 14 days following transfection (n=4). β-Gal expression was maximal 2 days after transfection and persisted for 2 weeks.

In the contralateral cortex, no significant change in NF68 levels was noted between sham and injured samples. The most prominent loss (58.2% of sham controls) occurred at 7 days post-injury. The process of NF68 loss was induced within 3 h post-injury, but continued reduction of NF68 occurred beyond 1 week. In addition, NF68 levels at 1 day (63.9% of sham controls) were significantly lower than the 3 h value (78.9% of sham controls) ($p<0.04$). Post-hoc Tukey-HSD ANOVA analysis (% difference group) for all gels at $p<0.05$ also showed significance at all time points except 3 h. In addition to labeling of the prominent 68 kDa band, additional immunopositive bands were found in samples from injured cortex. These lower MW immunopositive bands appeared prominently at 56 kDa and 52 kDa and are accompanied by other minor staining bands in the same MW range (FIG. 9A and FIG. 9B)

TABLE 2

| NF68 AND NF200 LEVELS IN HIPPOCAMPAL SAMPLES[a] | | | | |
|---|---|---|---|---|
| | 3 h | 1 Day | 7 Days | 14 Days |
| NF68 Protein Levels | | | | |
| Ipsilateral | | | | |
| Sham | 99.9 ± 6.6 | 94.6 ± 1.6 | 91.8 ± 3.3 | 93.1 ± 4.5 |
| Injured | 88.9 ± 5.9 | 86.8 ± 4.8 | 85.7 ± 2.0 | 84.5 ± 3.0 |
| Contralateral | | | | |
| Sham | 101.9 ± 5.3 | 97.2 ± 4.1 | 95.1 ± 7.6 | 94.4 ± 3.6 |
| Injured | 93.05 ± 1.9 | 92.0 ± 6.4 | 95.9 ± 4.3 | 90.3 ± 3.7 |

TABLE 2-continued

NF68 AND NF200 LEVELS IN HIPPOCAMPAL SAMPLES[a]

|  | 3 h | 1 Day | 7 Days | 14 Days |
|---|---|---|---|---|
| NF200 Protein Levels | | | | |
| Ipsilateral | | | | |
| Sham | 94.1 ± 6.1 | 96.6 ± 18.0 | 103.1 ± 15.2 | 87.8 ± 11.5 |
| Injured | 83.9 ± 10.4 | 110.9 ± 5.5 | 87.8 ± 11.5 | 87.2 ± 7.8 |
| Contralateral | | | | |
| Sham | 94.2 ± 8.3 | 96.4 ± 1.6 | 96.9 ± 1.6 | 78.9 ± 9.4 |
| Injured | 105.4 ± 6.4 | 95.6 ± 10.3 | 87.7 ± 11.6 | 86.6 ± 4.2 |

[a]NF68 and NF200 levels in hippocampus after severe cortical impact TBI. The effect of lateral cortical impact injury on NF68 and NF200 immunoreactivity in hippocampal tissue was examined at several intervals post-injury. Naive, sham-injured, and cortical impact-injured samples were examined for neurofilament protein content by SDS-PAGE and quantitative Western immunoreactivity at 3 h, 1 day, 7 days, and 14 days after injury. Proteins were visualized on nitrocellulose transfersusing appropriate monoclonal antibodies. Immunoblots were analyzed quantitatively by computer-assisted scanning densitometry. Data are expressed as percentage relative to naive controls. No significant changes in NF68 or NF200 protein levels are detected in hippocampal tissue either ipsilateral or contralateral to the injury site. Statistical analysis of the data included an independent t-test of the pooled data and a post hoc Tukey-HSD ANOVAto detect percentage difference by group analysis for all gels analyzed. All values were p < .05. Thus, no injured groups showed significant differences from the sham-injured controls.

Cortical impact injury was associated with the onset of a pronounced and prolonged loss of NF68 in the ipsilateral cortex. NF68 levels in the ipsilateral cortex were significantly reduced at 3 h, 1 day, 7 days, and 14 days. NF68 levels in the contralateral cortex did not differ from sham controls at any time point studied. No prominent lower MW immunopositive bands were seen in the contralateral cortical samples. Thus, the data suggest a clear differential reduction in NF68 protein selective to the ipsilateral cortex caused by TBI.

3. TBI Decreases NF200 in Cortical Tissue

The effect of lateral cortical impact injury on NF200 immunoreactivity in cortical tissue was also examined at several intervals post-injury. Naive, sham-injured, and cortical impact-injured samples were examined for NF200 protein content as described at 3 h, 1 day, 7 days, and 14 days after injury. Proteins were visualized on nitro-cellulose transfers using an anti-NF200 monoclonal antibody. In the ipsilateral cortex, a significant decrease in NF200 protein was noted at all post-injury time points examined. In the contralateral cortex, a reduction of NF200 levels was noted between sham and injured samples at all intervals post-injury.

TBI also caused a dramatic reduction in cortical NF200 protein levels. NF200 loss was most prominent in the ipsilateral cortex, but unlike the NF68 changes, significant loss of NF20 occurred in the contralateral cortex as well. In the ipsilateral cortex, NF200 loss was seen at 3 h and remained significantly reduced as long as 2 weeks post-injury. The greatest loss (28.3% of sham control) was observed at 7 days post-injury.

NF200 immunoreactivity in the contralateral cortex also showed a consistent TBI-induced reduction. Although each time point analyzed showed reduction of NF200 levels relative to sham controls, significant decreases occurred only at 3 h and 14 days. The increased variability of NF200 sampling suggests a more diverse insult to NF protein contralaterally.

4. TBI Does Not Produce Derangements of NF Proteins in Hippocampal Tissues

NF68 and NF200 immunoreactivity was performed on the corresponding underlying hippocampal tissue for all animals studied. NF68 immunoreactivity in the ipsilateral and contralateral hemispheres did not show any significant differences, (p<0.05) compared with sham-injured controls. Similarly, NF200 demonstrated no significant loss in either hemisphere of injured animals compared with sham-injured animals (Table 2). The low MW NF68 immunopositive bands were not seen in hippocampal samples.

5. Post-TBI NF Protein Loss Is Associated with the Presence of NF Breakdown Products Immunoanalysis of NF68 on Western blots demonstrated a prominent single band at 68 kDa in naive, sham, and injured animals. In injured samples, however, the decrease in NF68 levels was associated with the appearance of lower MW immunopositive bands (FIG. 9A and FIG. 9B). The minor bands were found at molecular weights of 56 kDa and 52 kDa. The presence of the lower MW bands associated with TBI and the concomitant reduction of NF68 suggest the appearance of lower MW breakdown products (BDPs) caused by the post-injury activation of proteases. The low MW immunopositive proteins appeared at 3 h post-injury and attained their highest levels at 1 day (FIG. 9B). These bands were markedly reduced in 7 and 14 days samples. The presence of low MW immunopositive bands has been reported previously following both in vitro and in vivo proteolysis of NF68 (Schlaepfer et al., 1984; Schalepfer and Zimmerman, 1985).

6. The Role of Cytoskeletal Proteins in Trauma

Studies have addressed the relationships between changes in axonal and dendritic cytoskeletal proteins and the morphopathologic outcome of trauma. These quantitative analyses indicate that NF changes precede neuronal cell death and, further, may not be exclusively associated with cell death. For example, cortical NF68 levels were significantly decreased at 3 h post-injury, well in advance of cellular necrosis in the cortex. In addition, cortical NF200 loss occurred contralateral to the impact site, in the absence of substantial cell death.

Similarly, loss of cortical NF200 has been reported contralaterally to middle cerebral artery occlusion in rats where no cell death occurred but which may contribute to postischemic symptomatology (Inuzuka et al., 1990b). Subsequent studies directly linked to neuropathology may determine whether the NF losses reported are initial components of axonal damage and separation or are the beginnings of Wallerian degeneration of the distal axonal segment of the already severed axon. Alternatively, decreases in NF may represent persistent sublethal alteration in the cytoskeleton not associated with classic morphopathologic features of traumatic axonal injury.

Even in the absence of cell death or axonal disruption, the NF changes identified may have important consequences that compromise neuronal function and may contribute to sublethal neuronal injury. NF68 and NF200 are key elements of neurofilaments, and extensive loss of these proteins after TBI may compromise neurofilament function in injured neurons. Such insults may be critical to neuronal viability and normal function because neurofilaments appear to play a crucial role in the maintenance of axonal and dendritic structure, caliber, axoplasmic transport, and other functions (Hoffman and Lasek, 1975; Mellgren and Murachi, 1990; Oliver et al., 1989). These actions may be significantly impaired post-injury with the losses of NF protein reported here.

NF68 loss at 1 day post-injury is significantly greater than the loss observed at 3 h post-injury. This difference could indicate that the pathologic processes causing NF loss are incomplete 3 h post-injury and are ongoing at that time. Because the NF loss at 1, 7, and 14 days is not statistically different, the pathologic causes of NF loss may have peaked at these times. These observations are consistent with the appearance of NF68 BDPs, which also peak 1 day post-injury. In experimental models of ischemia, administration of anti-calpain compounds has proven effective in preventing ischemia-induced cytoskeletal protein loss (Inuzuka et al., 1990a; Lee et al., 1991; Siman et al., 1989). In models of TBI, treatment with moderate hypothermia reduces injury-associated MAP2 loss (Taft et al., 1993). Thus, the changes in NF protein levels may be amenable to therapeutic intervention in the first 24 h post-TBI. The time course of NF changes further suggest that NF loss will not recover to normal (sham control) levels within the first 2 weeks following insult. The examination of longer post-injury intervals may be necessary to determine whether neurons can independently recover NF protein levels following severe cortical impact TBI.

7. Conclusions

Several important conclusions were derived from these studies. First, the pattern and temporal progression of NF68 and NF200 loss were similar. Reductions in NF levels were observed within 3 h post-injury and appear unresolved 2 weeks later. Second, the extent of NF protein loss was greater in the hemisphere ipsilateral to the injury site compared with the contralateral side. For example, a pronounced loss of NF68 was seen ipsilaterally, but no loss was observed contralaterally. Third, the loss of NF200 was more extensive compared with loss of NF68. In the ipsilateral cortex, NF200 loss reached 70% (30% of sham control values), whereas NF68 loss was 40% (60% of sham control values). Fourth, a higher degree of sample-to-sample variability was observed with NF200 compared with NF68. A potential cause for the greater loss and higher variability of NF200 post-TBI may be NF200 subunit disassembly from the core filament, thus increasing its availability for phosphorylation or proteolysis or both. Further, because NF phosphorylation state influences NF proteolysis by calpain (Pant, 1988), variable levels of NF200 phosphorylation from animal to animal may contribute significantly to the variability of NF200 antigenicity.

EXAMPLE 16

RESCUE OF NEUROFILAMENT LOSS FROM NEURONAL INJURY BY BDNF GENE TRANSFECTION IN PRIMARY SEPTO-HIPPOCAMPAL CELL CULTURE

Cortical impact injury in rats can produce significant loss of neurofilament proteins including medium, low and high molecular weight neurofilament proteins (NF-L, NF-M, NF-H). In addition, brief depolarization of primary septo-hippocampal cell cultures can also produce significant losses of neurofilament proteins. Recent studies indicate that BDNF increases neurofilaments in hippocampal cell cultures (Yip et al., 1993) and increases survival of cortical neurons (Ghosh et al., 1994). Using a liposomal mediated system for transfecting cDNA of neurotrophins into central nervous system cells primary septo-hippocampal cell cultures were transfected to determine the therapeutic potential of BDNF gene transfection in facilitating the recovery of neurofilament loss caused by depolarization injury.

Figure 11A:
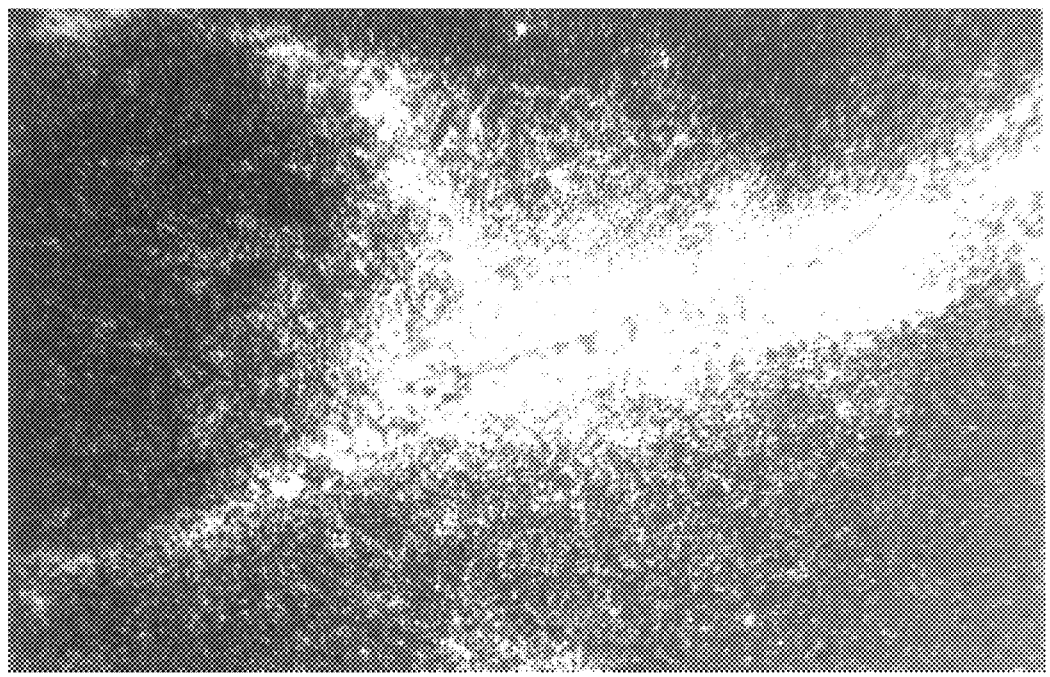
FIG. 11A. Expression of BDNF in non-injured rats following transfection of liposome-BDNF cDNA complex (1:3 ratio) in the hippocampus. Dark field photomicrographs of emulsion in situ hybridization analyses of mRNA expression employing $^{33}$P-labeled cDNA probe for BDNF. (Magnification: 110×).
Figure 11B:
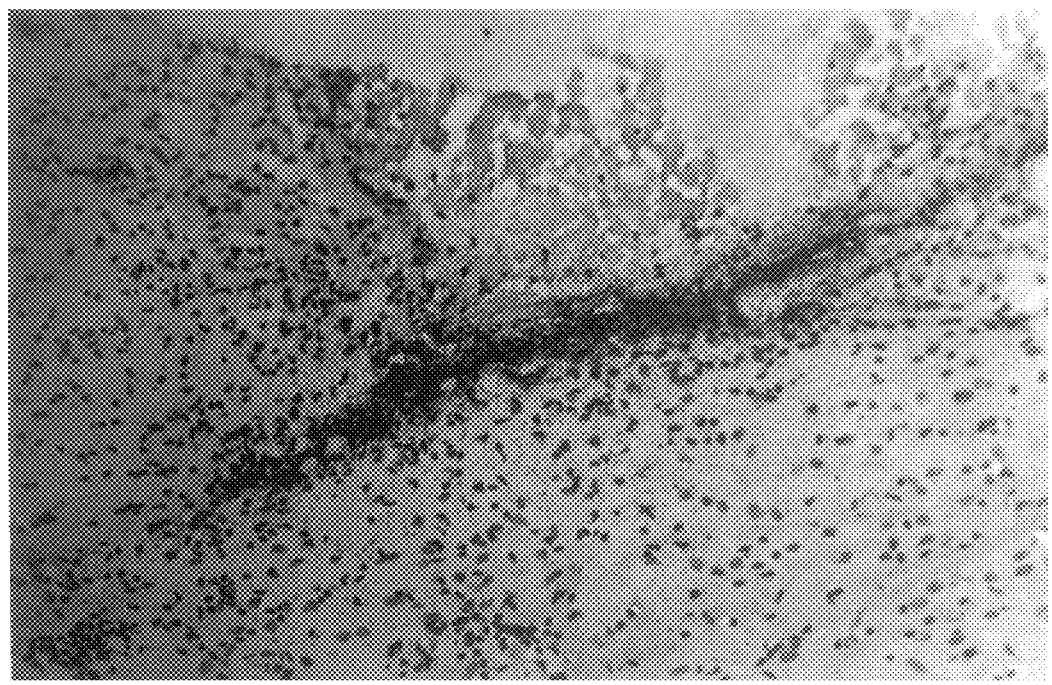
FIG. 11B. Expression of BDNF in non-injured rats following transfection of liposome-BDNF cDNA complex (1:3 ratio) in the hippocampus. Bright field photomicrographs of emulsion in situ hybridization analyses of mRNA expression employing $^{33}$P-labeled cRNA probe for BDNF. (Magnification: 110×).
Figure 12:
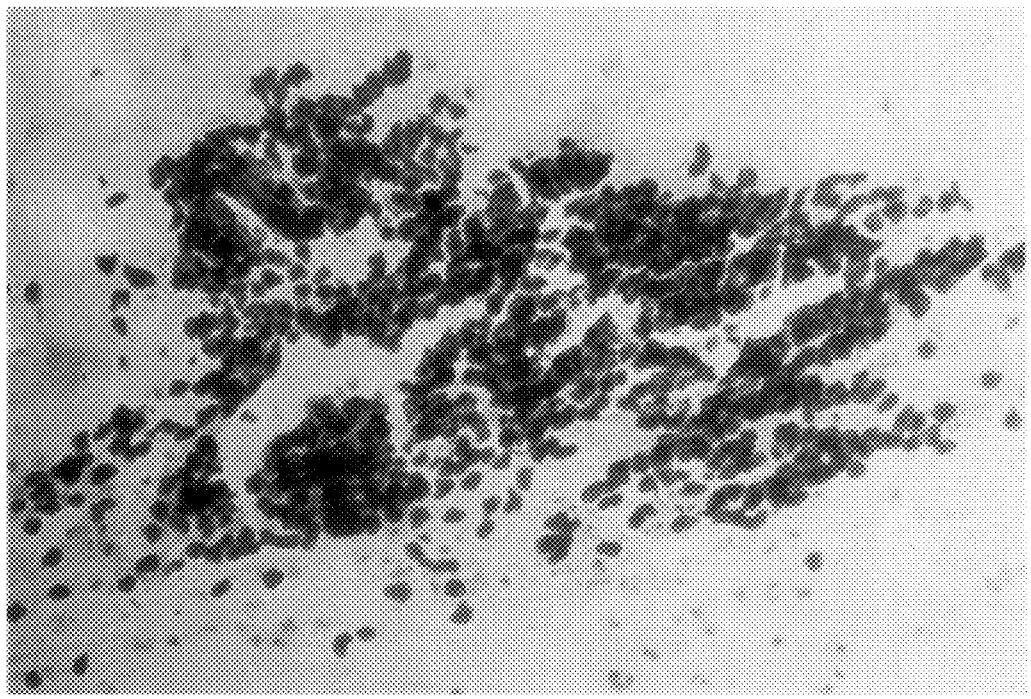
FIG. 12. Photomicrograph confirming production of BDNF protein following injection of liposome-BDNF cDNA complex (1:3 ratio) in the dorsal hippocampus of uninjured rats. Protein production is observed in brain cells (note nuclei) two days following injection. (Magnification: 360×).
Figure 13B:
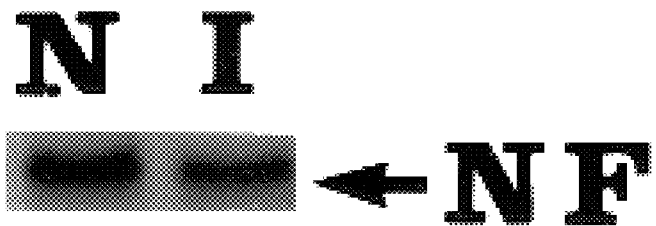
FIG. 13B. Quantitation of neurofilament recovery following BDNF transfection. Immunoreactivity of NF-H following SDS-PAGE and Western analysis. Tissue dissected from parietal cortex ipsilateral to the site of cortical impact. Liposome-BDNF cDNA complex (1:3 ratio) was injected into the ventricle ipsilateral to the injury site immediately after injury. Increased levels of neurofilaments were detected 2-days post-trauma in the BDNF-transfected animal (B) compared to the control animal (C) injected with liposomes alone. (In arbitrary units, 5516 density units were recorded for NF-H level in the injured control animal, and 5862 density units were recorded for NF-H level in the injured BDNF-transfected animal).
Figure 13A:
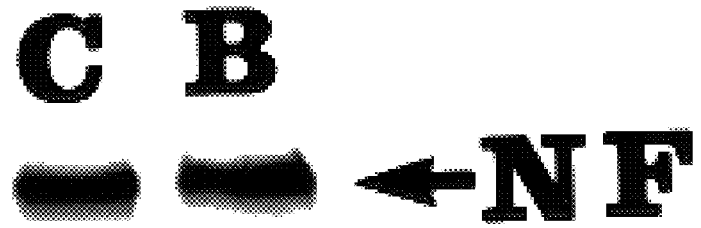
FIG. 13A. Quantitation of neurofilament protein decrease following TBI. Western analysis of neurofilament protein (NF-H) taken from a non-injured (N) and injured (I) rat two days following cortical impact injury. Densitometric scans of the two samples indicated a 38% decrease in NF-H levels following cortical impact injury. (In arbitrary units, 4083 density units were recorded for the non-injured NF level, and 2614 density units were recorded for the injured NF level).

Employing a pUC19 based plasmid, rat BDNF cDNA was subcloned into a unique NotI site under the control of the CMV promoter. DNA for BDNF was complexed with liposomes and transfected into primary septo-hippocampal cell cultures one day after depolarization injury (6.0 min depolarization with 60 mM KCl and the presence of 2.8 mM $Ca^{++}$) (FIG. 11A and FIG. 11B). Three days after depolarization injury, Western blot and immunohistochemical analyses detected significant loss (42% of NF-M and NF-H proteins (Sternberger SMI 31 antibody) in untreated cultures (FIG. 13A and FIG. 13B). However, densitometric scanning of Western blot data indicated that BDNF transfection produced a two-fold increase in NF-M/NF-H three days following injury as compared to untreated cultures. Immunohistochemical studies also detected enhanced NF-M/NF-H immunolabeling in injured neurons following BDNF transfection as compared to untransfected, injured controls. Thus, BDNF gene transfection may be useful as a therapeutic tool for blunting neurofilament loss associated with injury to central nervous system neurons.

EXAMPLE 17

BDNF TRANSFECTION RESCUES NF IN INJURED ANIMALS

To demonstrate the effects of TBI on levels of neurofilament protein in vivo, NF-H levels were determined in animals following TBI using SDS-PAGE and Western analysis. FIG. 13A shows the decrease in NF-H levels which occur as a result of TBI. Tissue was dissected from the parietal cortex ipsilateral to the site of cortical impact. Two days following cortical impact injury, a substantial loss of NF-H protein was detected in the injured (I) rat compared to the non-injured (N) control. Densitometric scans of the two samples indicated a 38% decrease in NF-H levels following cortical impact injury. (In arbitrary units, 4083 density units were recorded for the non-injured NF level, and 2614 density units were recorded for the injured NF level).

To demonstrate the successful rescue of NF-H levels in vivo after the liposome-cDNA transfection methods of the present invention, neurofilament recovery was determined by following the immunoreactivity of NF-H using SDS-PAGE and Western analysis. Tissue was dissected from the parietal cortex ipsilateral to the site of cortical impact as in FIG. 13A. Compared to the control animal (C) which received liposomes alone, the animal transfected with the liposome-BDNF cDNA complex (1:3) ratio) (B) showed a significant restoration of NF-H protein two days after injury. In both cases, injections were made into the ventricle ipsilateral to the injury site immediately after injury. An 8% increase in NF-H was detected 2-days post-trauma in the BDNF-transfected animal. (By densitometric scans, arbitrary units of 5516 and 5862 density units were recorded for NF-H level in the injured control, and the injured BDNF-transfected animal, respectively.

EXAMPLE 18

GENERAL METHODS

1. β-Galactosidase Activity

β-Gal activity is visualized in vivo by histochemical staining using 5-bromo-4-chloro-3-indolyl-β-D-galactopyranoside (X-Gal). Culture wells are washed with phosphate-buffered saline (PBS) and fixed with 0.5 ml containing 2% (v/v) paraformaldehyde and 0.2% glutaraldehyde in $H_2O$ for 5 min at 4° C. Cells are rinsed again with PBS and then stained with 0.5 ml per well of the following solution: 7 mM $Na_2HPO_4$, 23 mM $NaH_2PO_4$, 1.3 mM $MgCl_2$, 3 mM $K_3Fe(CN)_6$, 3mM $K_4Fe(CN)_6$ and 1 mg/ml X-Gal (diluted from a 40 mg/ml stock solution in dimethylformamide). Cells expressing β-Gal are stained blue after incubation at room temperature overnight.

2. mRNA Assessments

Cells grown in culture are lysed by adding 0.2 ml of RNAzol B (Cinna/Biotec Laboratories, Inc.) per $10^6$ cells. The RNA is solubilized by passing the lysate several times through a pipette. After adding 0.2 ml chloroform per 2 ml, the homogenate is incubated at 4° C. for 15 min, and the aqueous phase containing the RNA is transferred to a fresh tube. The supernatant is removed after centrifugation (12, 000×g) for 15 min at 4° C. RNA pellets are washed with 75% ethanol, dried briefly and re-suspended in RNase-free water.

For in vivo studies, hippocampal tissue around injection sites and/or other loci is dissected at 4° C. and homogenized with RNAzol B (2 ml/100 mg) by a motorized Teflon™ pestle homogenizer (10 up-and-down stokes). Methods are then similar to those employed for in vitro studies.

3. Reverse Transcription-Polymerase Chain Reaction (RT-PCR™)

Reverse transcription is performed using oligo (dt) as primers and M-MLV reverse transcriptase (Perkin-Elmer, Norwalk, Conn.). Twenty μg of total RNA from each sample is used for cDNA synthesis. The reaction is carried out at 42° C. for 2 hours using 20 units of recombinant reverse transcriptase devoid of phenol, then with chloroform, followed by precipitation with ethanol. The cDNA is dissolved in 50 μl of TE buffer.

For PCR™, two pairs of forward and reverse primers for BDNF and NGF are used. The sequence of the BDNF/5 primer is 5'-GCAAACATGTCTATGAGGGT-3' (SEQ ID NO:1) and BDNF/3 is 5'-GGTCAGTGTACATACACAGG-3' (SEQ ID NO:2); the sequence NGF/5 primer is 5'-GGCATGCTGGACCCAAGCTC-3' (SEQ ID NO:3) and NGF/3 is 5'-GCGCTTGCTCCGGTGAGTCC-3' (SEQ ID NO:4) (Giordano et al., 1992). 2 μl cDNA and 40 pmol of primer are used for PCR™. PCR™ is carried out in a programmable heating block (Perkin-Elmer) using cycles consisting of denaturation at 95° C. for 1 min, followed by annealing at 55° C. for 1 min and cDNA extension at 72° C. for 2 min.

After amplification, the samples electrophoresed on 1.5% agarose gel. The gels are stained with ethidium bromide and photographed under UV light. The intensity of PCR™ product bands are quantitated by a computer-assisted, linear-scanning densitometer in reflectance mode (Hoefer Scientific Instruments, San Francisco, Calif.).

Since previous studies indicated that β-actin mRNA did not change in the inventors' injury model (Yang et al., 1993), β-actin mRNA is utilized in the same RNA preparation as one internal control for RT-PCR. The sequence for the forward primer is 5'-CCTTCCTGGGCATGGAGTCCTG-3' (SEQ ID NO:5). The sequence of the reverse primer is 5-GGAGCAATGATCTTGATCTTC-3' (SEQ ID NO:6). To check for the possibility of DNA contamination during RNA preparation, the same RNA samples are included without performing the reverse transcription procedure. This control RNA preparation undergoes the same PCR™ process with the sample from the RT product.

4. In Situ Hybridization

Cells are treated with 0.25% trypsin for 5 min at 37° C. The cell suspensions are transferred to poly-L-lysine-coated slides which are fixed with 4% paraformaldehyde for 20 min. After washing with PBS, the slides are dried with increasing gradients of ethanol and store at −80° C. for future in situ hybridization. Rats are perfused intracardially with 120 ml of saline at 40 ml/min, followed with 200 ml of fixative A (0.8 g NaOH, 8 g paraformaldehyde, 1.64 g sodium acetate in 200 ml distilled $H_2O$, pH 6.5) at 20 ml/min, followed by fixative B (1.4 g NaOH, 14 g paraformaldehyde, 13.35 g borax, pH 9.5). Brains are cryoprotected in 10% sucrose-fixative overnight at 4° C. Coronal sections (15μ) are prepared and mount on subbed poly-L-lysine-coated slides and store at −80° C. for in situ hybridization.

Slides are dried overnight and subjected to 0.001% proteinase K digestion at 37° C. for 20 min, then immersed in 0.1 M triethanolamine (TEA) with 0.25% acid anhydride for 10 min. Subsequent dehydration is carried out sequentially in 50, 70, 95 and 100% ethanol (3 min each). The hybridization is performed with a $^{33}$P-labeled cRNA probe (107 cpm/ml) overnight at 55° C. The cRNA probe is obtained from the cDNA clone in pKS vector using T7 or T3 RNA polymerase (Simmons et al., 1989). After hybridization, the slides are washed sequentially in 2×, 1×, 0.2×, 0.1×SSC at 43° C. and dehydrated in 50%, 70%, 95%, and 100% ethanol (3 min each). Brain slides are exposed to Kodak (Rochester, N.Y.) XAR-5 film overnight. After film development, the slides are processed by emulsion autoradiography. After emulsion film development, slides are counterstained with hematoxylin. After dehydration and mounting, slides are examined by dark-field microscopy.

Importantly, the inventors have subjected in situ hybridization slides to DNAse treatment to exclude possible hybridization between the antisense probe and the plasmid cDNA construct.

5. Protein Assay

Proteins are determined using antibodies for NGF, $p75^{NGFR}$, $p140^{trkA}$, $p145^{trkB}$ (Hutton et al., 1992), and a monoclonal antibody (clone 27/21) specific for rat and mouse β (2.5S) NGF that is also suitable for ELISA determinations if NGF proteins in brain tissue. Receptor antibodies are made to synthetic peptide segments on the different neurotrophin receptors and allow determination of different trks as well as differential staining of full and truncated versions of the different trks.

6. Immunohistochemistry

Cells are fixed in tissue culture wells by the gentle 1:1 addition of 8% paraformaldehyde in 0.12 M PBS (pH 7.3) for 20 min. After brief wash with PBS, the cells are ready to be immunostained. Rats are perfused intracardially with 120 ml of saline and 240 ml of a fixative solution containing 4% paraformaldehyde in 0.12 M phosphate buffered saline (PBS) (pH 7.3). Rat brains are removed and post fixed overnight at 4° C. in 4% paraformaldehyde in 0.12 M phosphate buffer. Coronal sections (15μ) are prepared and mount on subbed poly-L-lysine coated slides.

Cultures are washed with PBS buffer and incubated in normal goat serum (4%) for one hour. Following 3 5-min washes with PBS, the cultures are incubated with Goat anti-Mouse IgG (Chemicon International, Inc., Temecula, Calif.) antibodies (dilution 1:100) for two hours at room temperature. The cultures are quenched for endogenous peroxidase with 0.03% of $H_2O_2$ in methanol for 30 min at room temperature. After 35-min washes with PBS, the cultures are incubated with Avidin-Peroxidase solution (Vector Lab, Burlingame, Calif.) for one hour at room temperature. Following 35-min washes with PBS, cultures are pre-incubated with diaminobenzidine tetrahydrochloride (DAB) (Vector Lab) and 0.006% $H_2O_2$ for 10 min.

Cultures are washed with distilled water and counterstained with hematoxylin. After dehydration and mounting, cultures are studied by light microscopy on an inverted (tissue culture) microscope. Similar procedures are used for $p75^{NGFR}$, $p140^{trkA}$ and $p145^{trkB}$ receptor immunohistochemistry (Turner and Perez-Polo, 1993). For immunostaining of brain slices, coronal sections are mounted on slides and the same protocol is followed except that rinses are 5 times for 5-min each to minimize background staining.

7. ELISA

For in vitro studies, cells are treated with lysis buffer and extracted on ice for 10 min. The extractions are centrifuged at 20,000×g for 15 min at 4° C. The supernatant is assayed for protein using the Bradford method with a BSA standard (Ausubel et al., 1993). The samples are aliquoted and stored at −80° C. for later ELISA. For in vivo studies, tissue from the hippocampus and other brain regions are dissected at 4° C. and homogenized in ice-cold buffer (50 mM Tris; 2 mM EDTA; 2 mM DTT; 100 μM leupeptin; pH7.5) by a motorized Teflon pestle homogenizer (10 up-and-down strokes). The homogenates are then processed as described above for later ELISA.

8. Antibody-Sandwich ELISA

Specific anti-NGF or anti-BDNF antibodies are diluted to a final concentration of 0.2 to 10 μg/ml. The optimal concentrations of anti-NGF or anti-BDNF antibodies and the conjugate necessary to detect the sample NGF or BDNF are determined by criss-cross serial dilution analysis. After final concentrations of anti-NGF or anti-BDNF antibodies are determined, wells of a plate are coated with serial concentrations of anti-NGF or anti-BDNF antibodies. The standard NGF and BDNF dilution series are prepared by 1:3 dilution of stock NGF and BDNF solutions.

After tissue homogenization, sample homogenates are diluted in blocking buffer. 50 μl aliquots of the diluted homogenate and standard NGF and BDNF dilutions are added to the antibody-coated wells and incubated two hours at room temperature. After washing the plate with water and blocking buffer, a 50 μl antibody-alkaline phosphatase conjugate is added to each well and incubated for two hours at room temperature. After another wash with water and blocking buffer, 75 μl of NPP substrate solution is added to each well followed by incubation for 1 hour at room temperature. After color development, the plate is read on a microtiter plate reader. The NGF and BDNF concentrations are determined from a standard concentration curve.

9. Biological Assay of Neurotrophin Activity

Biological assays for NGF induced differentiation are performed by assay of NGF activity in conditioned media, cells or tissues. Assays employ both the rat pheochromocytoma (PC12) cell line (Greene and Tischler, 1976) and nodose and dorsal root ganglia explants (Lindsay and Rohrer, 1985). The assays score neurite outgrowth and differentiation as seen in increased length and complexity of neurites. Assays employ standardization of neurotrophic dose-response curves as well as confirmation of blockade by appropriate antisera. PC12 cells are photographed and evaluated for morphological differentiation five days after treatment with appropriate experimental media. Nodose and dorsal root ganglia explants from embryonic day 8 are overlaid with the experimental media. 24–48 hours later, the ganglia are photographed and scored for neurite outgrowth (Perez-Polo, 1987).

10. Calculation of Transfection Efficiency

Transformation efficiency in β-Gal transfected cells is calculated after X-Gal staining and hematoxylin counterstaining by determining the total cell number and the number of β-Gal positive cells in at least 3 randomly chosen non-overlapping fields per well. Transformation efficiency is expressed as a percentage of β-Gal positive cells to total cells. X-Gal staining offers a distinct advantage over other procedures that measure enzyme activity of the total population of transfected cells (e.g., luciferase-transfection quantitation assays) rather than enzyme activity within individual cells which can be visualized and counted.

Transformation efficiency in NGF-and BDNF-transfected cells will first be estimated using quantitative RT-PCR™. Studies have shown that such a qualitative comparison was sufficient for determining the relative optimal transformation efficiency when several cDNA:liposomes ratios are compared. In order to determine the precise transfection efficiency of an optimal ratio, in situ hybridization was combined with hematoxylin counterstaining to determine the total cell number and the number of successfully transfected cells (cells expressing NGF and BDNF mRNA at greater then background levels) in at least 3 randomly chosen non-overlapping fields per well. Transformation efficiency is expressed as a percentage of successfully transfected cells to total cells.

Transfection efficiency for in vivo studies is calculated on the basis of cell counts made in 2.0 mm$^2$ area units of coronal tissue sections adjacent to the site of injection. The total area sampled depends upon the extent of transfection observed. As stated for in vitro studies, β-Gal transfection efficiency studies employ X-Gal staining and hematoxylin counterstaining to determine the total cell number and the number of β-Gal positive cells. In studies of NGF and BDNF, in situ hybridization is combined with hematoxylin counterstaining to determine the total number and the number of successfully transfected cells. Transformation efficiency is expressed as a percentage of successfully transfected cells to total cells.

11. Histopathological Assessment

In general, histological assessments are done in conjunction with in situ and immunohistochemical analyses. Hemorrhage and necrosis is detected by conventional hematoxylin and eosin (H&E) staining. Edema formation (extravasated blood plasma) is monitored by immunostaining for plasma albumin, and then comparing this pattern to the hemorrhage in the adjacent serial H&E-stained section. Viable neurons in brain grey matter are visualized by conventional Nissel stain. Axonal injury is determined by Palmgren's silver impregnation method for the presence of reactive axonal swellings (retraction balls).

Macrophages are detected using commercially-available monoclonal antibodies (ED1, ED2, ED3) specific for rat. Astroglial reaction is determined using Glial fibrillary acidic protein (GFAP) employing a mix of commercially-available mouse monoclonal antibodies.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following literature citations as well as those cited above are incorporated in pertinent part by reference herein for the reasons cited in the above text.

U.S. Pat. No. 4,518,584.

U.S. Pat. No. 5,168,050.

Adams et al., "Head injury in man and experimental animals," *Acta Neurochir.*, 32:15–30, 1983.

Alderson et al., "Brain derived neurotrophic factor increases survival and differentiated functions of rat septal cholinergic neurons," *Neuron*, 5:297–306, 1990.

Arai et al., "A brief period of hypoxia causes proteolysis of cytoskeletal proteins in hippocampal slices," *Brain Res.*, 555:276–280, 1991.

Arai et al., "Calpain inhibitors improve the recovery of synaptic transmission from hypoxia in hippocampal slices," *Brain Res.*, 532:63–68, 1990.

Ausubel et al., "Current Protocols in Molecular Biology," Vol. 2., John Wiley and Sons, New York., 1993.

Balazsovits et al., "Analysis of the effect of liposome encapsulation on the vesicant properties, acute and cardiac toxicities, and antitumor efficacy of doxorubicin," *Cancer Chemother. Pharmacol.*, 23:81–86, 1989.

Balentine, J. D., "Hypotheses in spinal cord trauma research, In: Central Nervous System Status Report. D. Becker and J. T. Povlishock (ed). National Institute of Neurological Communicative Disorders and Stroke, National Institutes of Health: Washington, D.C., pp. 455–461, 1985.

Banik et al., "Degradation of cytoskeletal proteins in experimental spinal cord injury," *Neurochem. Res.*, 7:1465–1475, 1992.

Barker and Murphy, "The NGF receptor—a multicomponent system that mediates the actions of the neurotrophin family of proteins," *Mol. Cell Biochem.*, 110:1–15, 1992.

Barinega, M., "Solving the delivery puzzle," *Science*, 264:773, 1994.

Battleman et al., "HSV1 vector-mediated gene transfer of the human nerve growth factor receptor $p75^{NGFR}$ defines high-affinity NGF binding," *J. Neurosci.*, 13:941–951, 1993.

Beattie et al., "Experimental spinal cord injury: Strategies for acute and chronic intervention based on anatomic, physiological and behavioral studies, In: *Pharmacological Approaches to the Treatment of Brain and Spinal Cord Injury*. D. G. Stein and B. S. Sabel (eds). Plenum Press: New York, pp. 43–74, 1988.

Bradford, M. M., "A rapid and sensitive method for the quantification of microgram quantities of protein utilizing the principle of protein-dye binding," *Anal. Biochem.*, 72:238–259, 1976.

Breakefield and DeLuca, "Herpes simplex virus for gene delivery to neurons," *New Biol.*, 3:203–218, 1991.

Brewer and Cotman, "Survival and growth of hippocampal neurons in defined medium at low density: Advantages of a sandwich culture technique or low oxygen," *Brain Res.*, 494:65–74, 1989.

Capecchi, M. R., "High efficiency transformation by direct microinjection of DNA into cultured mammalian cells," *Cell*, 22(2):479–488, 1980.

Caramia et al., "Experimental analysis of the mouse submaxillary salivary gland in relationship to its nerve growth factor content," *Endocrinology*, 70:915–922, 1962.

Chan, P. H., "Antioxidant-dependent amelioration of brain injury: Role of CuZn-superoxide dismutase," *J. Neurotrauma*, 9(suppl 2):S417–424, 1992.

Chang and Brenner, *Focus*, 6(4):66–69, 1988.

Chao et al., "Distinctive functions of NGF receptors," *J. Neurochem.*, 61: S119, 1993.

Chin et al., "The proteolytic digestion of ox neurofilament with trypsin and α-chymotrypsin," *Biochem. J.*, 215:239–252, 1983.

Clapp, D. W., "Somatic gene therapy into hematopoietic cells: current status and future implication," *Clin. Perinatol.*, 20:155–168, 1993.

Clinton et al., "Post-traumatic Alzheimer's disease: preponderance of a single plague type," *Neuropath. Appl. Neurobiol.*, 17:69–74, 1991.

Coune, A., "Liposomes as drug delivery system in the treatment of infectious diseases: Potential applications and clinical experience," *Infection*, 16:141–147, 1988.

Culver et al., "In vivo gene transfer with retroviral vector-producer cells for treatment of experimental brain tumors," *Science*, 256:1550–1552, 1992.

Curiel et al., "Adenovirus enhancement of transferrin-polylysine-mediated gene delivery," *Proc. Natl. Acad. Sci. USA*, 88:8850–8854, 1991.

Danos and Heard, "Recombinant retroviruses as tools for gene transfer to somatic cells," *Bone Marrow Transplant*, 9:131–138, 1992.

Dautingy et al., "The large neurofilament subunit (NF-H) of the rat: cDNA cloning and in situ detection. *Biochem. Biophys. Res. Commun.*, 154:1099–1106, 1988.

Debs et al., "Regulation of gene expression in vivo by liposome-mediated delivery of a purified transcription factor," *J. Biol. Chem.*, 265(18):10189–10192, 1990.

Debs et al., "Targeting of anti-Thy 1.1 monoclonal antibody conjugated liposomes in Thy 1.1 mice after intravenous administration," *Biochem. Biophys. Acta*, 901:183–190, 1987.

Dellig and Seliger, "Gene transfer into brain tumor cell lines: reporter gene expression using various cellular and viral promoters," *J. Neurosci. Res.*, 26(3):390–396, 1990.

Denton et al., "Production and characterization of neurotrophin antibodies for immunohistochemistry," *Soc. Neurosci. Abstr.*, 19:255, 1993.

DeWitt et al., "Effects of traumatic brain injury on hippocampal physiology in vitro and cortical DC potentials in vivo," *J CBF & Metab.*, 9(supp 1):S93, 1989.

Dixon et al., "A controlled cortical impact model of traumatic brain injury in the rat," *J. Neurosci. Methods*, 39:253–262, 1991.

Dixon et al., "A fluid percussion model of experimental brain injury in the rat," *J. Neurosurg.*, 67:110–119, 1987.

Dixon et al., "Mechanisms of mild traumatic brain injury," *J. Head Trauma Rehab.*, 8(3):21–32, 1993.

Dragunow and Robertson, "Generalized seizures induce c-fos protein(s) in mammalian neurons," *Neurosci. Lett.*, 82:157–161, 1987.

Drazba and Ralston, "Expression of *E. coli* β-galactosidase in low density cultures of hippocampal neurons," Lab of Neurobiology, NINDS, NIH, Bethesda, Md. 20892, 1993.

Eglitis and Anderson, "Retroviral vectors for introduction of genes into mammalian cells," *Biotechniques*, 6:608–614, 1988.

Faller and Baltimore, "Liposome encapsulation of retrovirus allows efficient superinfection of resistant cell lines," *J. Virol.*, 49(1):269–272, 1984.

Fang et al., "Tissue-specific activity of heterologous viral promoters in primary rat hepatocytes and Hep G2 cells," *Hepatology*, 10:781–787, 1989.

Felgner et al., "Lipofection: A highly efficient, lipid-mediated DNA-transfection procedure," *Proc. Natl. Acad. Sci. USA*, 84:7413–7417, 1987.

Fineman et al., "Concessive brain injury is associated with a prolonged accumulation of calcium: a $^{45}Ca$ autoradiographic study," *Brain Res.*, 624:94–102, 1993.

Fischer et al., "Amelioration of cholinergic neuron atrophy and spatial memory impairment in aged rats by nerve growth factor," *Nature*, 329:65–68, 1987.

Friedmann and Ginnah, "Gene therapy for disorders of the nervous system," *Tibitech*, 11:156–162, 1993.

Fromm et al., "Expression of genes transferred into monocot and dicot plant cells by electroporation," *Proc. Natl. Acad. Sci. USA*, 82:5824–5828, 1985.

Gage, et al., "Grafting genetically modified cells to the brain, possibilities for the future," *Neuroscience* 23:795–807, 1987.

Gelinas and Temin, "Nondefective spleen necrosis virus-derived vectors define the upper size limit for packaging reticuloendotheliosis viruses," *Proc. Natl. Acad. Sci. USA*, 83:9211–9215, 1986.

Gennarelli et al., "Axonal injury in the optic nerve: A model stimulating diffuse axonal injury in the brain," *J. Neurosurg.*, 67:244–253, 1989.

Ghosh et al., *Science* 263:1618, 1994.

Giordano et al., "Isolation of a population of transiently transfected quiescent and senescent cells by magnetic affinity cell sorting," *Exp. Cell Res.*, 992:993–997, 1991.

Girodano et al., "Thyroid hormone regulation of NGF, NT-3 and BDNF RNA in the adult rat brain," *Molecular Brain Research*, 16:239–245, 1992.

Gorman et al., "Analysis of acetylcholine release following concussive brain injury in the rat," *J. Neurotrauma*, 6:203–207, 1989.

Graham and Prevec, "Manipulation of adenovirus vectors," In: Murray, E. J., eds. *Methods in Molecular Biology: Gene Transfer and Expression Protocols*, Clinton, N.J.: The Human Press Inc., 109–128, 1991.

Graham and VanDerEb, "A new technique for the assay of infectivity of human adenovirus 5 DNA," *Virology*, 52:456–467, 1973.

Greene and Tischler, "Establishment of a noradrenergic clonal line of rat adrenal pheochromocytoma cells which respond to NGF," *Proc. Natl. Acad. Sci. USA*, 73:2424–2428, 1976.

Greene and Tischler, "PC12 pheochromocytoma cultures in neurobiological research," *Adv. Cell Neurobiol.*, 373–414, 1982.

Hafti, F., "Nerve growth factor promotes survival of septal cholinergic neurons after fimbrial transections," *J. Neurosci*, 8:2155–2162, 1986.

Hall et al., "Biochemistry and pharmacology of lipid antioxidants in acute brain and spinal cord injury," *J. Neurotrauma*, 9(suppl 2):S425–442, 1992.

Hamm et al., "Cognitive deficits following traumatic brain injury produced by controlled cortical impact," *J. Neurotrauma*, 9:11–20, 1992.

Hayes et al., "Neurotransmitter mediated mechanisms of traumatic brain injury—acetylcholine and excitatory amino acids; Central Nervous System Status Report: 1991," *J. Neurotrauma.*, 9: S173–S187, 1992.

Heath et al., "Liposome-mediate delivery of pteridine antifolates to cells in vitro: potency of methotrexate, and its a and y substituents," *Biochem. Biophys. Acta*, 862:72–80, 1986.

Hoffman and Lasek, "The slow component of axonal transport: Identification of major structural polypeptides of the axon and their generality among mammalian neurons," *J. Cell Biol.*, 66:351–366, 1975.

Holt et al., "Lipofection of cDNAs in the embryonic vertebrae central nervous system," *Neuron*, 4:203–214, 1990.

Horwitz, M. S., "Adenoviridae and their replication," In: B. N. Fields and D. M. Knipe (Eds.), *Fields Neurology*, 2nd ed., Raven, N.Y., pp. 1679–1721, 1990.

Huang et al., "Introduction of a foreign gene (*E. coli* lacZ) into rat neostriatal neurons using herpes simplex virus mutants: A light and electron microscopic study," *Exp. Neurol.*, 115:303–316, 1992.

Imaizumi et al., "Liposome-entrapped superoxide dismutase ameliorates infarct volume in focal cerebral ischemia," *Acta Neurochurgia Suppl.*, 51:236–239, 1990.

Imaizumi et al., "Liposome-entrapped superoxide dismutase reduces cerebral infarction in cerebral ischemia in rats," *Stroke*, 21:1312–1317, 1990.

Inuzuka et al., "Changes in the concentrations of cerebral proteins following occlusion of the middle cerebral artery in rats," *Stroke*, 21:917–922, 1990b.

Inuzuka et al., "Suppressive effect of E-64c o ischemic degradation of cerebral proteins following occlusion of the middle cerebral artery in rats. *Brain Res.*, 526:177–179, 1990a.

Jenkins et al., "Increased vulnerability of the mildly traumatized brain to cerebral ischemia: the use of controlled secondary ischemia as a research tool to identify common or different mechanisms contributing to mechanical and ischemic brain injury," *Brain Res.*, 477:211–234, 1989.

Jiang et al., "Moderate hypothermia reduces blood-brain barrier disruption following traumatic brain injury in the rat," *Acta Neuropathologica*, 84:495–500, 1992.

Jiao et al., "Persistence of plasma DNA and expression in rat brain cells in vivo," *Exp. Neurol.*, 115:400–413, 1992.

Johnson, G., "Chemical neurotoxins as denervation tools in neurobiology," *Ann. Rev. Neurosci.*, 3:169–187, 1980.

Johnson et al., "Degradation of microtubule-associated protein 2 (MAP2) and brain spectrin by calpain: A comparative study," *J. Neurochem.*, 56:1630–1638, 1991.

Johnson et al., "Effects of gene transfer into cultured CNS neurons with a replication-defective herpes simplex virus type 1 vector," *Mol. Brain res.*, 12:95–102, 1992.

Julien and Mushynski, "Multiple phosphorylation sites in mammalian neurofilament polypeptides," *J. Biol. Chem.*, 257:10467–10470, 1982.

Kaech et al., "Expression of *E. coli* β-galactosidase in low-density cultures of hippocampal neurons," *Soc. Neurosci. Abstr.*, 19:1746, 1993.

Kaku et al., "Alterations of a 200 kDa neurofilament in the rat hippocampus after forebrain ischemia," *J. Cereb. Blood Flow Metab.*, 13:402–408, 1993.

Kamakura et al., "Calcium-activated neutral protease in the peripheral nerve, which requires $\mu$M order $Ca^{2+}$, and its effect on the neurofilament triplet, *J. Neurosci. Res.*, 13:391–403, 1985.

Kawaja et al., "Somatic gene transfer of nerve growth factors promotes the survival of axotomized septal neurons and the regeneration of their axons in adult rats," *J. Neurosci.*, 12:2849–2864, 1992.

Kromer, L. F., "Nerve growth factor treatment after brain injury prevents neuronal death," *Science*, 235:214–216, 1987.

Kudo et al., "Neuropathological changes in the gerbil brain after chronic hypoperfusion," *Stroke*, 24:259–265, 1993.

Kyte & Doolittle. *J. Mol. Biol.* 157:105–132, 1982.

la Gal la Salle et al., "An adenovirus vector for gene transfer into neurons and glia in the brain," *Science*, 259:988–990, 1993.

Lee et al., "Inhibition of proteolysis protects hippocampal neurons from ischemia," *Proc. Natl. Acad. Sci. USA*, 88:7233–7237, 1991.

Levi-Montalcini and Cohen, "Effects of the extract of the mouse submaxillary salivary glands on the sympathetic system of mammals," *Ann. NY Acad. Sci.*, 85:324–341, 1960.

Li et al., "Gene transfer in primary cultures of human hepatocytes," *In Vitro Cell Dev. Biol.*, 28A:373–375, 1992.

Lindsay and Rohrer, "Placodal sensory neurons in culture: Nodose ganglion neurons are unresponsive to NGF, lack NGF receptors but are supported by a liver-derived neurotrophic factor," *Dev. Biol.*, 112:30–48, 1985.

Lindsay, R. M., "Brain-derived neurotrophic factor an NGF-related neurotrophin. In: *Neurotrophic factor* Fallon J. A., Loughlin, S. E., eds. New York, Academic Press 257–284, 1993.

Lopez-Berestein et al., Liposomal amphotericin B for the treatment of systemic fungal infections in patients with cancer: A preliminary study," *J. Infect. Diseases*, 151(4):704–710, 1985.

Lycke et al., "Herpes simplex virus infection of the human sensory neuron: An electron microscopy study," *Arch. Virol.*, 101:87–104, 1988.

Lyeth et al., "Prolonged memory impairment in the absence of hippocampal cell death following traumatic brain injury in the rat," *Brain Res.*, 526:249–258, 1990.

MacGregor and Caskey, "Construction of plasmids that express *E. coli* β-galactosidase in mammalian cells," *Nucl. Acids Res.*, 17(6):2365, 1989.

Machida et al., "NGF induction of the gene encoding the protease transin accompanies neuronal differentiation in PC12 cells," *Neuron*, 2:1587–1596, 1989.

Maisonpierre et al., "NT-3 BDNF and NGF in the developing rat nervous system: parallel as well as reciprocal patterns of expression," *Neuron*, 5:501–509, 1990b.

Maniatis et al., Molecular Cloning: A Laboratory Manual, Cold Spring Harbor Laboratory, Cold Spring Harbor, N.Y. 1982.

Meaney et al., "The significance of impact velocity in the production of axonal injury in the contralateral cerebral cortex using rigid indentation," *J. Neurotrauma*, 9:393, 1992.

Meilio et al., "Increased production of the trkB protein tyrosine kinase receptor after brain insults," *Neuron*, 10:151–164, 1993.

Mellgren and Murachi, *Intracellular Calcium-Dependent Proteolysis*. CRC Press, Inc.: Boca Raton, Fla., 1990.

Montero and Hefti, "Rescue of lesioned septal cholinergic neurons by nerve growth factor: specificity and requirement for chronic treatment," *J. Neurosci.*, 8:2986–2999, 1988.

Mori and Fukatsu, "Anticonvulsant effect of DN-1417, a derivative of thyrotropin-releasing hormone, and liposome entrapped DN-1417, on amygdaloid-kindled rats," *Epilepsia*, 33(6):994–1000, 1992.

Morse et al., "Brain-derived neurotrophic factor (BDNF) prevents the degeneration of medical septal cholinergic neurons following fimbria transection," *J. Neurosci.*, 13(10):4146–4156, 1993.

Mortimer et al., "Head trauma as a risk factor for Alzheimer's disease: a collaborative re-analysis of case-control studies," *Int. J. Epidemiol*, 20(suppl 2):528–535, 1991.

Muller et al., "Laboratory methods: Efficient transfection and expression of heterologous genes in PC12 cells," *DNA Cell Biol.*, 9(3):221–229, 1990.

Nabel et al., "Gene transfer in vivo with DNA-liposome complexes: safety and acute toxicity in mice," *Human Gene Ther.*, 3:267–275, 1992a.

Nabel et al., "Gene transfer in vivo with DNA-liposome complexes: lack of autoimmunity and gonadal localizations," *Human Gene Ther.*, 3:649–656, 1992b.

Nakamura et al., "Differential distribution of 68 kD and 200 kD neurofilament proteins in the gerbil hippocampus and their early distributional changes following transient forebrain ischemia," *Exp. Brain Res.*, 89:31–39, 1992.

Nicolau and Gersonde, "Incorporation of inositol hexaphosphate into intact red blood cells," *Naturwissenschaften*, 66:563–566, 1979.

Nistico et al., "NGF restores decrease in catalase activity & increases superoxide dismutase & GSH peroxidase activity in the brain of aged rats," *Fice Rad. -Biol. Mod.*, 12:177–181, 1992.

Nixon and Marotta, "Degradation of neurofilament proteins by purified human brain cathepsin D.," *J. Neurochem.*, 43:507–516, 1984.

Nixon and Sihang, "Neurofilament phosphorylation: A new look at regulation and function," *TINS*, 14:501–506, 1991.

Oliver et al., "The protease inhibitor leupeptin interferes with the development of LTP in hippocampal slices," *Brain Res.*, 505:233, 238, 1989.

Ono et al., "Plasmid DNAs directly injected into mouse brain with lipofectin can be incorporated and expressed by brain cells," *Neuroscience Letters*, 117:259–263, 1990.

Palmer et al., "Traumatic brain injury-induced excitotoxicity assessed in a controlled impact model," *J. Neurochem.*, 61:2015–2023, 1993.

Pant, H. C., "Dephosphorylation of neurofilament proteins enhances their susceptibility to degradation by calpain," *Biochem. J.*, 256:665–668, 1988.

Perez-Polo, J. R. (ed.), *Handbook of Nervous System Factors*, CRC Press, Inc., Boca Raton, Fla., 1987.

Perlmutter et al., "The ultrastructural localization of calcium activated protease 'Calpain' in rat brain," *Synapse*, 2:79–88, 1988.

Phillips et al., "BDNF mRNA is decreased in the hippocampus of individual with Alzheimer's disease," *Neuron*, 7:695–702, 1991.

Pietrini et al., "Panencephalopathic type of Cruetzfeld-Jacob disease with neuropathological features similar to Pick's disease," *Clin. Neuropathol.*, 12:1–6, 1993.

Pikul et al., "In vitro killing of melanoma by liposome-delivered intracellular irradiation," *Arch. Surg.*, 122:1417–1420, 1987.

Povlishock, J. T., "Pathobiology of traumatically induced axonal injury in animals and man," *Ann. Emerg. Med.*, 22:980–986, 1993.

Ram et al., "In situ retroviral-mediated gene transfer for the treatment of brain tumors in rats," *Cancer Res.*, 53:83–88, 1993.

Richardson and Ebendal, "Nerve growth activities in rat peripheral nerve," *Brain Res.*, 246:57–64, 1982.

Roberts et al., "β/A4 amyloid protein deposition in brain after head trauma," *Lancet*, 338:1422–1423, 1991.

Roessler and Davidson, "Direct plasmid mediated transfection of adult murine brain cells in vivo using cationic liposomes," *Neurosci. Lett.*, 167:5–10, 1994.

Rosenberg et al., "Grafting genetically modified cells to the damaged brain: restorative effects of NGF expression," *Science*, 242:1575–1578, 1988.

Rylett et al., "Acetylcholine synthesis and release following continuous intracerebral administration of NGF in adult and aged Fischer-344 rats," *J. Neurosci.*, 13:3956–3963, 1993.

Sambrook, J., et al. (1989), Molecular Cloning: A Laboratory Manual, Cold Spring Harbor Laboratory, Cold Spring Harbor, N.Y.

Sampath et al., "Effects of NGF on glutathione-peroxidase and catalase, in PC12 cells," *J. Neurochem.*, (submitted) 1993.

Sautter et al., "$GM_1$ ganglioside treatment reduces visual deficits after graded crush on the rat optic nerve," *Brain Res.*, 565:23–33, 1991.

Schlaepfer and Zimmerman, "An immunoblot study of neurofilament degradation in situ and during calcium-activated proteolysis," *J. Neurochem.*, 644:502–509, 1985a.

Schlaepfer and Zimmerman, "Mechanisms underlying the neuronal response to ischemic injury. Calcium-activated proteolysis of neurofilaments," *Prog. Brain Res.*, 63:185–196, 1985b.

Schlaepfer et al., "Persistence of immunoreactive neurofilament protein breakdown products in transected rat sciatic nerve," *J. Neurochem.*, 43:857–864, 1984.

Shaw, G., "Neurofilaments: Abundant but mysterious structures," *Bioessays*, 4:161–166, 1986.

Siman and Noszek, "Excitatory amino acids activate calpain 1 and induce structural protein breakdown in vivo," *Neuron*, 1:279–287, 1988.

Siman et al., "Brain fodrin: Substrate for calpain 1, an endogenous calcium-activated protease," *Proc. Natl. Acad. Sci. USA*, 81:3572–3576, 1984.

Simmons et al., "A complete protocol for in situ hybridization of messenger RNAs in brain and other tissues with radiolabeled single-stranded RNA probes," *J. Histotechnol.*, 12:169–181, 1989.

Sternberger et al., "Aberrant neurofilament phosphorylation in Alzheimer's disease," *Proc. Natl. Acad. Sci. USA*, 82:4274–4276, 1985.

Stewart et al., "Gene transfer in vivo with DNA-liposome complexes: safety and acute toxicity in mice," *Human Gene Ther.*, 3:267–275, 1992.

Storm et al., "Potential pitfalls in in vitro antitumor activity testing of free and liposome-entrapped doxorubicin," *J. Pharm. Sci.*, 77(10):823–830, 1988.

Taft et al., "Hypothermia attenuates the loss of hippocampal microtubule-associated protein 2 (MAP2) following traumatic brain injury," *J. Cereb. Blood Flow Metab.*, 13:796–802, 1993.

Taft et al., "Microtubule-associated protein 2 levels decrease in hippocampus following traumatic brain injury," *J. Neurotrauma*, 9:281–290, 1992.

Teng and Greene, "Depolarization maintains neurites and priming of PC12 cells after nerve growth factor withdrawal," *J. Neurosci.*, 13(7):3124–3135, 1993.

Thompson et al., "Transient promoter activity in primary rat mammary epithelial cells evaluated using particle bombardment gene transfer," *In Vitro Cell Dev. Biol.*, 29A:165–170, 1993.

Tomita et al., "Direct in vivo gene introduction into rat kidney," *Nippon-Rinsho*, 50(12):2874–2878, 1992.

Towbin et al., "Electrophoretic transfer of proteins from polyacrylamide gels to nitrocellulose sheets: Procedure and some applications," *Proc. Natl. Acad. Sci. USA*, 76:4350–4354, 1979.

Troost et al., "Neurofilament and glial alterations in the cerebral cortex in ALS," *Acta Neuropathol.*, 84:664–673, 1992.

Turner et al., "Expression of $p75^{NGFR}$ in the olfactory system following peripheral deafferentation," *Neurorep.* 5:1023–1026, 1993.

Ulrich et al., "Cytoskeletal immunohistochemistry of Alzheimer's dementia and related diseases: A study with monoclonal antibodies," *Pathol. Immunol. Pathol. Res.*, 6:273–283, 1987.

Wagner et al., "Influenza virus hemagglutinin HA-2 N-terminal fusogenic peptides augment gene transfer by transferrin-polylysine DNA complexes: toward a synthetic cirus like gene transfer vehicle," *Proc. Natl. Acad. Sci. USA*, 89:7934–7938, 1992.

Whitson et al., "Controlled cortical impact injury alters amyloid protein precursor levels in rat hippocampus and cortex," J. Neurotrauma Abst., 1994.

Williams and Rylett, "Exogenous nerve growth factor increases the activity of high-affinity choline uptake and choline acetyltransferase in brain of fisher 344 male rats," *J. Neurochem.*, 55:1042–1049, 1990.

Williams et al., "Continuous infusion of nerve growth factor prevents basal forebrain neuronal death after fimbria-fornix transfection," *Proc. Natl. Acad. Sci. USA*, 83:9231–9235, 1986.

Wilson et al., "Biological properties of poliovirus encapsulated in lipid vesicles: antibody resistance and infectivity in virus-resistant cells," *Proc. Natl. Acad. Sci. USA*, 74(8):3471–3475, 1977.

Wilson et al., "The introduction of poliovirus RNA into cells via lipid vesicles (liposomes)," *Cell*, 17:77–84, 1979.

Wolf et al., "Retrovirus mediated gene transfer of β-nerve growth factor into mouse pituitary line AtT-20," *Mol. Biol. Med.*, 5:43–49, 1988.

Wong and Neumann, "Electric field mediated gene transfer," *Biochem. Biophys. Res. Commun.*, 107(2):584–587, 1982.

Wu et al., "Receptor-mediated gene delivery in vivo: partial correction of genetic analbuminemia in Nagase rats," *J. Biol. Chem.*, 266:14338–14342, 1991.

Yaghmai and Povlishock, "Traumatically induced reactive change as visualized through the use of monoclonal antibodies targeted to neurofilament subunits," *J. Neuropathol. Exp. Neurol.*, 51:158–176, 1992.

Yamada et al., "Retrovirus-mediated gene transfer targeted to malignant glioma cells in murine brain," *Jap. J. Cancer Res.*, 83(12):1244–1247, 1992.

Yang et al., "Alterations of protein kinase C in rat hippocampus following traumatic brain injury," *J. Neurotrauma*, 10:287–295, 1993.

Yang et al., "In vivo and in vitro gene transfer to mammalian somatic cells by particle bombardment," *Proc. Natl. Acad. Sci. USA*, 87:9568–9572, 1990.

Yang et al., "Optimizing liposome-mediated gene transfer in primary septo-hippocampal cell cultures," *Neurosci. Lett.*, (In Press), 1994.

Yang et al., "Sustained expression of functional nerve growth factors in primary septo-hippocampal cell cultures by liposome-mediated gene transfer," *Neurosci. Lett.*, 182: this issue, 1994.

Yang et al., "Temporal and regional profile of BDNF and NGF mRNA expression after cortical impact injury in rat brain," 23nd Annual Meeting Society for Neuroscience, Washington, D.C., Nov. 1993, *J. Neurotrauma Abstracts*, 1993.

Yip et al., *J. Neurosci.* 13:3394, 1993.

What is claimed is:

1. A method for treating nerve cells by transfection comprising the steps of:
   (a) selecting a nerve cell tissue site of an animal suffering a traumatic brain or spinal cord injury;
   (b) administering to the cells of said nerve tissue site of said animal by direct injection an effective amount of a composition comprising a nucleic acid segment encoding a neurotrophin, and a liposome comprising at least one cationic lipid; wherein said neurotropin is selected from the group consisting of nerve growth factor (NGF) and brain-derived nerve growth factor (BDNF), and wherein said cells of said nerve tissue site in said animal are transfected with said composition resulting in the transient expression of said neurotrophin in said cells causing a reduction of neuron death or cytoskeletal protein damage in said nerve tissue site.

2. The method of claim 1, wherein said animal is a human.

3. The method of claim 1, wherein the liposome further comprises a phospholipid and wherein the cationic lipid is DOTMA and the phospholipid is DOPE.

4. The method of claim 3, wherein DOTMA and DOPE are in about a 1:1 ratio.

5. The method of claim 1, wherein the nucleic acid segment and the liposome are in a ratio from about 1:1 to about 1:9.

6. The method of claim 5, wherein the ratio is about 1:3.

7. The method of claim 1, wherein the nucleic acid segment comprises a promoter.

8. The method of claim 7, wherein the promoter is CMV or RSV.

9. The method of claim 1, wherein the transient expression persists for at least a day.

10. The method of claim 1, wherein the transient expression persists for at least a week.

11. The method of claim 1, wherein the transient expression persists for at least two weeks.

12. The method of claim 1, wherein the direct injection is by syringe, an osmotic pump, a ventricular cannuli injection device or an intraparenchymal injection device.

13. The method of claim 1, wherein the cytoskeletal protein is a neurofilament protein.

14. The method of claim 13, wherein the neurofilament protein is a 200 kDa, a 150 kDa, or a 68 kDa neurofilament protein.

15. A method for treating nerve cells by transfection comprising the steps of:
   (a) selecting a nerve cell tissue site of a human suffering a traumatic brain or spinal cord injury;
   (b) administering to the cells of said nerve tissue site of said human by direct injection an effective amount of a composition comprising a nucleic acid segment encoding a neurotrophin, and a liposome comprising at least one cationic lipid; wherein said neurotropin is selected from the group consisting of nerve growth factor (NGF) and brain-derived nerve growth factor (BDNF), and wherein said cells of said nerve tissue site in said human are transfected with said composition resulting in the transient expression of said neurotrophin in said cells causing a reduction of neuron death or cytoskeletal protein damage in said nerve tissue site.

16. The method of claim 15 wherein the liposome further comprises a phospholipid and wherein the cationic lipid is DOTMA and the phospholipid is DOPE.

17. The method of claim 16, wherein DOTMA and DOPE are in about a 1:1 ratio.

18. The method of claim 17 wherein the nucleic acid segment and the liposome are in a ratio from about 1:1 to about 1:9.

19. The method of claim 18, wherein the ratio is about 1:3.

20. The method of claim 15, wherein the nucleic acid segment comprises a promoter.

21. The method of claim 20, wherein the promoter is CMV or RSV.

22. The method of claim 15, wherein the transient expression persists for at least a day.

23. The method of claim 15, wherein the transient expression persists for at least a week.

24. The method of claim 15, wherein the transient expression persists for at least two weeks.

25. The method of claim 15, wherein the direct injection is by syringe, an osmotic pump, a ventricular cannuli injection device or an intraparenchymal injection device.

26. The method of claim 15, wherein the cytoskeletal protein is a neurofilament protein.

27. The method of claim 26, wherein the neurofilament protein is a 200 kDa, a 150 kDa, or a 68 kDa neurofilament protein.

\* \* \* \* \*